United States Patent
Gleich et al.

(10) Patent No.: US 11,774,300 B2
(45) Date of Patent: Oct. 3, 2023

(54) PRESSURE SENSOR FOR BEING INTRODUCED INTO A CIRCULATORY SYSTEM

(71) Applicant: KONINKLIJKE PHILIPS N.V., Eindhoven (NL)

(72) Inventors: Bernhard Gleich, Hamburg (DE); Juergen Erwin Rahmer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 677 days.

(21) Appl. No.: 16/708,521

(22) Filed: Dec. 10, 2019

(65) Prior Publication Data
US 2020/0397320 A1 Dec. 24, 2020

(30) Foreign Application Priority Data

Jun. 20, 2019 (EP) .................................... 19181528
Jun. 21, 2019 (EP) .................................... 19181514

(51) Int. Cl.
*A61B 5/0215* (2006.01)
*G01K 7/36* (2006.01)
(Continued)

(52) U.S. Cl.
CPC ............ *G01K 7/36* (2013.01); *A61B 1/00158* (2013.01); *A61B 5/0215* (2013.01); *A61B 5/02152* (2013.01); *A61B 5/05* (2013.01); *A61B 5/062* (2013.01); *A61B 5/6851* (2013.01); *A61B 5/6852* (2013.01); *A61B 34/20* (2016.02); *A61B 90/36* (2016.02); *A61B 90/39* (2016.02); *G01K 1/26* (2013.01); *G01K 13/04* (2013.01);
(Continued)

(58) Field of Classification Search
CPC .......................... A61B 5/02152; G01L 9/0001
See application file for complete search history.

(56) References Cited

U.S. PATENT DOCUMENTS

| | | | |
|---|---|---|---|
| 3,456,508 A | 7/1969 | Frische | |
| 4,127,110 A | 11/1978 | Bullara | |

(Continued)

FOREIGN PATENT DOCUMENTS

| | | |
|---|---|---|
| GB | 1181515 | 2/1970 |
| WO | WO2019243098 A1 | 12/2019 |

OTHER PUBLICATIONS

PCT International Search Report, International application No. PCT/EP2019/084447, dated Jun. 17, 2020.

*Primary Examiner* — Rochelle D Turchen
(74) *Attorney, Agent, or Firm* — Sherry Austin

(57) ABSTRACT

The invention relates to a passive pressure sensor (501) for being introduced into the circulatory system of a human being and for being wirelessly read out by an outside reading system. The pressure sensor comprises a casing (502) with a diffusion blocking layer for maintaining a predetermined pressure within the casing and a magneto-mechanical oscillator with a magnetic object (508) providing a permanent magnetic moment. The magneto-mechanical oscillator transduces an external magnetic or electromagnetic excitation field into a mechanical oscillation of the magnetic object, wherein at least a part of the casing is flexible for allowing to transduce external pressure changes into changes of the mechanical oscillation of the magnetic object. The pressure sensor can be very small and nevertheless provide high quality pressure sensing.

21 Claims, 34 Drawing Sheets

(51) Int. Cl.
  *G01K 1/26*      (2006.01)
  *G01K 13/04*     (2006.01)
  *G01L 9/00*      (2006.01)
  *A61B 34/20*     (2016.01)
  *A61B 90/00*     (2016.01)
  *A61B 5/06*      (2006.01)
  *A61B 1/00*      (2006.01)
  *A61B 5/05*      (2021.01)
  *A61B 5/00*      (2006.01)

(52) U.S. Cl.
  CPC ............ *G01L 9/0001* (2013.01); *G01L 9/007* (2013.01); *A61B 5/02158* (2013.01); *A61B 2034/2051* (2016.02); *A61B 2034/2072* (2016.02); *A61B 2090/3958* (2016.02); *A61B 2090/3966* (2016.02); *A61B 2562/0223* (2013.01)

(56) References Cited

U.S. PATENT DOCUMENTS

| | | |
|---|---|---|
| 7,147,604 B1 | 12/2006 | Allen et al. |
| 2007/0236213 A1 | 10/2007 | Paden |
| 2015/0126829 A1 | 5/2015 | Bernstein |
| 2020/0397530 A1 | 12/2020 | Gleich |
| 2020/0400509 A1 | 12/2020 | Gleich |

PRESSURE SENSOR FOR BEING INTRODUCED INTO A CIRCULATORY SYSTEM

CROSS REFERENCE TO RELATED APPLICATIONS

This application claims priority to EP Application No. 19181528.1 filed Jun. 20, 2019 and EP Application No. 19181514.1 filed Jun. 21, 2019, both of which are incorporated herein by reference.

FIELD OF THE INVENTION

The invention relates to a pressure sensor for being introduced into the circulatory system of a human being. The invention further relates to a stent, a hepatic shunt device, a wire for treating brain aneurism and a heart valve respectively comprising a pressure sensor. Moreover, the invention relates to a reading system, method and computer program for wirelessly reading out a pressure sensor.

BACKGROUND OF THE INVENTION

US 2007/0236213 A1 describes pressure sensing basically based on mechanical resonators with attached magnetized material. A magnetic field can interact with the magnetized material and start a mechanical oscillation. Afterwards, mechanical oscillation is detected by recording the time varying field by the oscillating mechanical structure. The recording device may be a coil or other suitable magnetometer. An external pressure on such a device may change effective spring constants and hence lead to a change in resonance frequency which can be detected. So a pressure sensor is formed.

While this works in principle, it has several shortcomings and is not suitable to measure pressure deep in the patient accurately enough and with a small enough device. The main problem is the use of a mechanical resonator. Typically, the maximum possible quality factor achievable in mechanical resonances is too low for efficient operation. There are some materials like fused silica that would offer a high quality factor in the oscillation. These materials are usually quite hard and do not allow for a high enough oscillation amplitude (high enough angle) to be efficient, i.e. to generate a sufficiently large field variation. The next problem is the low sensitivity of the resonance frequency to the external pressure as only elastic parameters are modified. This combined with the low quality factor results in the need for a quite high signal to noise ratio which in turn results in the need for a high amount of magnetic material which makes the sensor large.

Moreover, there are already implantable pressure sensors e.g. those developed by CardioMems and disclosed in U.S. Pat. No. 7,147,604 B1. These sensors work on the principle that a resonance LC (inductor-capacitor) device is used. The resonance frequency shifts by the mechanical movement induced by the pressure, which in turn either changes the L or C value (or both). While this system works, it cannot be scaled down to a dimension needed for being introduced into the circulatory system of a human being. A main reason is that in U.S. Pat. No. 7,147,604 B1 the detectable signal scales with a high power of the radius of a coil of the pressure sensor. That poses a hard limit for scaling down the pressure sensor.

SUMMARY OF THE INVENTION

It is therefore an object of the present invention to provide a pressure sensor for being introduced into the circulatory system of a human being, which is very small and nevertheless allows for a high quality pressure measurement. The invention further relates to a stent, a hepatic shunt device, a wire for treating brain aneurism and a heart valve respectively comprising a pressure sensor. Moreover, the invention relates to a reading system, method and computer program for wirelessly reading out a pressure sensor.

In a first aspect of the present invention a pressure sensor for being introduced into the circulatory system of a human being is presented, wherein the pressure sensor is a passive sensor which is configured to be wirelessly read out by a reading system placed outside the human being, wherein the pressure sensor comprises a casing with a diffusion blocking layer which covers at least a part of the casing and which is configured to maintain a predetermined pressure within the casing, wherein the pressure sensor comprises within the casing a magneto-mechanical oscillator with a magnetic object providing a permanent magnetic moment, wherein the magneto-mechanical oscillator is configured to transduce an external magnetic or electromagnetic excitation field into a mechanical oscillation of the magnetic object, wherein at least a part of the casing is flexible for allowing to transduce external pressure changes into changes of the mechanical oscillation of the magnetic object.

Since the pressure sensor uses a magneto-mechanical oscillator which mainly uses magnetism to store the oscillation energy, a high quality factor, a high oscillation amplitude, and a high sensitivity to external influences can be achieved at the same time with a very small pressure sensor being suitable for being introduced into the circulatory system of a human being.

The dimensions of the pressure sensor are preferentially such that they can be introduced into the circulatory system outside the main pulmonary artery. Preferentially, the pressure sensor has an elongated shape with a maximum dimension being smaller than or equal to 5 mm, further preferred being smaller than or equal to 4 mm, and a minimum dimension being smaller than or equal to 1 mm. These dimensions preferentially refer to a longitudinal direction and a transversal direction of the pressure sensor. Thus, preferentially, in the longitudinal direction the dimension of the pressure sensor is smaller than or equal to 5 mm, further preferred smaller than or equal to 4 mm, and in the transversal direction the dimension of the pressure sensor is smaller than or equal to 1 mm.

In a preferred embodiment the pressure sensor comprises an external biocompatible coating. Moreover, preferentially the flexible part of the casing comprises a bellows for allowing to transduce the external pressure changes into changes of the mechanical oscillation of the magnetic object. The bellows is particularly suited for allowing to transduce the external pressure changes into changes of the mechanical oscillation of the magnetic object, because they provide flexibility being sufficient for pressure measurements, even if coated with, for instance, the diffusion blocking layer and/or the biocompatible coating. The bellows can be made of a rather flexible material like silicone rubber.

The pressure sensor might further comprise an outer cover over the bellows. The outer cover can be used to avoid blood clot formation. The outer cover is preferentially sufficiently soft to allow the bellows to change in response to the external pressure.

The diffusion blocking layer preferentially comprises metal. For instance, it can be provided as a metal coating on the casing of the pressure sensor.

In an embodiment the pressure sensor further comprises an outer wire cage attached to the outer of the casing for allowing the outer of the casing to keep a distance to a vessel wall. The wire cage can be advantageous for direct delivery into a vessel, wherein the cage might fixate the pressure sensor without blocking the vessel lumen. The cage can comprise a ring or disk shaped center part from which bended legs protrude. It can be manufactured from wire material, e.g. Nitinol for its high flexibility and good biocompatibility. Other materials, like stainless steel or polymers could also be used. An alternative to wires are structures cut out of sheet materials, which can be brought into a bended shape using a mold tool and heat treatment. Especially for polymers, injection molding is also feasible. For connection to the sensor casing, the ring or disk shaped structure can act as an interface between cage and sensor casing. A ring-shape structure can be slit on the cylindrical casing and can be fixated by spring force and/or by gluing or welding. A disk-shaped structure can be glued or welded to the pressure sensor.

In a preferred embodiment the magnetic object is arranged within the casing such that it is rotatable out of an equilibrium orientation if the external magnetic or electromagnetic excitation field is acting on the magnetic object, wherein the pressure sensor further comprises a restoring torque unit being adapted to provide a restoring torque to force the magnetic object back into the equilibrium orientation if the external magnetic or electromagnetic excitation field has rotated the magnetic object out of the equilibrium orientation, in order to allow for the mechanical oscillation of the magnetic object with a resonance frequency, wherein the pressure sensor is configured such that the external pressure changes are transduced into changes of the resonance frequency.

The restoring torque unit can comprise a further magnetic object for generating a magnetic field at the position of the magnetic object such that it provides the restoring torque and/or a torsional spring mechanism for providing the restoring torque. Moreover, besides the magnetic object, also the further magnetic object, if present, is preferentially a permanent magnet. Furthermore, the magnetic object is preferentially a magnetic sphere. Also the further magnetic object, if present, can be a magnetic sphere. However, the magnetic object and, if present, also the further magnetic object, can also have another shape. For instance, they can be cylindrical. The magnetic object is preferentially attached to one end of a filament, wherein another end of the filament is attached to the casing. Also the further magnetic object, if present, can be attached to one end of a filament, wherein another end of the filament can be attached to the casing. However, the further magnetic object can also be fixed.

In an embodiment the magnetic object and/or the inner of the casing is coated with a slippery non-sticking material. Preferentially, the slippery non-sticking material is graphite. Also the further magnetic object can be coated with a slippery non-sticking material. Preferentially, the non-sticking material is regarded as being "slippery", if the coefficient of friction in dry condition, i.e. not lubricated, is below 0.2 and further preferred below 0.1.

Generally, if the pressure sensor has been introduced into the body of the human being, it can be problematic if the body should be scanned in a magnetic resonance imaging (MRI) scanner. The problem is not a danger to the body, i.e. to the patient, because the pressure sensor is relatively small and hence only small forces and torques are caused, that are not a threat to patients. Likewise, an MR image generated by the MRI scanner might also not be spoiled since the pressure sensor is relatively small. However, high field strengths of more than 1.5 T are used in many clinical MRI scanners and the strong magnetic field might destroy the pressure sensor by changing the magnetization of the magnetic object or by damaging a mechanical arrangement within the device. For this reason, in an embodiment the pressure sensor is constructed such that the magnetic object is alignable with an external magnetic field regardless of the position and orientation of the pressure sensor in the external magnetic field. For instance, the pressure sensor can comprise an outer housing enclosing the casing, wherein the casing is rotatable within the enclosing housing, wherein the pressure sensor is configured such that external pressure changes outside the enclosing housing are transferred to external pressure changes being externally of the casing and internally of the enclosing housing. The outer housing can be spherical or elliptical. Moreover, the outer housing can also be filled with fluid, wherein the fluid is preferentially a highly viscous fluid. The term "highly viscous" preferentially refers to a viscosity which is such that in a magnetic flux density of 0.1 T, the maximum rotation speed of the device is limited to below 10000 degrees per second or an angular velocity not higher than 160 1/s. For typical device configurations, this translates to viscosities of between 1 and 100 Pas as minimum. The main determining factor is the volume fraction of hard magnetic material. There is also a maximum useful viscosity which is about 100 to 1000 times the minimum useful viscosity.

The housing can be, for instance, a very soft housing filled with fluid or a housing with openings, in order to effectively transduce external pressure changes to changes of the mechanical oscillation of the magnetic object. Preferentially, the housing is regarded as being "very soft", if the pressure change inside the housing does not deviate more than 0.2 mbar (20 Pa) from the outside pressure on the time scale of the expected pressure change which is typically between 0.01 and 1 s. The hardest known substance brought into the right shape with sufficient low thickness can form a "very soft" housing. Then the housing preferentially incorporates structures that act as bellows.

The magnetic object is preferentially a magnetic sphere which is attached to one end of a filament, wherein another end of the filament is attached to the inner of the casing, wherein in an embodiment the filament has a length of at least Pi/4 of the diameter of the magnetic sphere. If also the further magnetic object is a magnetic sphere, it can be attached to one end of another filament, wherein another end of the other filament is attached to the casing. Preferentially also the other filament has a length of at least Pi/4 of the diameter of, in this case, the other magnetic sphere. These lengths of the filaments allow for a free alignment of the magnetic objects with the external magnetic field. The magnetic sphere and the other magnetic sphere preferentially have the same diameter.

Moreover, in an embodiment the magnetic object is a magnetic sphere which is attached to one end of a filament, wherein another end of the filament is attached to a length changing unit configured to allow for a change of the length of the filament and attached to the inner of the casing. The length changing unit can be, for instance, a spooling unit. The spooling unit can comprise a winding mechanism. Preferentially, the pressure sensor is adapted such that the length of the filament from the magnetic sphere to the length changing unit is adjustable such that it is equal to a predefined length. For instance, the filament and/or the length changing unit can comprise a stopper arranged and configured to stop, while the length changing unit shortens the length of the filament, a further shortening of the filament, if the length of the filament from the magnetic sphere to the length changing unit has reached the predefined length. In an embodiment the stopper is arranged and configured to stop a winding up of the filament, if the length of the filament from the magnetic sphere to the spooling unit has reached the predefined length.

In an embodiment the length changing unit comprises a spring with a spring force, wherein the spring is configured such and the filament is attached to the spring such that the spring force forces the filament out of the casing of the pressure sensor and into the length changing unit, in order to shorten the length of the filament within the casing of the pressure sensor, and that the length of the filament within the casing of the pressure sensor is increasable, if a force acting on the magnetic object pulls the filament out of the length changing unit against the spring force. The length changing unit can comprise a stopper configured and arranged to restrict a relaxation of the spring such that the filament within the casing of the pressure sensor has a predefined length, if no force is acting against the spring force.

In a preferred embodiment the pressure sensor is configured to compensate a dependence of the resonance frequency on the temperature. In particular, the pressure sensor comprises a compensation element which is adapted to modify the resonance frequency in a first frequency direction depending on a temperature change which is opposite to a second frequency direction in which the resonance frequency of the pressure sensor would be modified, depending on the temperature change, if the compensation element were not part of the pressure sensor. Since the measurement device comprises a compensation element which is adapted to modify the resonance frequency in a first frequency direction depending on a temperature change which is opposite to a second frequency direction in which the resonance frequency would be modified, depending on the temperature change, if the compensation element were not part of the pressure sensor, temperature induced shifts of the resonance frequency can be reduced or even eliminated. The first frequency direction is a direction towards higher or lower frequencies and the opposite second frequency direction is a direction towards lower or higher frequencies, respectively.

Preferentially the compensation element comprises magnetic material which changes its magnetization and thereby the resonant frequency with temperature, wherein the magnetic material is chosen and arranged within the pressure sensor, particularly within the casing, such that the direction of the modification of the resonance frequency is the first frequency direction. The compensating magnetic material is preferentially arranged adjacent to the magnetic object and/or adjacent to the further magnetic object if present. This allows to design the pressure sensor such that an unwanted temperature dependence can be significantly reduced or even eliminated in a technically relatively simple way and without requiring much space within the casing.

In an embodiment the magnetic object is a magnetic sphere which is attached to one end of a filament, wherein another end of the filament is directly or indirectly attached to the casing, wherein the magnetic sphere comprises a through hole through the center of gravity of the magnetic object, wherein the one end of the filament is arranged and fixed in the through hole. This attachment reduces a magnetic dipole moment only by a small fraction and therefore retains a good signal. The shape of the magnetic object is not much altered which may be important in the case of spheres.

Furthermore, in an embodiment the magnetic object is a magnetic sphere which is attached to one end of a filament, wherein another end of the filament is directly or indirectly attached to the casing, wherein the one end of the filament is clamped between two magnetic components of the magnetic object, which form the magnetic object. This attachment method produces results almost as good as the through hole attachment method, but requires no special equipment for the manufacturing.

In an embodiment the magnetic object is a magnetic sphere which is glued to one end of a filament, wherein another end of the filament is directly or indirectly attached to the casing. This method is technically very simple and uses the magnetic object to full extend.

Moreover, in an embodiment the magnetic object is a magnetic sphere attached to a non-magnetic object and the non-magnetic object is attached to one end of a filament, wherein another end of the filament is directly or indirectly attached to the casing. Also this allows for a relatively simple attachment of the filament to the magnetic object.

In a further aspect of the present invention a stent comprising the pressure sensor is provided. For instance, the pressure sensor can be arranged on a distal side of a stent to indicate in-stent restenosis. In an embodiment the stent comprises several pressure sensors, in order to, for instance, monitor a pressure drop over the complete stent or a part of it as a parameter for in-stent restenosis. Early detection allows adjustment of medication or timely re-stenting, thus avoiding unplanned hospitalization.

In a further aspect of the present invention a hepatic shunt device comprising the pressure sensor is provided. For instance, the pressure sensor can be arranged on a proximal side of the shunt device, in order to monitor whether pressure reduction works, i.e. the shunt is open. Also the hepatic shunt device can comprise several pressure sensors, particularly for monitoring a pressure drop. Moreover, also here early detection allows adjustment of medication or timely re-stenting, thus avoiding unplanned hospitalization.

In a further aspect of the present invention a wire for treating of brain aneurism is provided, which comprises the pressure sensor. The wire might be used for coiling which should lead to blood coagulation to fill the aneurism space. The pressure sensor can be used for indicating whether coagulation really takes place, i.e. that the pulsatile blood pressure variation is reduced.

In a further aspect of the present invention a heart valve comprising the pressure sensor is provided. For instance, a first pressure sensor can be placed at a proximal side and a second pressure sensor could be placed at a distal side of the heart valve, in order to monitor a pressure drop over the phases of a heartbeat. From monitored dynamic pressure variation, information about the function of the valve can be extracted. A localization sensor could also be placed directly on the movable part of the valve, to not only deliver pressure information, but also motion information via spatial localization and determination of the orientation of the sensor.

In a further aspect of the present invention a reading system for wirelessly reading out a pressure sensor as defined by any of claims 1 to 15 is provided, wherein the reading system comprises:

- a field generator for generating a magnetic or electromagnetic excitation field for inducing mechanical oscillations of the magnetic object of the pressure sensor,
- a transducer for transducing a magnetic or electromagnetic field generated by the induced mechanical oscillations of the magnetic object of the pressure sensor into electrical response signals, a processor for determining a pressure value based on the electrical response signals.

The field generator and the transducer can be two separate units or they can be integrated, wherein, if the field generator and the transducer are integrated, same coils can be used for generating the magnetic or electromagnetic excitation field and for transducing a magnetic or electromagnetic field generated by the induced mechanical oscillation of the magnetic object of the pressure sensor into electrical response signals.

In a preferred embodiment the processor is configured to apply a compensation algorithm, in order to correct the pressure value determination for a dependence of the resonance frequency on at least one of a) a distance between the pressure sensor and the field generator and b) an in-phase coil excitation.

A large magnetic moment of the magnetic object is desirable, because it would create a stronger response to be picked by the transducer, which might comprise corresponding pickup coils. However, a large magnetic moment means a large restoring force, which means that the resulting oscillatory motion would have a large amplitude. When large oscillation take place, at large angular displacement the restoring force is reduced. Consequently, for such oscillation the response frequency will depend on the restoring force, which is dependent on the distance between coils of the field generator and pressure sensor. In order to solve this problem, the processor can be adapted to correct the pressure value determination for a dependence of the resonance frequency on a distance between the pressure sensor and the field generator.

Intravascular pressure varies during the cardiac cycle. Regular cardiac rates in human being are normally around 50 to 90 beats per minute with possible maxima as high as 200 beats per minute. In order to determine pressure minima and maxima during a cardiac cycle, the measurement frequency should not be smaller than about 5 Hz. Preferentially, the measurement frequency is above 10 to 20 Hz, most preferably above 40 Hz. On the other side, in order to have a good signal to noise ratio, a very high Q factor for the oscillator is preferred, wherein high Q factor means a slow decay. Consequently, when a next measurement pulse is send to the sensor, the oscillations from the previous measurement pulse may not be fully extinguished and they would affect the measurement. Thus, by compensating for this in-phase coil excitation, a high Q factor can be better combined with a measurement frequency being large enough to allow a measurement of cardiac minima and maxima.

In a further aspect of the present invention a pressure measuring method for carrying out a measurement by using a pressure sensor as defined by any of claims 1 to 15 is presented, wherein the pressure measuring method comprises:
- generating a magnetic or electromagnetic excitation field for inducing mechanical oscillations of the magnetic object of the pressure sensor,
- transducing a magnetic or electromagnetic field generated by the induced mechanical oscillations of the magnetic object of the pressure sensor into electrical response signals,
- determining a pressure value based on the electrical response signals.

Moreover, in a further aspect of the present invention a computer program is presented, which comprises program code means for causing the reading system as defined by claim 20 to carry out the steps of the pressure measuring method, when the computer program is run on a computer controlling the reading system.

It shall be understood that the pressure sensor of claim 1, the stent of claim 16, the hepatic shunt device of claim 17, the wire of claim 18, the heart valve of claim 19, the reading system of claim 20, the pressure measuring method of claim 22 and the computer program of claim 23 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
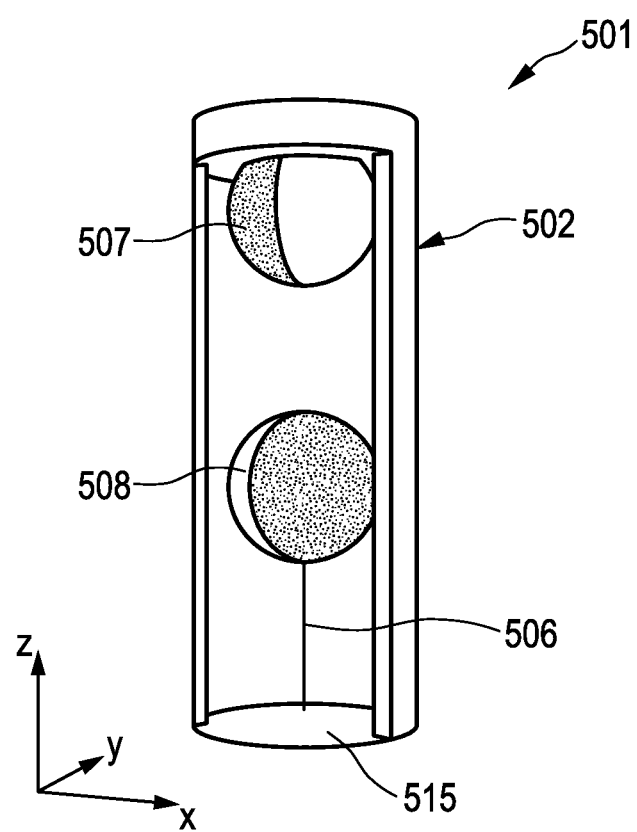
FIG. 1 shows schematically and exemplarily an embodiment of a pressure sensor in a situation with a first external pressure.

FIG. 1 schematically and exemplarily shows an embodiment of a pressure sensor 501 for being introduced into the circulatory system of a human being. The pressure sensor 501 comprises a magneto-mechanical resonator with two magnetic elements 507, 508.

The magnetic element 508 is suspended from a filament 506 and is thus free to perform a rotational motion about the resonator main axis. In this embodiment the further magnetic object 507 is fixed. However, in another embodiment the further magnetic element can also be suspended from a filament and thus can be free to perform a rotational motion about the resonator main axis.

In equilibrium, the magnets 507, 508, respectively, align with anti-parallel orientation of their magnetization. An external magnetic field pulse can be used to start a resonance rotational oscillation. The attractive force determines the resonance frequency of the oscillation, which for a spherical suspended magnet is given by $$\omega_0 = \sqrt{\frac{5\, M_S B}{2\rho r^2}}, \quad (1)$$

where $M_S$ is the saturation magnetization of the magnetic material, $\rho$ is its density, $r$ is the sphere diameter, and $B$ is the field created by the fixed magnet. It can be approximated as a dipole field $$B(r) = \frac{\mu_0}{4\pi}\left(\frac{3r(m\cdot r)}{r^5} - \frac{m}{r^3}\right), \quad (2)$$

where $m$ is the magnetic moment of the magnet.

The field variation generated by the oscillating magnetic element can be detected via the induced voltage in one or several detection coils of a transducer, which is configured to transduce a magnetic or electromagnetic field generated by the mechanical oscillations of the magnetic object of the pressure sensor into electrical response signals. The time trace of the detected signal (cf. FIG. 13) can be Fourier-transformed to obtain the spectrum (cf. FIG. 16), which enables determination of the resonance frequency.

Due to the low resonance frequencies of a few kHz, the magnetic fields are not shielded by metal and thus all non-ferromagnetic metals can be used as structural or coating materials. Likewise, the sensor can be placed into non-ferromagnetic metallic objects without effects on its operation, as long as the metal thickness does not strongly exceed the skin depth. At these frequencies, for very good conductors like copper, the skin depth is of the order of one millimeter, while for Nitinol, the skin depth is around 10 millimeters.

The basic magneto-mechanical oscillator contains two magnetic elements, wherein, in equilibrium, the magnetic elements align with anti-parallel magnetization. An external field pulse can be used to start a rotational oscillation of the suspended sphere about the main axis of the resonator, wherein the other sphere, i.e. the further magnetic object, is fixed. If in another embodiment also the other sphere is suspended in free space and can perform a rotational oscillation, both spheres can perform a resonance counter-oscillation.

US 2007/0236213 A1 describes basically mechanical resonators with attached magnetized material. A magnetic field can interact with the magnetized material and start a mechanical oscillation. Afterwards, mechanical oscillation is detected by recording the time varying field by the oscillating mechanical structure. The recording device may be a coil or other suitable magnetometer. An external pressure on such a device may change effective spring constants and hence lead to a change in resonance frequency which can be detected. So a pressure sensor is formed.

While this works in principle, it has, as also mentioned above, several shortcomings and is not suitable to measure pressure deep in the patient accurately enough and with a small enough device. The main problem is the use of a mechanical resonator. Typically, the maximum possible quality factor achievable in mechanical resonances is too low for efficient operation. There are some materials like fused silica that would offer a high quality factor in the oscillation. These materials are usually quite hard and do not allow for a high enough oscillation amplitude (high enough angle) to be efficient, i.e. to generate a sufficiently large field variation. The next problem is the low sensitivity of the resonance frequency to the external pressure as only elastic parameters are modified. This combined with the low quality factor results in the need for a quite high signal to noise ratio which in turn results in the need for a high amount of magnetic material which makes the sensor large. A further problem of the device disclosed in US 2007/0236213 A1 is the integration of a high strength permanent magnet into the device. The best permanent magnets are the sintered types. These are not compatible with a MEMS production process. So either the production is complicated or inferior magnetic material has to be used. A positive factor is the relative high operation frequency of the sensor disclosed in US 2007/0236213 A1. The down side is that the noise in the body also increases with frequency and above a few 100 kHz, there is no more gain. So the claimed GHz resonance frequencies do not help. A high frequency operation also needs a fast switching from send to receive mode, which is technically challenging. A further problem of US 2007/0236213 A1 is the durability. At sufficient high amplitude-times-frequency product, the spring material is stressed considerably which may lead to breaking.

These problems are avoided by the design proposed, for instance, in FIG. 1. As the energy is stored mainly in the magnetic field, it is relatively easy to attain a high quality factor. High oscillation amplitudes are also easily possible. The thin filament is not subjected to strong wear. The resonance can be easily changed by changing the magnetic field by a mechanical movement of magnets relative to each other. This is also easily matched to a pressure change (using the right compliance and right shape materials as discussed below), so a quite high frequency change can be reached. The sensor can be made from the best available magnetic material and the volume fraction of magnetic material is high.

There are, as also explained above, already implantable pressure sensors e.g. those developed by CardioMems and disclosed in U.S. Pat. No. 7,147,604 B1. These sensors work on the principle that a resonance LC (inductor-capacitor) device is used. The resonance frequency shifts by the mechanical movement induced by the pressure, which in turn either changes the L or C value (or both). While this system works, it cannot be scaled down to a dimension needed for the envisioned applications. This is an inherent problem of the LC oscillator. With reduced size, the power level that can be generated at the oscillator and the dynamic dipole moment generated by the power diminish. This can be seen in the following equation. The quality factor of the resonator cannot be higher than the quality factor of the coil. An approximation for the quality factor of the coil can be written as:

$$Q = \omega \frac{\mu_0}{2\rho} \tau r^2, \quad (3)$$

where $\omega$ is the frequency, $\mu_o$ the vacuum permeability, $\rho$ the resistivity, $\tau$ the fraction of the radius consisting of conductor, and r the radius of the coil. The coil is assumed to be cylindrical with diameter matching the height. For a 1 mm diameter copper coil at 100 kHz, a quality factor of about 1 is got. This is clearly not going to work. For the 1 cm (or more) coils used by CardioMems, the quality factor is above 100 at 100 kHz and above 1000 at 1 MHz. The above formula overestimates the practically achievable Q values as it assumes that all volume is filled with conduction material and neglect proximity and skin effects as well as the losses in the capacitor. Nonetheless, these values lead to a working system. U.S. Pat. No. 7,147,604 B1 states a measured quality factor of 48 between 1 and 100 MHz. As the dynamic dipole moment of an LC oscillator is Q times external magnetic field times volume, the signal scales with $r^5$, while in the case of a mechanical oscillator (energy stored in elasticity) the signal scales with $r^3$, and in the case of the embodiments described, for instance, with reference to FIG. 1 (magneto-mechanical oscillator, energy stored in magnetic field), the signal scales with $r^2$, as the frequency is inversely proportional to the linear dimensions. So the proposal presented here is very good suited for sensor miniaturization.

In the embodiment with a fixed sphere, the fixed sphere might have a diameter of 620 µm, whereas the oscillating sphere 108 might have a diameter of 500 µm. The magnetic moment of the oscillating sphere 108 might be m≈70 µAm², the base frequency might be $f_0$≈2 kHz, and the quality factor might be roughly Q≈500. SNR depends on distance between a) a coil used for reading out the resonance frequency and b) the sensing device as well as coil parameters. For a handheld coil with diameter 10 cm, 200 windings, and a resistance of 10 Ohm, the theoretically achievable SNR at a distance of about 30 cm and a sampling duration of 0.1 s is roughly 4000. However, typical SNR values of a demonstrator with a fixed sphere might be between 10 and 100, if hardly no measures for background signal suppression have been implemented. Noise is therefore mainly determined by fluctuations of the mains power supply harmonics. For half the sphere diameters, i.e., for instance, 250 µm for the oscillating sphere, magnetic moment could be m≈9 µAm², the base frequency could be $f_0$≈4 kHz, the quality factor could remain unchanged, and theoretical SNR could drop to about 1000.

There are several ways how to attach the thread to the movable magnetic object.

For instance, a through hole attachment can be used. In this case a hole is drilled through the center of gravity and roughly perpendicular to the magnetization. Although the magnet material is hard and brittle, there are several methods to drill the holes, like pulsed laser or electrical discharge machining (EDM). The thread is run through the hole and glued in place. Running through is best done using a vacuum suction process. Several glue types can be used. Economic are light curing glues. They should have a low viscosity to fill the hole with the treads simply by capillary force. Alternatively or in addition the thread can be fixed to the magnetic object by mechanical means. E.g. by having a knot in the thread or some other thick portion in the tread like a glue droplet or a heat generated (melted) bead. The latter is especially easily made in UHMWPE fibers. This attachment method reduces the magnetic dipole moment only by a small fraction and therefore retrains good signal. The shape of the magnetic object is not much altered which may be important in the case of spheres.

Also a clamp attachment can be used. In this case the magnetic object is split in at least two components. Preferably a split plane is generated orthogonal to the magnetization and parallel to the thread attachment direction. The thread, i.e. the filament, is placed on this plane. Precise alignment is not necessary. The second magnetic part is placed on top. The magnetic parts are usually held together by magnetic forces. Finally, glue is applied to secure everything in place. Preferred glue types are the same as in the through hole attachment process. In addition, it is possible to grind a groove in one or both of the magnetic objects to reduce the overall gap between the magnetic objects. This method produces results almost as good as the through hole method, but requires no special equipment for the manufacturing. Usually, the magnetic sub-objects are not made by splitting a single full magnetic object, but by grinding down two (identical) magnetic objects. The down side is that this process is more wasteful as two initial objects are used and it may be also somewhat more labor intense.

The cheapest method is the direct attachment of the thread top the magnetic object using a suitable glue. The magnetic object is held and aligned in some sort of tool. Both functions may be realized by suitable magnetic fields. The tool may be a funnel shaped with a thread running through the funnel and the magnetic object is attached to the funnel opening by magnetic forces. Glue is applied in the funnel and cured. Then the assembly is extracted from the tool and the unwanted portion of the tread is cut. This method can be very cheap and uses the magnetic object to full extend. The drawback is that considerable material is added, reducing oscillation frequency and requiring space in the completed device.

In a further embodiment, a structure to attach and additional gluing can be used. It is possible to attach the thread to the magnetic object by first attaching it to a non-magnetic object and then gluing the non-magnetic object to the magnetic one. The non-magnetic object may be manufactured by injection molding or an equivalent cheap process. The shape of the non-magnetic object should allow for a simple thread attachment i.e. it may have a hole or a clamping mechanism, maybe even as simple as a notch. The non-magnetic object is then glued to the magnetic object. Alternatively, it may be clamped or screwed to the magnetic object. This method is simple and cheap, but may need too much additional space for some applications.

In principle, all the methods discussed for thread-magnetic object attachment apply in the same way to thread-casing attachment. However, as the casing material is usually simpler to work with, the trough-hole method may be a good choice. Clamping is also a good option. This may be cheaper but may be harder to be finally sealed.

Figure 2:
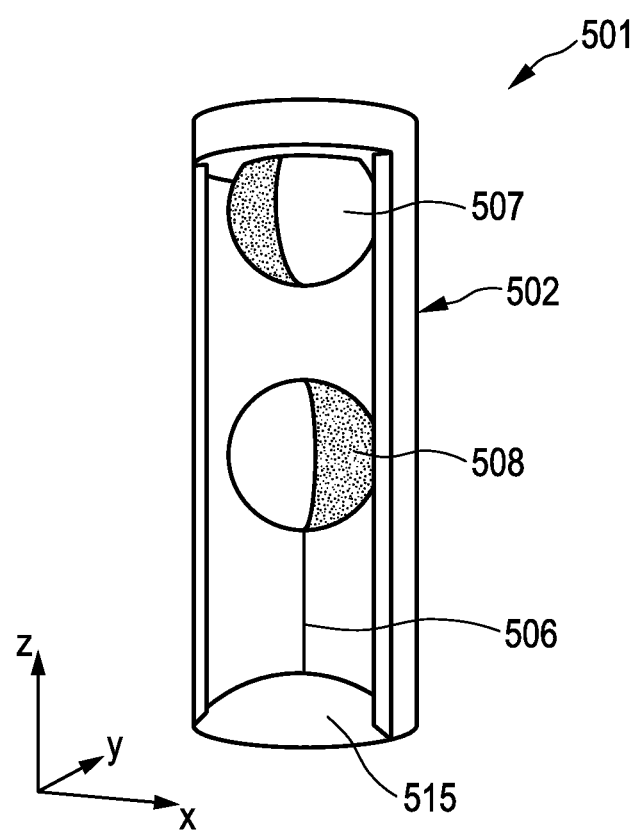
FIG. 2 shows schematically and exemplarily the embodiment of FIG. 1 in a situation with a second pressure being larger than the first pressure.

At least a part of the casing is flexible for allowing to transduce external pressure changes into changes of the mechanical oscillation of the magnetic object. Preferentially the casing comprises a deflectable membrane as schematically and exemplarily shown in FIGS. 1 and 2. The deflection depends on pressure exerted on the sensor and changes the inter-sphere distance. A reduction in distance results in an increase of the resonance frequency and vice versa. In FIGS. 1 and 2 the basic pressure sensor working principle can be seen. An increase in pressure deflects the membrane 515 and reduces the distance between the spheres 507, 508, resulting in an increase in resonance frequency. FIGS. 1 and 2 further show a casing 502 and a filament 506 via which the magnetic sphere 508 is attached to the membrane 515. In FIG. 1 the pressure acting on the membrane and the resonance frequency are smaller than in FIG. 2.

Figure 3:
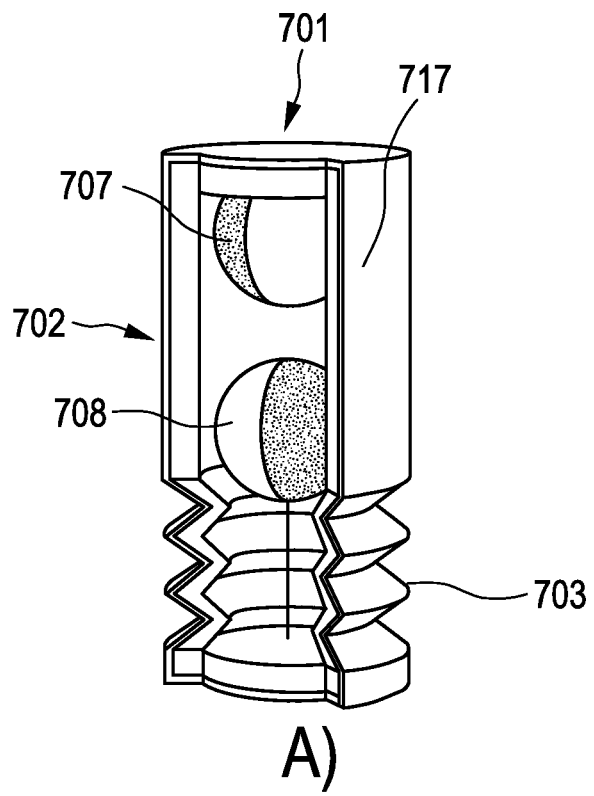
FIG. 3 shows schematically and exemplarily different embodiments of a pressure sensor with a bellows.
Figure 3:
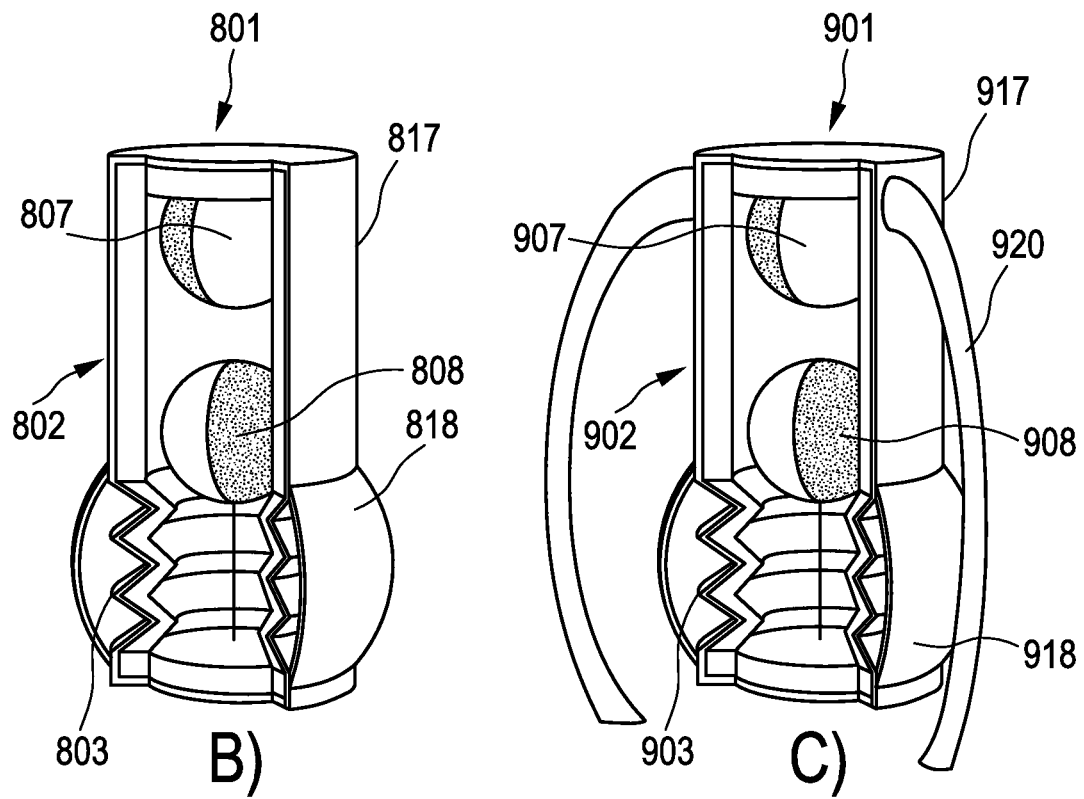

FIG. 3 shows bellows designs, i.e. further embodiments of the pressure sensor with a bellows. The bellows yields to the forces resulting from the pressure acting on the sensor, i.e. a pressure increase compresses the bellows and reduces the inter-sphere distance. FIG. 3A shows a first bellows design. The bellows 703 is designed to use the space available around the filament 706 without increasing the outer sensor diameter, wherein a pressure increase compresses the bellows 703 and reduces the distance between the magnetic spheres 707, 708, leading to an increase in resonance frequency. FIG. 3A further shows a casing 702 and a fixed magnetic sphere 707 of the pressure sensor 701. The pressure sensor 701 further comprises a thin metal coating 717 acting as diffusion barrier, i.e. a diffusion blocking layer. It should be noted that all embodiments of the present invention comprise a diffusion blocking layer, even if not explicitly shown in all figures for clarity reasons.

FIG. 3B shows a coated sensor 801, which is similar to the pressure sensor shown in FIG. 3A, with an additional smooth and soft cover over bellows 818 to avoid blood clot formation. Also the sensor 801 comprises bellows 803 designed to use the space available around the filament without increasing the outer sensor diameter, wherein a pressure increase compresses the bellows 803 and reduces the distance between the magnetic spheres 807, 808, leading to an increase in resonance frequency. FIG. 3B further shows a casing 802 and a fixed magnetic sphere 807 of the pressure sensor 801. The pressure sensor 801 further comprises a thin metal coating 817 acting as diffusion barrier, i.e. a diffusion blocking layer.

Figure 4:
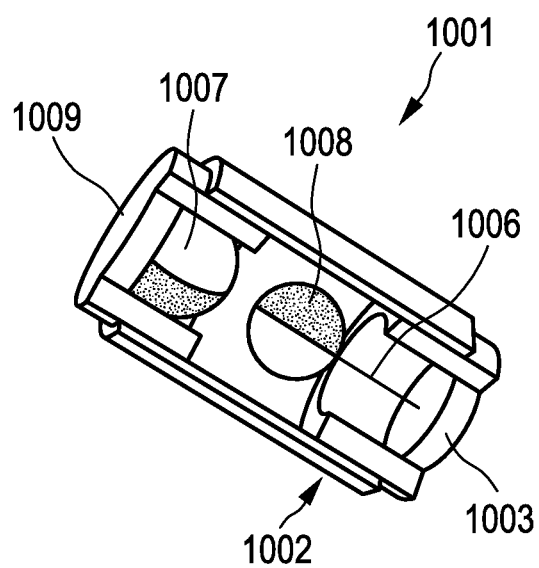
FIG. 4 shows schematically and exemplarily a further embodiment of a pressure sensor.

FIG. 3C shows a pressure sensor 901, which is similar to the pressure sensor shown in FIG. 3B, additionally with 3-element wire cage 920 for direct delivery into a vessel. The cage fixates the sensor without blocking the vessel lumen. Thus, also in this embodiment a smooth and soft cover 918 is present over a bellows 903 to avoid blood clot formation. The bellows 903 are designed to use the space available around the filament without increasing the outer sensor diameter, wherein a pressure increase compresses the bellows 903 and reduces the distance between the magnetic spheres 907, 908, leading to an increase in resonance frequency. FIG. 3C further shows a casing 902 and a fixed magnetic sphere 907 of the pressure sensor 901. The pressure sensor 901 further comprises a thin metal coating 917 acting as diffusion barrier, i.e. a diffusion blocking layer The bellows can be made in different ways. First the bellows can be made from a rather flexible material like silicone rubber (cf. FIG. 4). In fact, it may be simply a piece of silicone rubber. In FIG. 4 the pressure sensor 1001 comprises a cylindrical casing 1002 having to open ends closed by using rubber elements 1009, 1003, wherein a first rubber element 1009 holds a fixed magnetic sphere 1007 and a second rubber element 1003 holds an rotationally oscillatable magnetic sphere 1008 via a filament 1006. The cylindrical rubber element 1003 is acting as expansion joint instead of a bellows.

However, when incorporating at least one diffusion dense layer to the bellows, i.e. when coating the bellows with the diffusion blocking layer, for instance, as described above with reference to FIGS. 3A to 3C, a simple tube is usually too stiff. Therefore, a real bellows structure is preferred. Bellows are well-known and different shapes of the bellows are possible. Especially the "origami"-type of structure is well suited to the pressure sensor application. There are several ways to manufacture the bellows. It can be simply made in an injection molding process. This has the advantage that the bellows can be manufactured together with the housing in a single step. However, as the membrane needs to be very thin, the manufacturing process is challenging. An alternative is to produce only the inner free space of the bellows in a production process like injection molding or even a turning or milling process. The material should be easily dissolvable, like polyvinyl alcohol or polystyrene. Some metals are also suitable, like aluminum, iron or copper. On this material, the bellows structure is deposited and the inner structure is removed by a suitable solvent and/or application of heat. Many deposition processes are suitable to generate the bellows. For example, a noble metal (gold, palladium etc.) can be electrochemically deposited. Metals, compounds and polymers can be thermally deposited in a vacuum. Sputter processes are suitable as well as chemical vapor depositions. Many others, like simple painting may work, too. While pure metal bellows work, it is best to combine metal with a polymer, because it gives less stiff bellows. It is also efficient to integrate at least two or more very thin metal layers. So, for example, it is good to first deposit (sputter) a gold palladium layer, then use a CVD process to deposit parylene-C, then again sputter a gold alloy on top. This allows the diffusion barrier to function even if a few cracks appear in the metal layer, because the gas has to diffuse a long distance in the parylene layer which is already quite resistant to diffusion. There may or may not be additional layers on top to augment biocompatibility, i.e. each of the described embodiments might comprise one or several outer biocompatible layers. Instead of using an inner mold, the use of external molds is possible, too. They have to split open to release the bellows, but maybe reused multiple times. Physical deposition methods may work not so well for this production process, but chemical deposition and electrochemical deposition are suitable, for example. The other deposition processes as mentioned above can be used, once the (unfinished) bellows is removed from the mold.

As described above, there are many ways to coat the sensor. It is especially useful to coat the final sensor once again with metal, for instance, as described above with reference to FIGS. 3A to 3C. This makes all the possible joints diffusion tight. Here again physical or chemical vapor depositions are useful. On top of this layer (or as an alternative) a bio-compatible coating like parylene-C may be deposited, if needed. Otherwise a noble metal or titanium coating offers already good bio-compatibility.

As shown in FIGS. 3B and 10C, a smooth and soft top layer 818, 918 can be added to avoid the formation of blood clots at the rather sharp edges of the bellows. The void between the soft layer 818, 918 and the bellows can be filled by a fluid, e.g. water or silicone oil.

FIG. 3C shows a sensor 901 with a 3-element wire cage 920 for direct delivery into a vessel. The cage fixates the sensor without blocking the vessel lumen. The cage typically consists of a ring or disk shaped center part from which bended legs protrude. It can be manufactured from wire material, e.g. Nitinol for its high flexibility and good bio-compatibility. Other materials, like stainless steel or polymers would also work. An alternative to wires would be structures cut out of sheet materials, which would then be brought into a bended shape using a mold tool and heat treatment. Especially for polymers, injection molding would also be feasible. For connection to the sensor housing, the ring or disk shaped structure acts as an interface between cage and sensor housing. A ring-shape structure can be slit on the cylindrical housing and can be fixated by spring force and/or by gluing or welding. A disk-shaped structure can be glued or welded to the sensor.

To avoid forces resulting from vessel wall contact, the cage 920 connects to only one part of the sensor 901 and protects the space around the other part (cf. FIG. 3C). It can either be connected to the part containing the fixed magnetic element or to the part with the rotatable magnet. The cage design can also contain helical structures (single or multi-wire) or mesh-like structures. These structures can be optimized for being compressed, e.g. during a trans-venous delivery through a thin needle.

Figure 5:
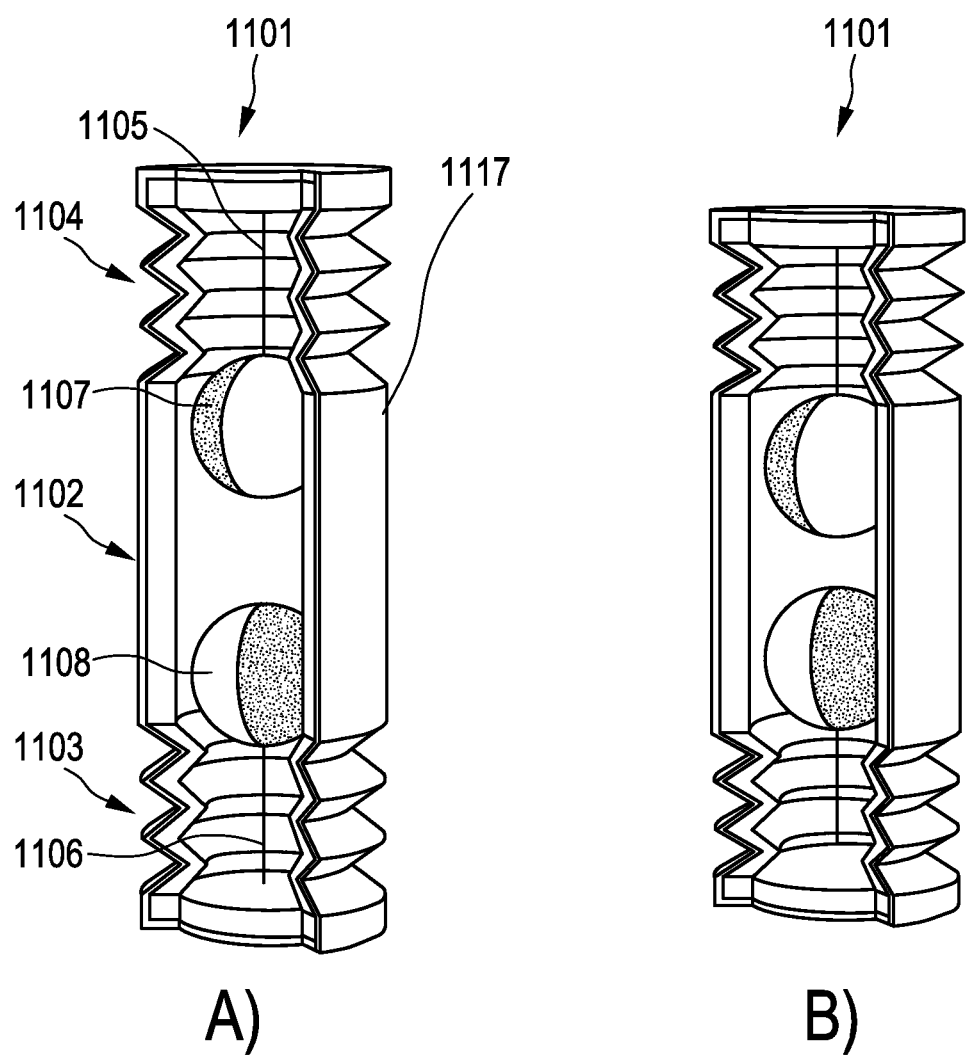
FIG. 5 shows schematically and exemplarily further embodiments of a pressure sensor with a bellows.
Figure 5:
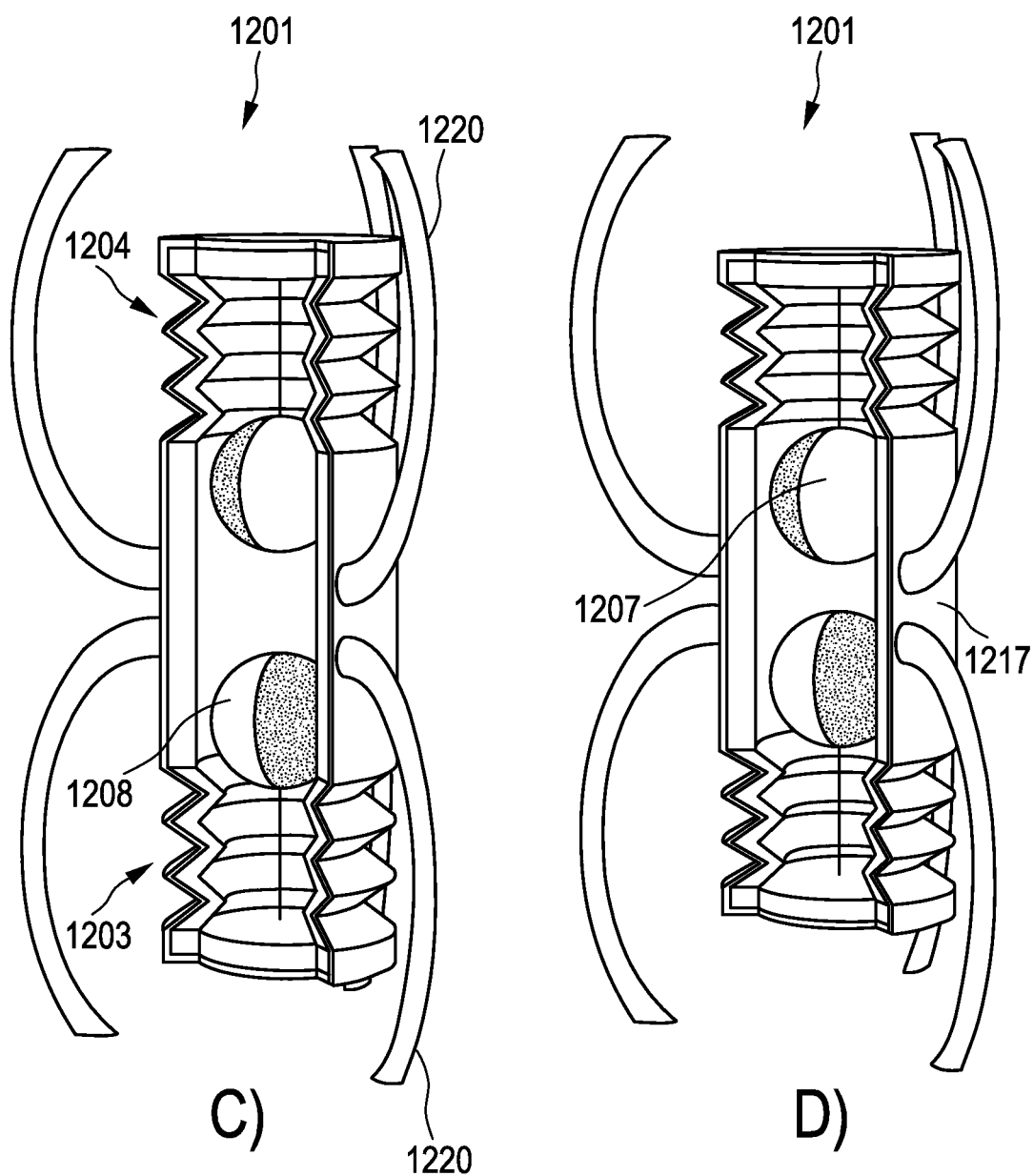

FIGS. 5A to 5D show schematically and exemplarily further embodiments of a pressure sensor. Here, a symmetric sensor design to minimize torque coupling to the environment is presented. In FIGS. 5A and 5B a symmetric sensor 1101 at low (FIG. 5A) and high (FIG. 5B) pressure is shown. The symmetric sensor 1101 comprises a cylindrical casing 1102, wherein at opposing ends of the casing 1102 bellows 1103, 1104 are located, i.e. end faces of the casing 1102 are held by the bellows 1103, 1104. To the end faces magnetic spheres 1107, 1108 are attached via respective filaments 1105, 1106, wherein the magnetic spheres are, as in the other embodiments, permanent magnets. The outer surface of the casing 1102 is provided with a thin metal coating 1117 acting as a diffusion barrier, i.e. the outer surface of the casing 1102 is provided with a diffusion blocking layer 1117. FIGS. 5C and 5D show a further embodiment 1201, which corresponds to the embodiment 1101, but in addition has a wire cage attachment 1220 to keep distance from vessel wall. For a final design, the open wire ends should be connected to avoid single wires from being caught by vessel structures during flow-based delivery. Thus, also in this embodiment a symmetric sensor design is present, in order to minimize torque coupling to the environment. In FIGS. 5C and 5D a symmetric sensor 1201 at low (FIG. 5C) and high (FIG. 5D) pressure is shown. The symmetric sensor 1201 comprises a cylindrical casing 1202, wherein at opposing ends of the casing 1202 bellows 1203, 1204 are located, i.e. end faces of the casing 1202 are held by the bellows 1203, 1204. To the end faces magnetic spheres 1207, 1208 are attached via respective filaments, wherein the magnetic spheres are, as in the other embodiments, permanent magnets. The outer surface of the casing 1202 is provided with a thin metal coating 1217 acting as a diffusion barrier, i.e. the outer surface of the casing 1202 is provided with a diffusion blocking layer 1217.

Figure 6:
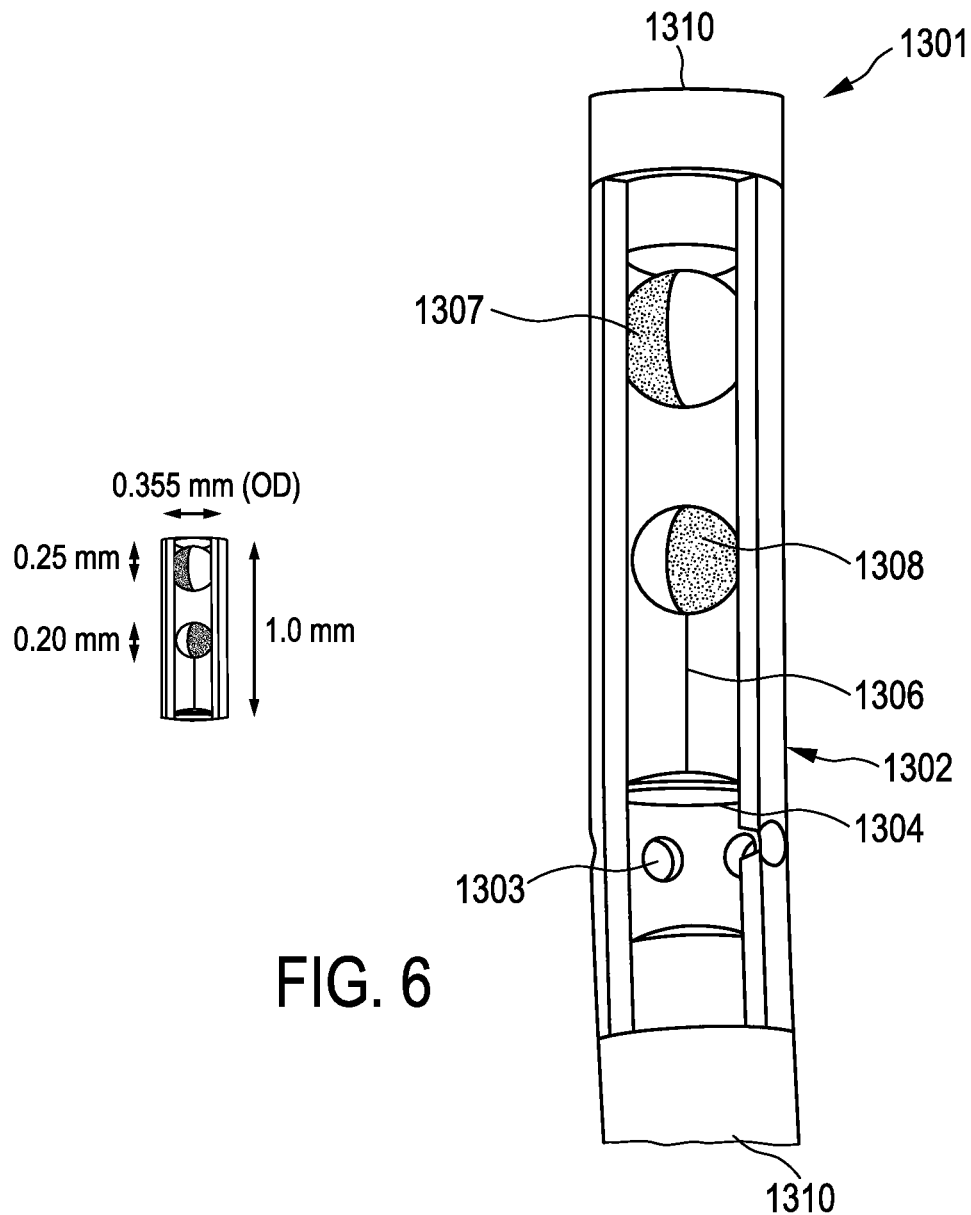
FIGS. 6 and 7 show schematically and exemplarily an embodiment of a guidewire with a pressure sensor.
Figure 7:
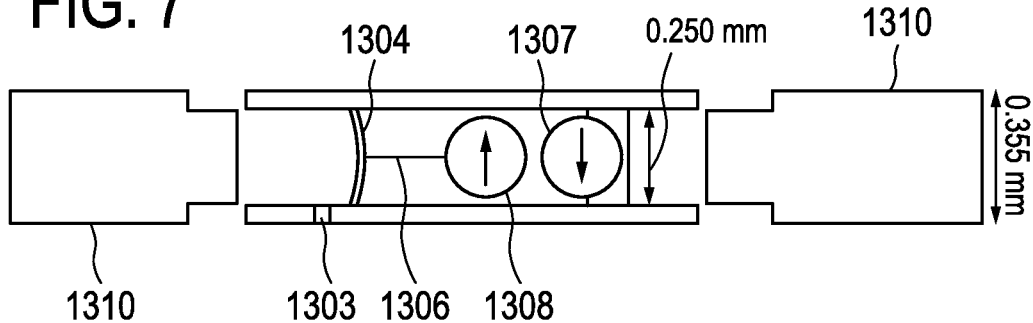

The pressure sensors described above can be integrated in, for instance, a guidewire 1310, as schematically and exemplarily shown in FIGS. 6 and 7. Ends of guidewire 1310 can be welded to a casing 1302 of the pressure sensor 1301 with a fixed magnetic sphere 1307 and a rotatable magnetic sphere 1308 attached to a membrane 1304 via a filament 1306. The casing 1302 comprises at least one opening 1303, which could be regarded as being ventilation ports, for providing a fluid connection to the outside of the casing 1302, in order to allow to measure the pressure. The dimensions shown in FIGS. 6 and 7 are only exemplarily. The dimensions could also be different. However, the shown dimensions are very suitable for fractional flow reserve pressure sensor application. Applying scaling laws to an observed demonstrator SNR shows that the indicated dimensions will give sufficient SNR and accuracy for remote operation at distances large enough to completely penetrate a patient. Thus, the pressure sensor can be integrated into a guidewire, thereby generating a pressure-wire.

Figure 8:
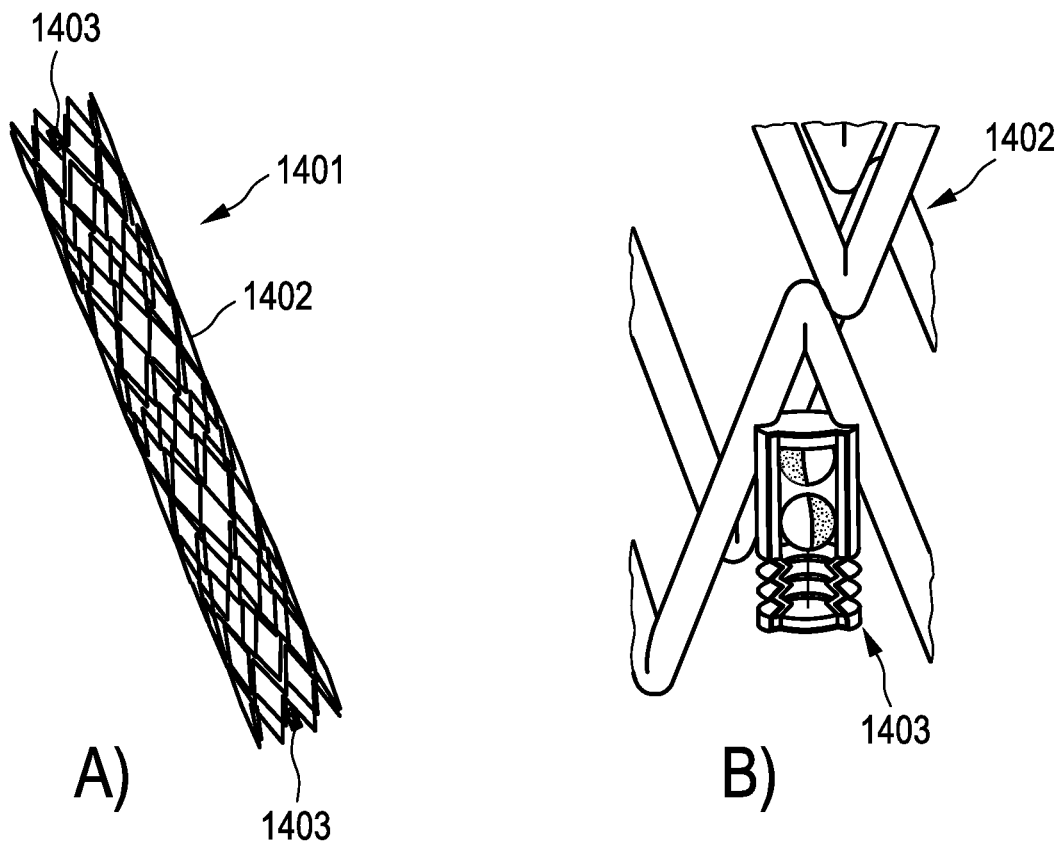
FIG. 8 shows schematically and exemplarily an embodiment of a stent with pressure sensors.

It may be useful to connect pressure sensors to other implantable devices (cf. FIG. 8), e.g. to monitor pressure drop over a stent 1401. This may be useful for characterization of pressure profiles in and around stents, e.g. to detect clogging or for monitoring of disease progression. FIG. 8 shows stent integration of pressure sensor 1403 with realistic size scale (stent length=30 mm, stent diameter=4 mm, wire diameter=0.2 mm, sensor length=1.2 mm, sensor diameter=0.5 mm), wherein FIG. 8A shows two sensors 1403 at the inlet and outlet of the stent 1402 which can be used to monitor pressure drop over the stent 1402 and thus potential clogging. FIG. 8B shows that the fixed part of the sensor 1403 needs to be connected to the wire frame 1402. Cover material could be added to give the sensor a more streamlined form for better integration into the stent (not shown). FIG. 8C shows a view into the stent 1402. The movable sensor part can be slightly tilted into the vessel to avoid or delay tissue overgrowth.

Applications are coronary stents, stents in aneurisms (pressure monitoring can help detect endo-leaks), transjugular intrahepatic portosystemic shunts (TIPS), or stents used in peripheral vascular disease. As above, a circular or disk shaped structure can act as the interface between device and sensor, with all attachment options mentioned above. A similar attachment can be applied to other in-body devices, e.g. wire coilings, shunt grafts, or transmural Amplatzer devices. For larger devices, such as guidewires, FFR pressure wires, catheters, large shunt grafts, or artificial heart valves, a hole can be drilled into the device to host the sensor. Inside the hole, again only one side of the sensor is attached, e.g. by glue or by clamping, while the other side is free to move, e.g. in a fluid or directly in blood. The fluid can either be of the non-mixing type, such as silicone oil or perfluorated polyvinyl ethers, or it can be separated from the blood by an additional thin and flexible membrane, or both.

All clinical applications make use of the fact that the sensor is passive and small. It can be placed inside the human body, while a readout system can detect it wirelessly without body contact from a distance. For most clinical monitoring applications, the sensor needs to be stable in the human body for several months to several years. However, for guidewires and catheters, stability only needs to be provided over a few hours. For a transvenously injected sensor, a stability over a few weeks could also suffice, as new sensors could be delivered from time to time.

Figure 9:
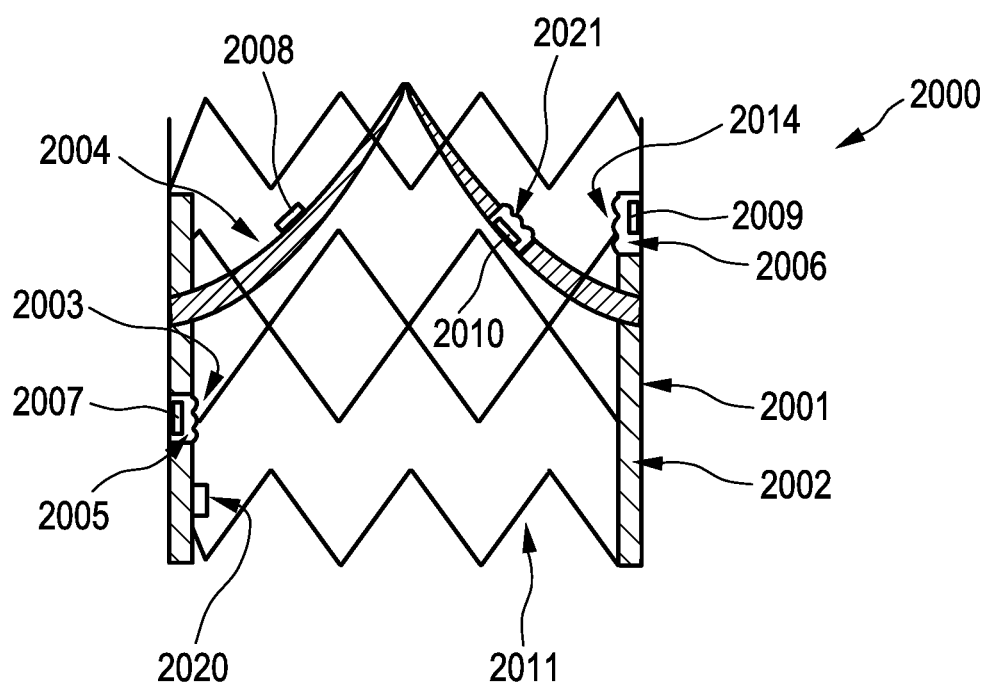
FIG. 9 shows schematically and exemplarily an embodiment of a heart valve with pressure sensors.

FIG. 9 shows schematically exemplarily an embodiment of a heart valve 2000 combined with a stent, wherein in FIG. 9 the stent material is denoted by reference sign 2011. The heart valve 2000 comprises a valve structure 2001 with a non-moving part 2002 and a moving part 2004. The heart valve 2000 comprises pressure sensors in accordance with the described embodiments. A first pressure sensor 2020 is arranged on a low pressure side of the non-moving part 2002 of the valve 2000. Moreover, a second pressure sensor 2008 is arranged on the moving part 2004 of the valve 2000. These two pressure sensors are attached to outer walls of the valve 2000. However, pressure sensors can also be integrated into the valve structure, wherein in this case there is a space within the valve structure covered by a membrane and filled with a fluid, wherein the respective pressure sensor is arranged within this space. Via the membrane and the fluid external pressure leads to pressure changes at the position of the respective pressure sensor within the respective cavity. In FIG. 9 a third pressure sensor 2007 is arranged within a cavity 2005 covered by a membrane 2003 at a low pressure side within the non-moving part of the valve 2000. A fourth pressure sensor 2010 is arranged in a space within the moving part 2004 of the valve 2000, wherein also this space is filled with a fluid and covered by a membrane 2021. A further pressure sensor 2009 can be arranged within a cavity 2006 of the non-moving part of the valve structure at a high pressure side, wherein also in this case the cavity is filled with a fluid and covered by a membrane 2014.

Figure 10:
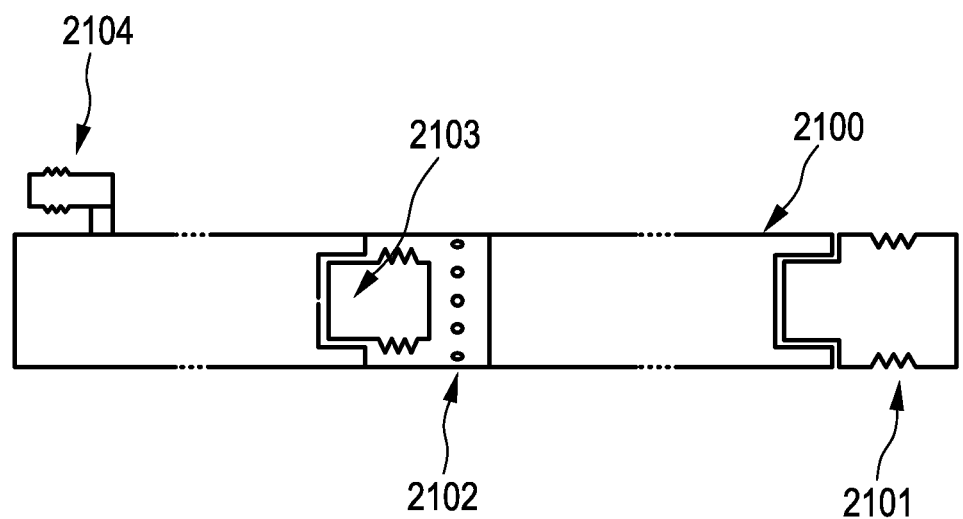
FIG. 10 shows schematically and exemplarily an embodiment of a wire for treating brain aneurism with pressure sensors.

FIG. 10 shows schematically and exemplarily an embodiment of a wire for treating of brain aneurism. The wire 2100 comprises pressure sensors in accordance with the described embodiments. In particular, a first pressure sensor 2104 can be arranged at a first end of the wire 2100 at one side of this first end. Moreover, a further pressure sensor 2101 can be attached to a second end of the wire 2100 and within an intermediate section of the wire 2100 a further pressure sensor 2103 can be mounted, wherein the wire 2100 can comprise an inner cavity in which the pressure sensor 2103 is arranged, wherein the inner cavity has a fluid connection to the outside of the wire 2100 via openings 2102.

Figure 11:
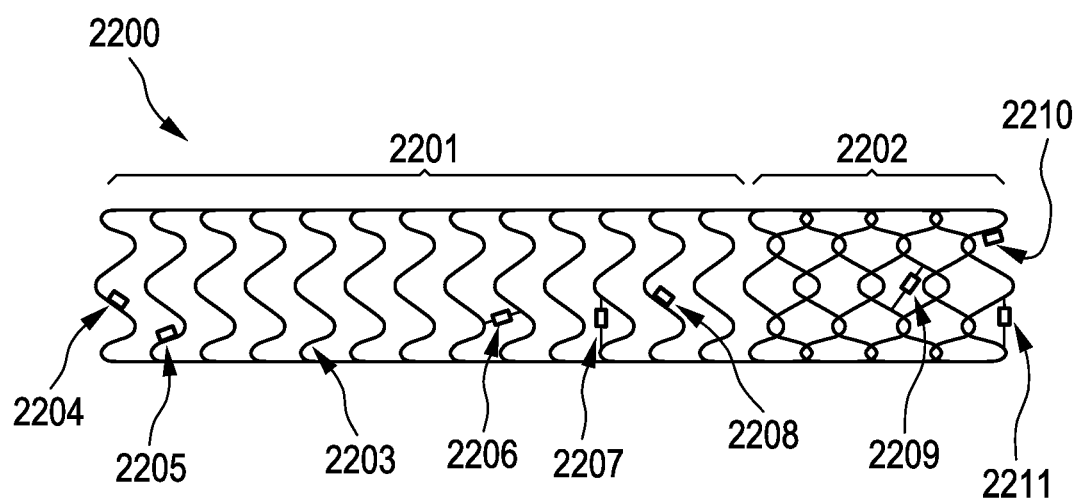
FIG. 11 shows schematically and exemplarily an embodiment of a hepatic shunt with pressure sensors.

FIG. 11 schematically and exemplarily shows an embodiment of a hepatic shunt device 2200 comprising a wire structure 2203. In this embodiment the wire structure 2203 has a first part 2201 surrounded by a lining material and a bare second part 2202. In this embodiment the first part 2201 is lined by using PTFE (polytetrafluoroethylene). Moreover, in this embodiment the first part 2201 of the wire structure has separate wires, whereas in the second part 2202 of the wire structure 2203 the wires are interwoven. The hepatic shunt device 2200, which might also just be named hepatic shunt, comprises several pressure sensors. For instance, a first pressure sensor 2204 is arranged next to a respective wire of the first part 2201 of the wire structure 2203 inside the PTFE tube. A second pressure sensor 2205 is arranged "in wire" within the PTFE tube, i.e. the pressure sensor 2205 is arranged between two ends of a respective wire of the wire structure 2203. A third pressure sensor 2206 is arranged between two neighboring wires of the wire structure 2203 within the PTFE tube and also connected to these wires. The wires of the wire structure 2203 have a wave-like shape, wherein a further pressure sensor 2207 is arranged between peaks or dips of the respective wave shape, wherein, for instance, a pressure sensor can be connected to two neighboring peaks or dips of the respective wave shape.

FIG. 11 shows a further pressure sensor 2208 next to a wire of the wire structure 2203 within the PTFE tube. Also the bare part 2202 of the wire structure 2203 can comprise pressure sensors. For instance, a pressure sensor 2209 can be arranged between two neighboring interwoven wires and connected to these neighboring interwoven wires. A further pressure sensor 2210 can be arranged next to a wire and a pressure sensor 2211 can be arranged between and connected to two peaks or dips of a wave shape of a respective wire of the wire structure 2203.

It should be noted that in FIGS. 8 to 11 the arrangements of the pressure sensors are only exemplarily, i.e. also more or less pressure sensors can be arranged at the same or other positions at or within the respective device. It is also possible that the respective device only comprises a single pressure sensor. The one or several pressure sensors of the respective device are pressure sensors in accordance with at least one of the described embodiments.

In the following, it is assumed that the sensor length is always about twice the diameter. All sensors with a diameter of 0.3 mm or larger will enable real-time pressure monitoring (more than 10 readings per second) at a distance of more than 30 cm with a pressure accuracy below 1 mbar and a pressure range of at least 400 mbar. These parameters enable the measurement of blood pressure with clinically relevant accuracy.

The sensor can be integrated into a guidewire, for instance, as explained above with reference to FIGS. 6 and 7. Typical guidewire diameters range between 0.33 and 1.0 mm, i.e. for a thin pressure wire, the sensor diameter should be about 0.3 mm or below. Thus, a sphere diameter of 0.25 mm would be feasible, leading to the above estimations on frequency, SNR, and Q factor. The theoretically achievable SNR of ~1000 at a distance of 30 cm would be sufficient for all readout situations. With large wire diameters, larger spheres can be employed, thus reducing the need for optimal background suppression. Thus, sensor diameters between 0.3 and 1.0 mm are useful for guidewire integration.

The sensor can also be integrated into a catheter. Here, when placing the sensor in the catheter lumen, the same argument as for the guidewire applies. It may be desired to place sensors in the material of the catheter wall, which would lead to stronger size constraints. It may be feasible to build a sensor with a sphere diameter of 0.1 mm, but the effort on background signal removal will go up and/or the distance at which the sensor can be reliably read out will be reduced. Alternatively, averaging synchronized with heart beat could be employed for SNR improvement, however, at the cost of temporal resolution. Thus, sensor diameters between 0.1 and 1.0 mm are useful for catheter integration.

A sensor could also be placed on a stent. To minimize effects on the blood flow through the stent, the sensor diameter should not be much larger than the wire diameter. Typical stent wire diameters are between 0.2 and 0.5 mm. Thus this would be a useful range for sensor diameters.

However, larger sensor could be integrated as well, optionally with an additional streamlined cover.

It is also possible to inject the sensor with syringe, wherein the sensor can be stuck into a smaller vessel in the pulmonary or hepatic areas without risk to the patient. Typical sensor diameters for injection would be between 0.3 and 1.0 mm. The cage size needs to be adjusted to the vessel diameter where the sensor should optimally be placed. Preferably the cage diameter would be larger than 1 mm, because in smaller vessels, the pressure may deviate from the desired pressure present in the larger feeding vessel. To simplify delivery through a needle into the venous system, the cage should be compressible in radial direction to diameter of the sensor housing.

Since the pressure sensor comprises a magnetic object like a permanent magnet, it can be problematic if the body should be scanned in an MRI scanner. The problem might not be a danger to the body, i.e. to the patient, because the pressure sensor is small and hence only small forces and torques are caused, that are not a threat to patients. Likewise an MR image generated by the MRI scanner might also not be spoiled because the pressure sensor is very small. However, high field strengths of more than 1.5 T are used in many clinical MRI scanners and the strong magnetic field might destroy the pressure sensor by changing the magnetization of the magnetic object or by damaging a mechanical arrangement within the pressure sensor. This will be described in more detail with reference to FIGS. 12 and 13.

Figure 12:
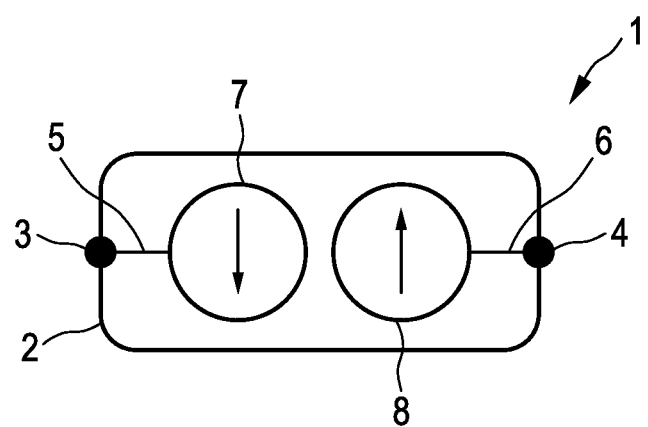
FIG. 12 shows schematically and exemplarily an embodiment of a pressure sensor.

FIG. 12 shows schematically and exemplarily a pressure sensor 1 without MRI field immunity. The pressure sensor 1 has two magnetic spheres 7, 8, both suspended by using a respective filament 5, 6 which is attached to the casing 2 at a respective attachment points 3, 4. When excited by an oscillating external magnetic field, the spheres 7, 8 begin a counter-rotational oscillation about the filament axis. This resonance oscillation produces a field that can be recorded from a distance. The casing 2 is partly flexible such that the distance between the two spheres 7, 8 and hence the resonance frequency changes depending on the external pressure. The flexible part of the casing 2 is not highlighted in FIG. 12 for clarity reasons.

Figure 13:
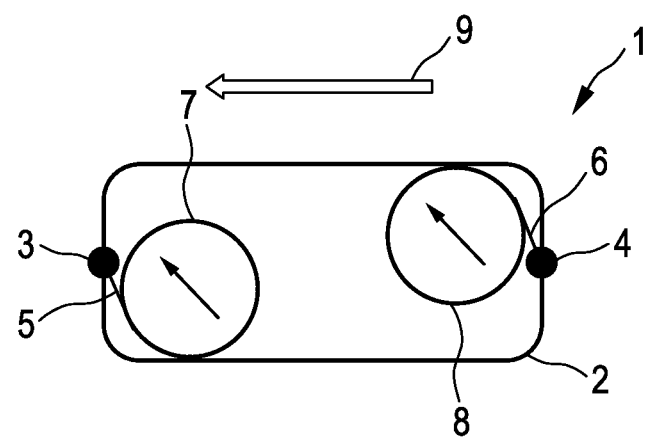
FIG. 13 shows schematically and exemplarily the embodiment of FIG. 1 in a situation with a high external magnetic field.

In FIG. 13, the pressure sensor 1 of FIG. 12 is brought into a strong magnetic field in axial direction 9. This forces the spheres 7, 8 to orient themselves in the direction of the magnetic field. However, in this implementation, the filaments 5, 6 are too short to fully align the spheres 7, 8. If the sensor casing 2 cannot move, either the filaments 5, 6 snap or, given the very strong magnetic field of high-field MRI scanners, the spheres 7, 8 change their magnetization direction rendering the device 1 nonoperational.

Figure 14:
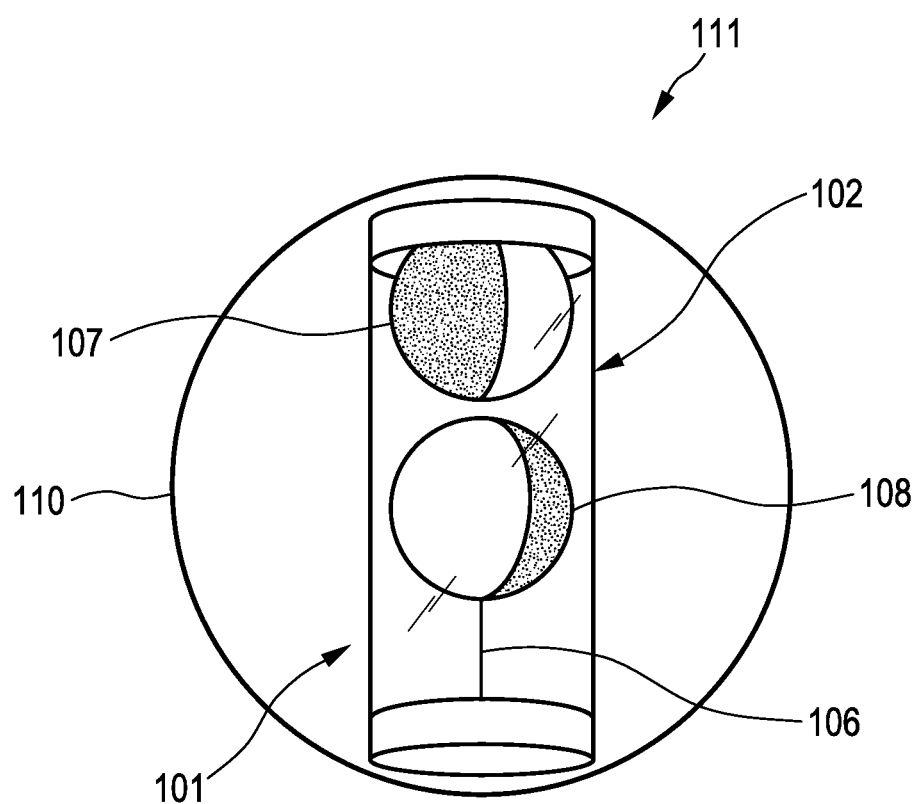
FIG. 14 shows an embodiment of a pressure sensor with a spherical outer housing.

One solution to this problem is to place the casing of the pressure sensor in an outer housing casing 10, 110, which is preferentially a spherical or ellipsoidal housing, e.g. filled with highly viscous fluid, so that the whole casing with the spheres can reorient to align the spheres' magnetization with the external field and thus avoid remagnetization. A spherical outer casing 110 allows for arbitrary reorientation of the sensor and thus can also be used for a simpler sensor design with one sphere 107 fixed and the other sphere 108 oscillating on a filament 106, as schematically indicated in FIG. 14. In FIG. 14, the pressure sensor 111 is formed by using the simpler magneto-mechanical oscillator 101, which comprises a casing 102 having included the fixed sphere 107 and the other sphere 108 oscillatable on the filament 106, within the spherical outer housing 110. For the design shown in FIG. 13, depending on the length of the filaments 5, 6, a partial reorientation of the sensor 1 would suffice and the outer housing 10 could be more ellipsoidal, i.e. made smaller in one or two directions, as schematically indicated in FIG. 15 in which the pressure sensor is denoted by reference sign 11.

The pressure sensor is configured such that external pressure changes outside the enclosing housing are transferred to external pressure changes being externally of the casing and internally of the enclosing housing. For instance, the outer housing can be a very soft housing filled with fluid or a housing with openings, in order to effectively transduce external pressure changes to changes of the mechanical oscillation of the magnetic object.

Figure 15:
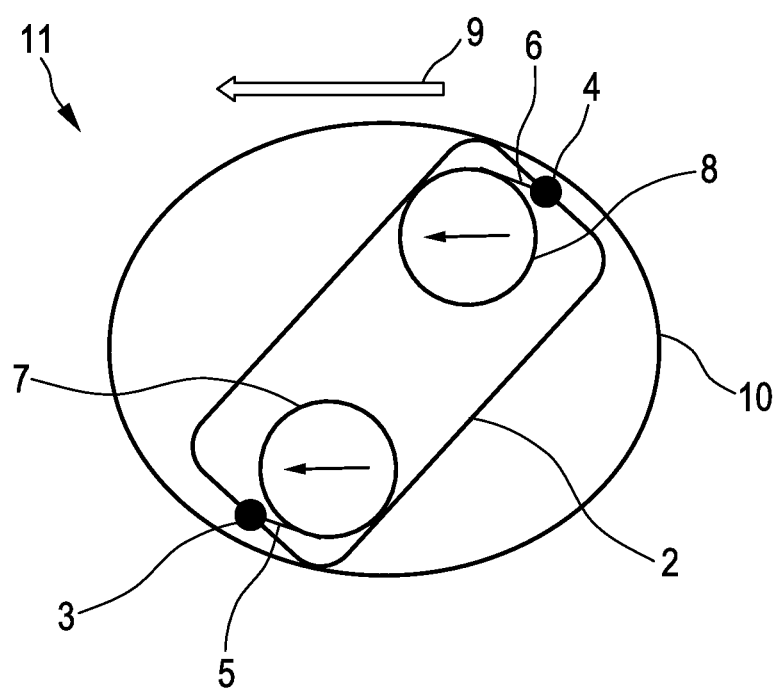
FIG. 15 shows schematically and exemplarily an embodiment of a pressure sensor with an elliptical outer housing.

The additional housing 10, 110 enables reorientation of the casing 2, 102 to align sphere magnetizations with the external field, wherein FIG. 14 shows a spherical housing 10 enabling free sensor reorientation and is thus also suitable for designs with, for instance, a fixed magnetic sphere, and wherein in FIG. 15 the required tilting is possible within a casing 110 that is flattened in one or two directions, i.e. has a smaller diameter than the sphere 10 in FIG. 14. The elliptical casing 110 is especially usable for sensors with both spheres 7, 8 suspended on filaments 5, 6.

Figure 16:
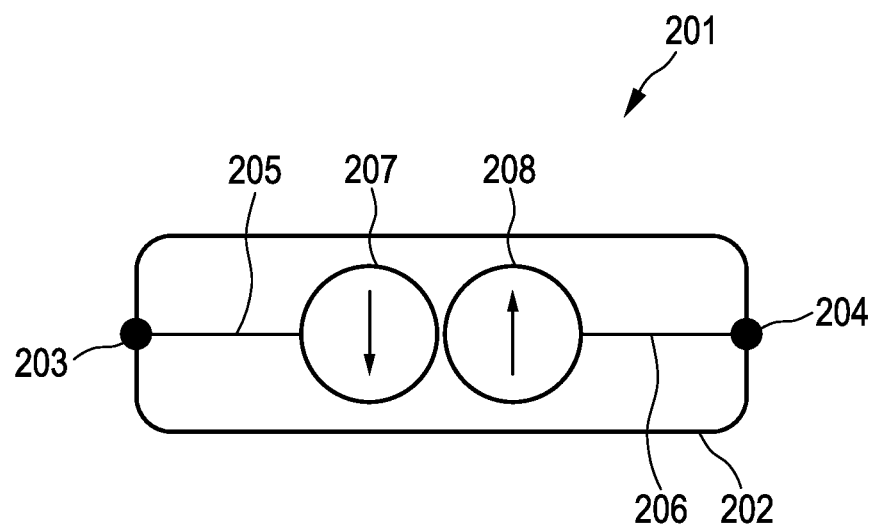
FIG. 16 shows schematically and exemplarily a further embodiment of a pressure sensor with relatively long filaments.

In FIG. 16, the pressure sensor 201 with the strings 205, 206, i.e. the filaments 205, 206, is elongated in comparison to the pressure sensor 1 shown in FIGS. 12 and 13, whereas the tube diameter is kept constant. So there is plenty of room for the spheres 207, 208 to align with an external magnetic field of arbitrary direction. The minimum string length is Pi/4 the diameter of the sphere 207, 208. The only problem that could arise is that the field is changed in a way to spool the filament 205, 206 around the sphere(s) 207, 208. To make this unlikely, the spheres 207, 208 and the inside of the casing 202 can be coated with a slippery non-sticking material like graphite. The filaments 205, 206 are attached to the casing 202 at attachment points 203, 204.

Figure 17:
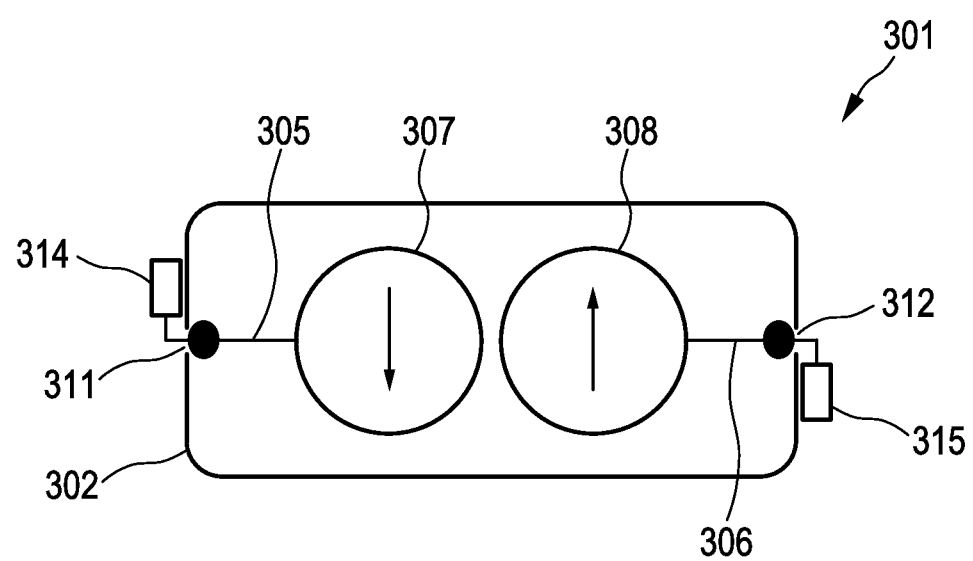
FIG. 17 shows schematically and exemplarily an embodiment of the sensing device with spooling units and stoppers.

In FIG. 17, which schematically and exemplarily shows another embodiment, the strings 305, 306, i.e. the filaments, of the pressure sensor 301 are by themselves too short to make the device MRI tolerant. However, a respective spooling unit 314, 315 is attached to the respective string 305, 306 and to the casing 302. If the forces on the respective filament 305, 306 become too large, this unit 314, 315 releases more length of the filament 305, 306. Therefore, the respective sphere 307, 308 can rotate freely and the problem is solved. For normal operation outside the field of an MRI machine, the length of the filament 305, 306 needs to be defined precisely. This is done by a stopper 311, 312 that can be attached to the string 305, 306, or by some sort of stopper in the spooling unit.

Figure 18:
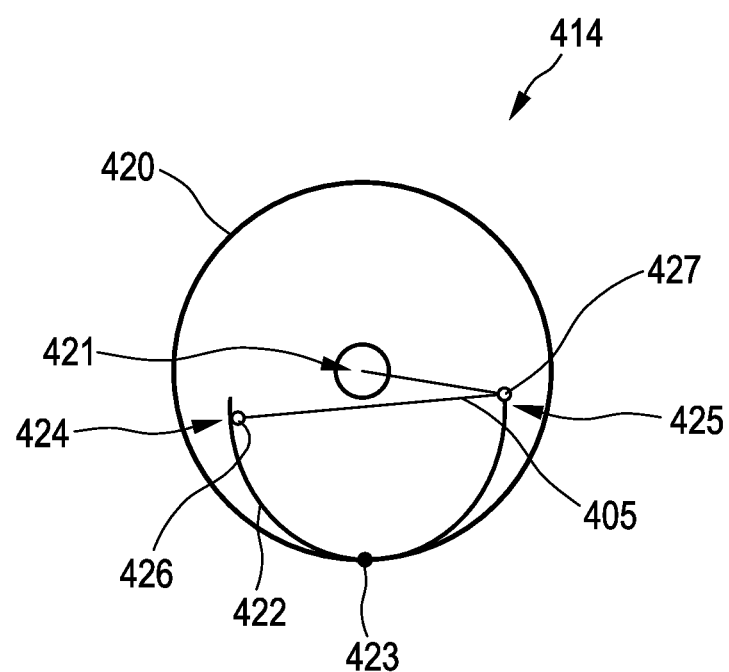
FIG. 18 shows schematically and exemplarily an embodiment of a spooling unit.

In FIG. 18, one possible spooling unit 414 is shown. It comprises a spring material 422 that holds the filament 405 by a pulley 427 and an attachment point 426. When the force on the filament 405 is low, the spring 422 is stopped by some stoppers 424, 425. The spring 422 presses against the stoppers 424, 425 and hence the length of the filament 405 is fixed. If the force gets higher, the spring material 422 is bent and the available length inside the case 420 increased. This construction preferentially allows for up to 1.5 sphere radii of filament elongation. This means it is sufficient regardless of the filament length inside the case 420. The filament 405 is guided out of the case 420 into the casing of the sensing device through a case opening 421. The spring is attached to the case 420 at a spring attachment point 423.

The described pressure sensors are preferentially configured to compensate a dependence of the resonance frequency on the temperature. This configuration of the pressure sensors for compensating temperature-based shifts of the resonance frequency will in the following be described with reference to FIG. 19.

Figure 19:
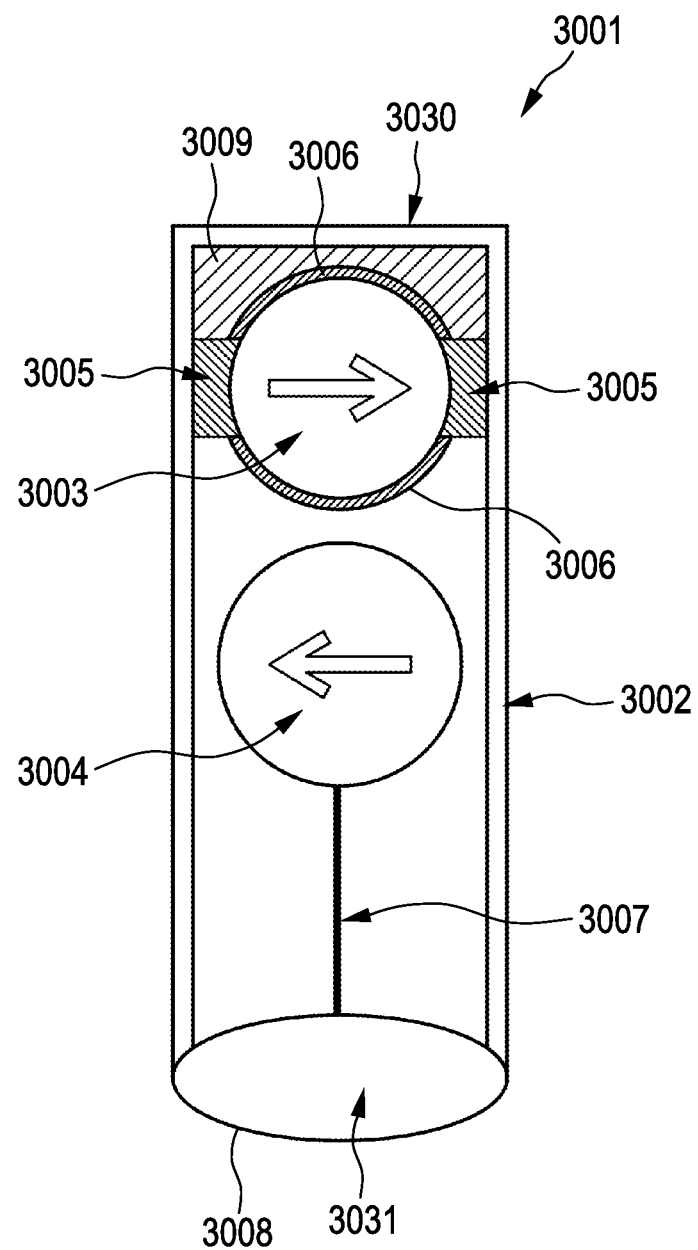
FIG. 19 shows schematically and exemplarily an embodiment of a pressure sensor with temperature compensation.

Also in FIG. 19 the pressure sensor 3001 comprises a casing 3002 and a magnetic object 3004 being arranged within the casing 3002 such that it is rotatable out of an equilibrium orientation if an external magnetic torque is acting on the magnetic object 3004. The pressure sensor 3001 further comprises a restoring torque unit 3003 being adapted to provide a restoring torque to force the magnetic object 3004 back into the equilibrium orientation if an external magnetic force has rotated the magnetic object 3004 out of the equilibrium orientation, in order to allow for a rotational oscillation of the magnetic object 3004 excited by the external magnetic torque. In this embodiment the casing 3002 is cylindrical and the magnetic object 3004 is rotatable around a virtual rotational axis centrally traversing the magnetic object 3004, wherein the magnetic object 3004 is rotationally symmetric with respect to the virtual rotational axis. In particular, in this embodiment the magnetic object 3004 is a magnetic sphere.

The restoring torque unit 3003 comprises a further magnetic object 3003 for providing the restoring torque. In particular, the magnetic object 3004 is attached to one end of a filament 3007, wherein another end of the filament 3007 is attached to the casing 3002. The filament 3007 is adapted to prevent the magnetic object 3004 from touching the further magnetic object 3003 due to their magnetic attraction and to allow the magnetic object 3004 to rotationally oscillate. In this embodiment the further magnetic object 3003 is stationarily attached to the casing 3002 by using glue 3009.

The magnetic object 3004 forms a first magnetic dipole, the further magnetic object 3003 forms a second magnetic dipole and the magnetic object 3004 and the further magnetic 3003 are arranged such that in the equilibrium orientation the first and second dipoles point in opposite direction. The first magnetic object 3004 and the second magnetic object 3003 are permanent magnets, wherein in the equilibrium orientation a north pole of the magnetic object 3004 faces a south pole of the further magnetic object 3003 and vice versa.

The casing 3002 is cylindrical, wherein the cylindrical casing 3002 comprises two end surfaces 3030, 3031 and wherein the further magnetic object 3003 is stationarily attached to a first end surface 3030 and the end of the filament 3007, which is opposite to the end attached to the magnetic object 3004, is attached to a second end surface 3031 of the cylindrical casing 3002.

In this embodiment the second end surface 3031 of the casing 3002 is formed by a flexible part 3008 of the wall of the casing 3002, wherein the magnetic object 3004 is attached to the flexible part 3008 via the filament 3007 such that external pressure acting against the flexible part 3008 from the outside of the casing 3002 leads to a change of the distance between the magnetic object 3004 and the further magnetic object 3003. Due to this distance change caused by the external pressure the strength of the magnetic field generated by the further magnetic object 3003 at the position of the magnetic object 3004 and hence the resonant frequency changes. Thus, the resonant frequency changes depending on the external pressure such that the pressure sensor 3001 can be used for measuring the external pressure as the other physical quantity. The flexible part 3008 of the wall of the casing 3002 can therefore be regarded as being a measurement element which is adapted to modify the resonance frequency depending on the external pressure.

The pressure sensor 3001 further comprises magnetic material 3005, 3006 arranged adjacent to the further magnetic object 3003. This magnetic material 3005, 3006 influences the magnetic field generated by the further magnetic object 3003, wherein the influence of the magnetic material 3005, 3006 depends on the temperature in order to change the strength of the magnetic field at the position of the magnetic object 3004 and hence in order to change the resonance frequency, if the temperature changes. The magnetic material 3005, 3006 is adapted such that its magnetization decreases with increasing temperature. Moreover, the magnetic material 3006 is adapted such that its magnetization direction is opposite to the magnetization direction of the further magnetic object 3003 and the magnetic material 3005 is adapted such that its magnetization direction and the magnetization direction of the further magnetic object 3003 are the same. The magnetic materials 3005, 3006, which are soft magnetic materials, therefore influence the resonance frequency depending on the temperature in opposite frequency directions, i.e. one of these magnetic materials leads to a change towards higher frequencies depending on an increasing temperature and the other of these magnetic materials leads to a change towards lower frequencies with increasing temperature.

The pressure sensor is preferentially configured such that the resonance frequency does not depend on the temperature. However, for instance, the flexible part 3008 of the wall of the casing, which might be formed by a membrane, might have a temperature-depended flexibility such that the resonance frequency might generally depend also on the temperature. Also further parts of the pressure sensor might depend on the temperature, wherein this dependence might also influence the resonance frequency. In order to compensate this unwanted temperature dependent frequency shift, the magnetic materials 3005, 3006 can be tailored such that they provide the same frequency shift in an opposite frequency direction depending on a temperature change. In particular, the magnetic materials 3005, 3006 can be chosen and arranged such that any temperature dependence of the resonance frequency of the pressure sensor 3001 is eliminated. It is also possible that only one of the magnetic materials, i.e. only a magnetic material decreasing the resonance frequency with increasing temperature or only a material increasing the resonance frequency with increasing temperature, is used for reducing or even eliminating the temperature dependence of the resonant frequency of the pressure sensor 3001. One or both of the magnetic materials 3005, 3006 could be regarded as being compensation elements for compensating the temperature-induced shift of the resonance frequency.

Figure 20:
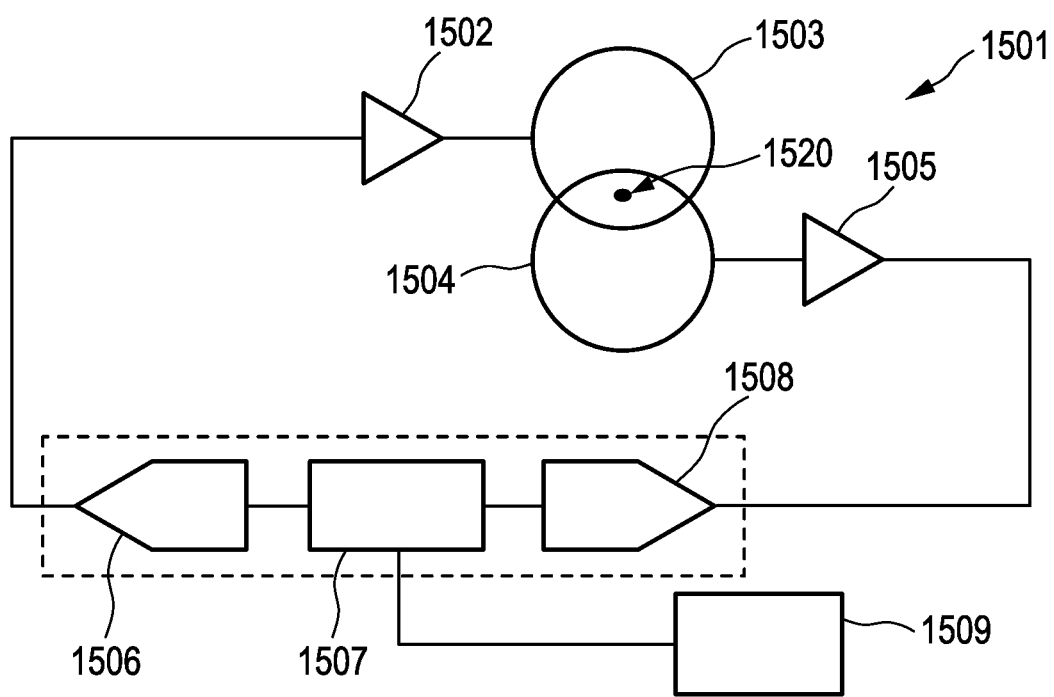
FIGS. 20 and 21 show schematically and exemplarily a detection system for reading out a resonance frequency of a sensor.
Figure 21:
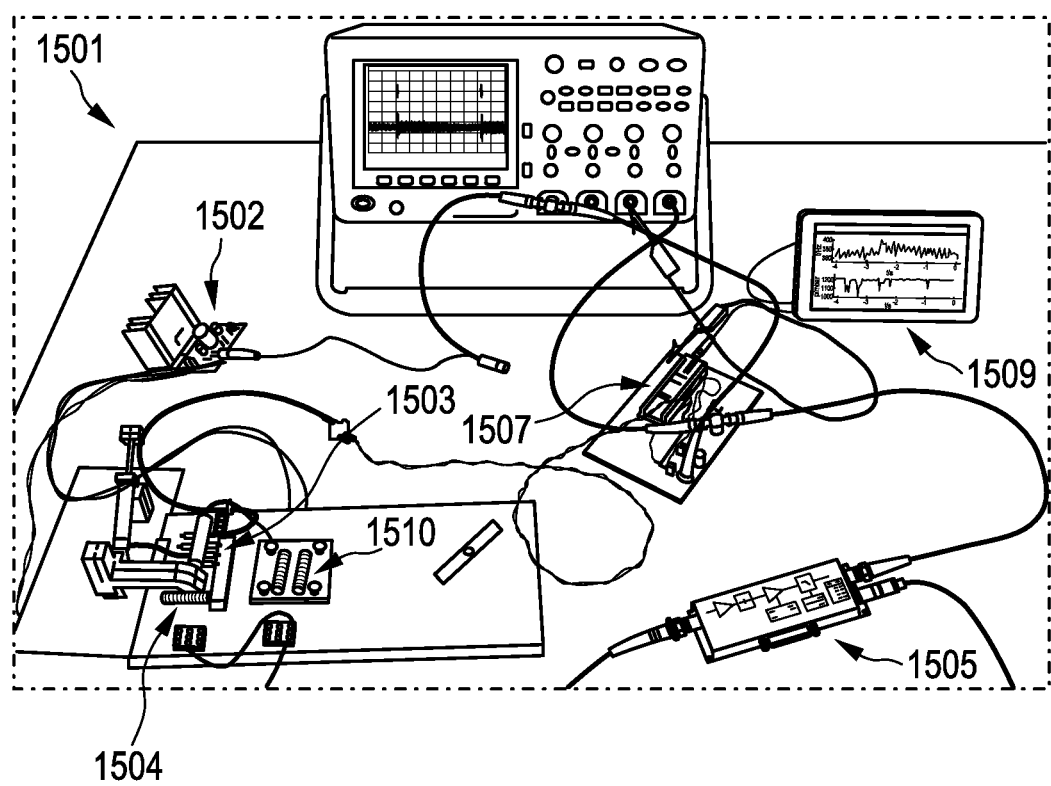

FIG. 20 schematically and exemplarily illustrates a detection system 1501 for detecting the resonance frequency of the respective sensor, for reading out a respective sensor, i.e. a reading system for wirelessly reading out the respective pressure sensor. FIG. 21 shows exemplarily a prototype of the detection system 1501. The detection system 1501 comprises basically at least one field generator of magnetic fields and at least one sensor of magnetic fields, i.e. a transducer for transducing a magnetic or electromagnetic field generated by the induced oscillations of the magnetic object of the pressure sensor into electrical response signals. The operation frequency band is in the low kHz range and has to be broad enough to cover the responses of several sensors operating in parallel at different frequencies, and possibly also higher harmonics of the sensor resonance frequency as well, e.g. to improve SNR. The transmit field amplitudes are at maximum a few milli-tesla, whereas field amplitudes to be detected are between 1/10 of a nT and several nT. Many different field generators may work (oscillating permanent magnets, coils with cores/without cores, magnetostrictive field modulators, . . . ) as well as many different magnetometers (Hall effect, various kinds of magneto-resistive sensors, magneto-resonance sensors, SQUIDS, etc.). The technical simplest systems are coreless conductor loops for sending and receiving of magnetic fields. Coils are generally good enough for the sensor application. The coil for generating the magnetic field can be also used for receiving the magnetic field. However, different coils can be employed for these tasks, which gives some advantage. FIGS. 20 and 21 show a detection system being a single channel transmit receive system, wherein many channels could be operated in parallel to obtain spatial information.

In FIG. 20 the detection system 1501 comprises a transmit coil 1503 which is connected to a microcontroller 1507 via a digital-to-analog converter 1506 (DAC) and an audio amplifier 1502 for generating the external magnetic torque for the pressure sensor 1520 which can be any of the described pressure sensors. A receive coil 1504 is also connected to the microcontroller 1507 via a low noise amplifier 1505 and an analog-to-digital converter 1508 (ADC) for reading out the resonance frequency. The microcontroller 1507 is connected to a display computer 1509. The microcontroller 1507 is configured for, for instance, signal generation and reception, frequency evaluation and control and optionally reference pressure measurements. In FIG. 21 also a transmit/receive decoupler is shown.

Figure 22:
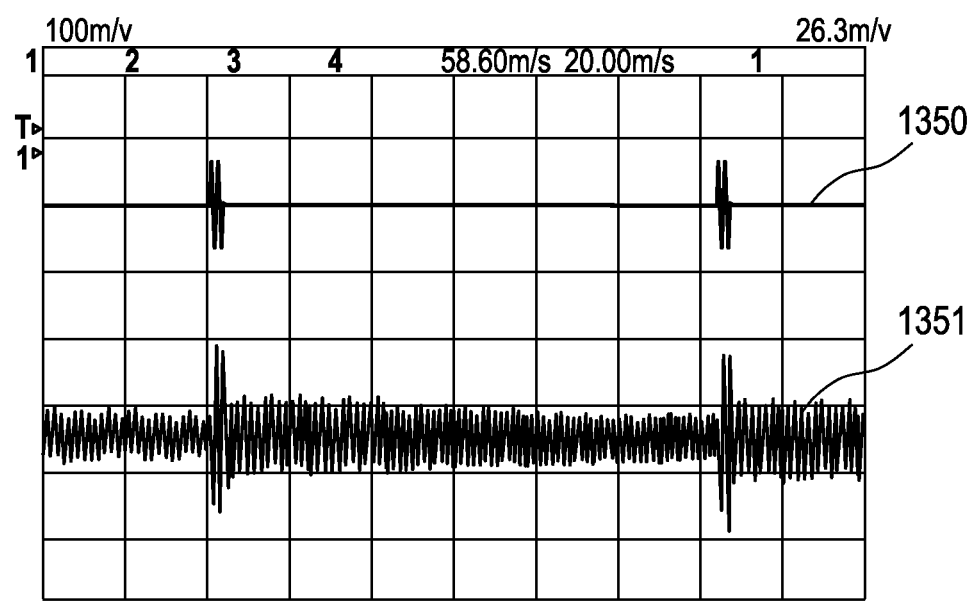
FIG. 22 shows schematically and exemplarily excitation pulses and resulting induced voltages.

The microcontroller 1507 generates transmit pulses (cf. upper trace 1350 in FIG. 22) that are amplified using the audio amplifier 1502 and then passed to the transmit coil 1503 which can also be named excitation coil. In this implementation, a separate receive coil 1504 is employed, which is decoupled from the transmit coil 1503 using two additional decoupling coils 1510 which are not shown in FIG. 20 for clarity reasons. The receive signal is fed into the low-noise amplifier 1505 and passed to the ADC 1508 of the microcontroller 1507, where a time trace of typically 1/20 of a second is sampled at a rate of about 20 kS/s. FIG. 22 shows, besides the transmit pulses 1350, which could also be named excitation pulses, the induced voltage 1351 in the receive coil 1504 due to sphere oscillation in the sensor and hence due to sensor response. The spacing of the excitation pulses 1350 might be continuously adjusted by the microcontroller 1507.

In the following advantages of a multi-coil system will be discussed. With a single coil system, the relative sensor to coil orientation may be such that the coil cannot drive the magnetic sphere oscillation and also cannot read back the generated field variation. So, to avoid the need for a user to reorient the readout system with respect to the sensor, a multi-element coil system can be desirable. The coils should have different spatial sensitivity distributions to be able to generate the optimal excitation field vector in all situations. The use of several coils furthermore enables localization of the sensor by determination of position and orientation of the oscillating magnetic dipole in space. The different amplitudes of the receive signals together with the known coil element sensitivities can be matched to a dipole model for determination of the position and orientation parameters. An example of a multi-coil system for implementation in a pillow or mattress is displayed in FIG. 23. With many receive coils and channels available, the additional information can also be used for improving background signal suppression as described further below.

Figure 23:
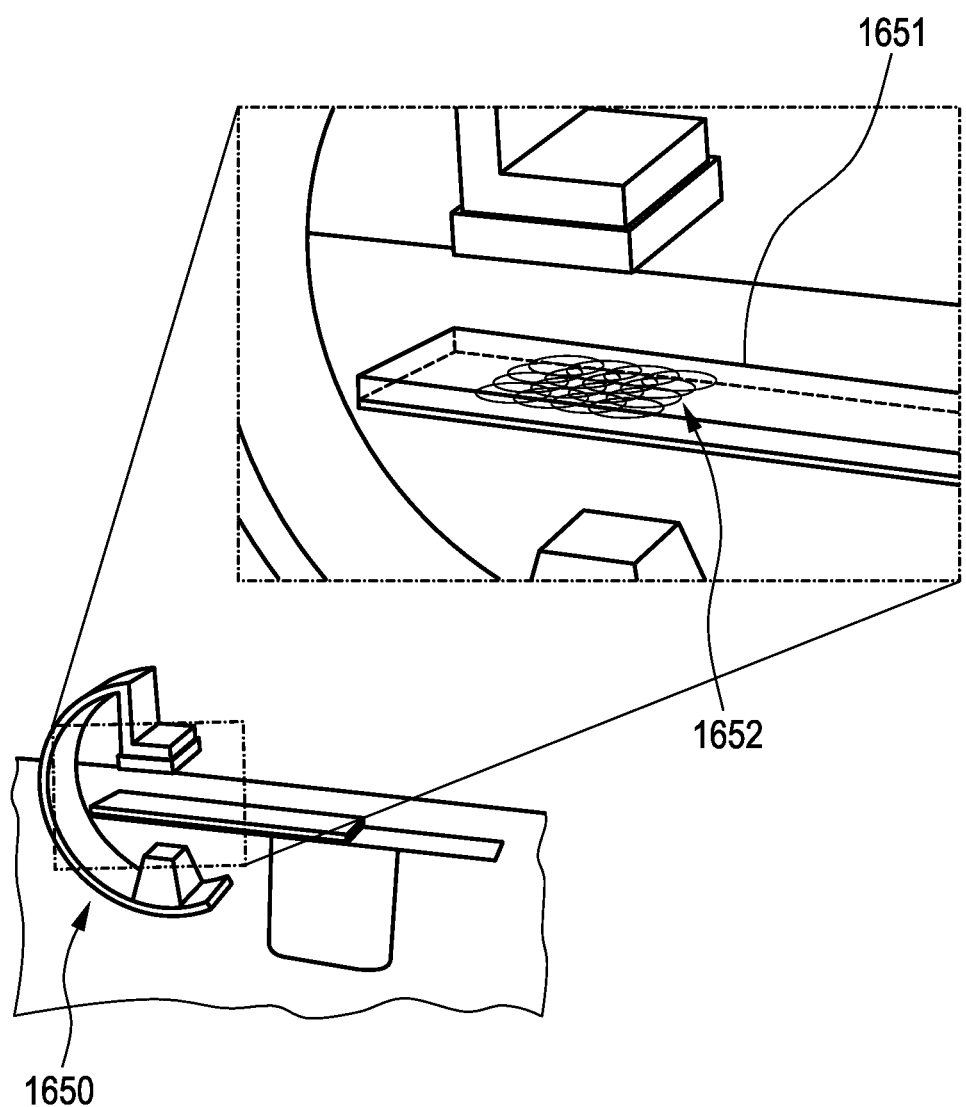
FIG. 23 shows schematically and exemplarily a multi-coil array integrated in a mattress of a patient bed of an imaging system.

In FIG. 23 the several coils 1652 form a multi-coil array which is integrated in a mattress 1651 of a patient bed of an imaging system 1650 like a C-arm system. The coils 1652 are preferentially aluminum coils having an x-ray absorption of less than 10 percent. It is therefore not required to increase the patient dose, if the coils 1652 are used.

In the following the coil-based transmit system of the detection system will be exemplarily described in more detail. The coil based send system comprises the send amplifier and the send coil. Optionally there is also a matching circuit and a "mute" circuit involved. As the send signal shape is not very critical in the sensor application, a multitude of amplifiers are suitable for the task (Class A, Class B, Class AB, Class D, etc., employing transistors, vacuum tubes, thyristors, and many more components). As the signal quality is not critical, the amplifier topology with the lowest loss can be selected, which is a half or full bridge amplifier employing switches with low on-resistance. The preferred switches are MOSFETs or IGBTs. The matching circuit is in the simplest case a simple capacitor in series to the inductor. Provided the amplifier operates with sufficient supply voltage, such a matching capacitor may be omitted or the capacitance may be chosen so high that the resonance frequency of coil with capacitor is well below the operation frequency. The matching circuit is of interest for another reason. Medical equipment should operate always in a safe way and reducing voltages is of concern. By placing the capacitor in the middle of the coil, so that the current flows through one coil section, then through the matching capacitor, and afterwards to the second coil section, the peak voltage differences can be reduced. This is even more true, if the coil is split into more sections each connected with the appropriate capacitor. This makes the coil and matching circuit to a combined unit. The field amplitude is conveniently controlled by a pulse width modulation, i.e. the amplifier increases/decreases the current through the coil only for a fraction of the cycle or alternates rapidly between increasing/decreasing of the current. As the exact signal shape is less relevant for the sensor application, it is best achieved by only changing state 2 times within a half wave (or 1 time in case of full power where the pulse length is identical to the half wave length). Ideally, the amplifier has not only the possibility of increasing or decreasing the current but also to keep the current more or less constant or at the level the matching circuit dictates. This is achieved by a proper switching sequence of the transistors in the half or full bridge. Generally, the supply voltage of the amplifier should be rather low and lie in the range below 50 V. In addition, the matching circuit should be set-up in a way to not exceed this 50 V limit at any two points. It is even better not to exceed 24 V in both cases. This means that the number of windings should be kept low. However, peak operation currents should exceed 10 A, better 100 A.

In the following a send/receive insulation will be described. It is essential that not too much noise from the send system, i.e. from the field generator, couples into the receive system, i.e. into the transducer for transducing the magnetic or electromagnetic field generated by the induced mechanical oscillations of the magnetic object of the pressure sensor into electrical response signals, while the send system is not in the send mode, i.e. no excitation field is generated. In addition, the send amplifier should not short the receive signal or even partially reduce it. There are several possibilities to achieve this. If we have different send and receive coils, the two coils could be decoupled geometrically (cf. FIG. 24).

Figure 24:
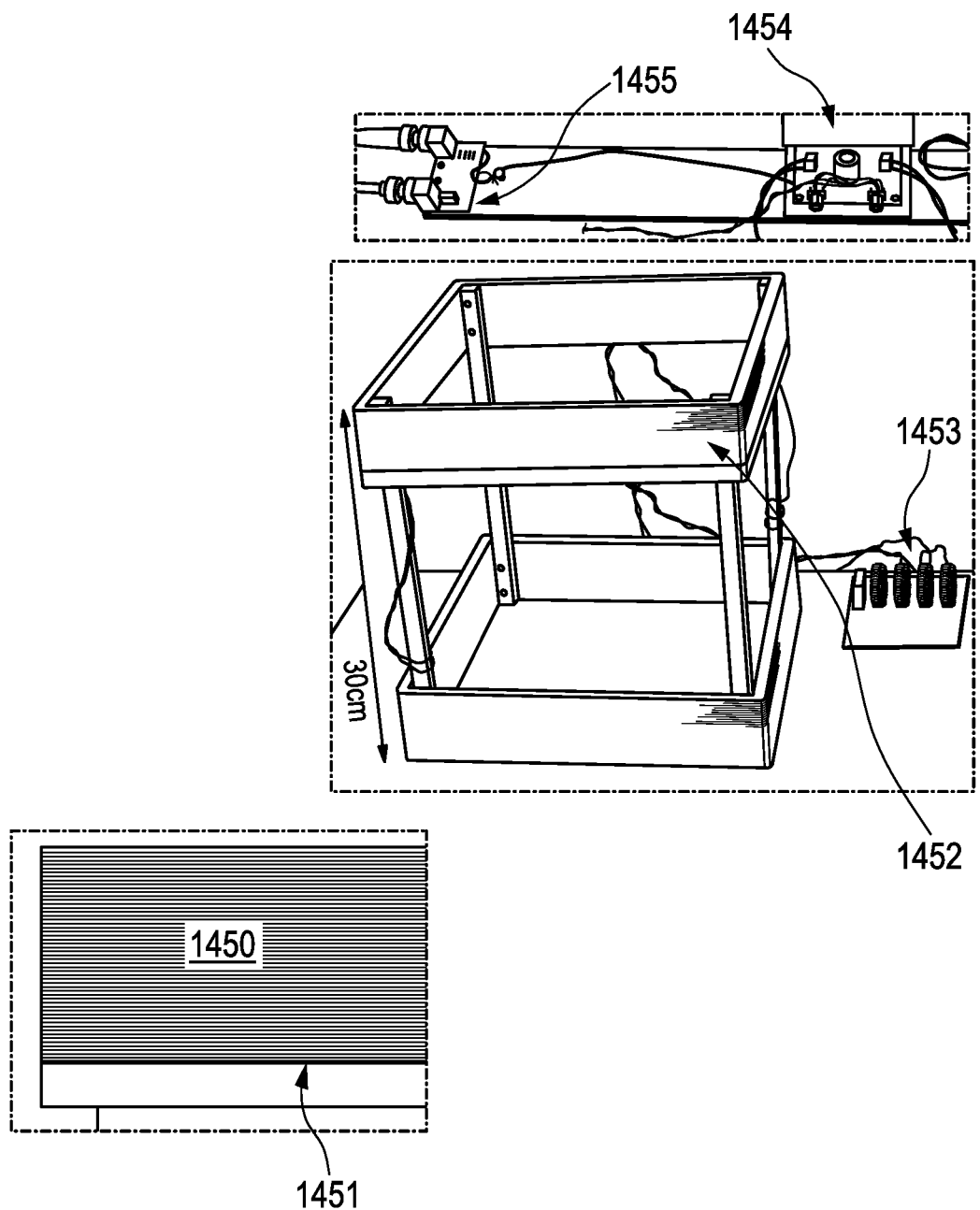
FIG. 24 illustrates schematically and exemplarily coils of the detection system.

FIG. 24 shows an implementation of a gradiometric receive coil design for suppression of transmit and background signal in receive path. Here large coils 1452 have been chosen, which enabled reading out the sensor up to distances of about 30 cm above the upper coil. The gradiometric design uses the geometric decoupling method: the transmit coil loops 1451 are connected to produce parallel fields, whereas the receive coil loops 1450 are connected to receive field gradients and suppress homogeneous fields. This transmit and receive system provides an intrinsic geometric decoupling by using parallel transmit loops and anti-parallel receive loops, wherein this might be named gradiometer configuration. This leads to an intrinsic geometric coupling. This system with the air coils is highly linear. FIG. 24 also shows a DC block 1455 with an audio amplifier 1454, and a low pass transmit filter 1453. The lower part of FIG. 24 illustrates outer windings of the receive coil 1450 and inner windings of the transmit coil 1451.

In particular, in FIG. 24 the lower left image is a close-up of the middle portion of the upper coil assembly. In the lower left image, one can see actually only 1 turn of the send coil 1451 peeking out in the bottom. The rest is obscured by the receive coil, wound with a much thinner wire. The DC blocking circuit 1455 is just a signal conditioning in front of the audio amplifier as the signal for the audio amplifier may be generated by a simple PWM output. The low pass filter 1553 is a filter in between the output of the audio amplifier 1454 and the transmit coil 1451. It has two purposes. First avoiding the introduction of high frequency noise, second it is there to combine the two output channels of the audio amplifier into one.

A geometric decoupling is not always possible, especially if an array of senders and receivers is used. In this case a transformer can be introduced with terminals connected to the send circuit as well as to the receive circuit. This transformer provides the decoupling of the send and receive system. This transformer solution can be used even if a combined send/receive coil is used. The transformer may be substituted by a capacitive (or even resistive) decoupling network both with combined and separate send/receive coils. The drawback of the compensation methods is that they need quite some space, add noise and in the case of capacitive decoupling narrow the frequency operation range of the detection system. A more robust and cheaper solution is to add a circuit that completely mutes the send amplifier during receive times. For this, crossed diodes can be added to the output of the amplifier. Especially diodes with low capacitance at zero voltage like PIN-diodes are useful. This provides a high impedance if no current flows. To further augment this, an electronic switch can be placed at the output of the amplifier, shorting all residual noise signals while receiving. The diodes still provide the desired high impedance. It is also possible to construct a special amplifier that is totally noise free and provides a high impedance when not operating. With the half and full bridge designs, this can be achieved by having absolutely no switching operation in any component during receiving, the use of low output capacitance transistors, by having about half the supply voltage at the output(s) in receive mode, having no noise coming from input connectors (optical insulation), and having a highly filtered supply voltage (heavy filtering or no power supply switching during receive operation).

In the following the coil-based receive system of the detection system will be discussed. The receive amplifier should be of a low noise type. However, the requirements are not so high that uncommon receive transistors need to be used. Standard low noise bipolar or JFET silicon transistors are usually good enough. The only special features are that the amplifier needs to survive the send pulses and starts operation shortly after the send pulse. There are several ways to reach this goal. In the case of decoupled send/receive systems (including combined send/receive coil with decoupling network), the receive amplifier needs no special features to reach this goal. If no decoupling is present, the amplifier can be hardened to the send pulse. This can be done by adding a suitable capacitor to the input of the amplifier and crossed diodes to the second terminal. This provides a suitable high impedance in the send case and shorts all to high voltages to harmless levels for the amplifier. Naturally, the added capacitor needs to be rated to the maximum send voltage. The capacitance value needs to be so high, that the signal at the amplifier is not too much reduced in the receive case. For a JFET based amplifier, this is generally not a critical issue. The crossed diodes can be augmented or supplanted by a suitable electronic switch, like an optocoupler with MOSFET output. This has the advantage to further reduce the input voltage. If properly done, the receive amplifier will not be saturated and functions right after the send signal has declined sufficiently.

In the following the interface to the digital system will be discussed in more detail, wherein firstly the digital signal output and processing is described. Although an analog timer system could generate the output signals, usually a digital system, like a DSP or FPGA, will be used. Depending on the type of output amplifier different outputs may be used. For an analog amplifier, some type of ADC may be used. As the output signal quality is not very critical, a simple PWM type of analog output may be sufficient. Digital amplifiers are best interfaced using a digital output line. However, it is also possible to use an analog output for them and implement the switching pattern generator on the amplifier. With the best matching amplifier, the half or full bridge, it is most suitable to produce the switching pattern directly on the digital system. In addition, also the switching patterns for receive amplifier input protection and send amplifier output denoising may be generated directly by the digital system. The common feature to all the output options is, that they need to be fast enough to exactly keep phases over different excitations of a single sensor or between different sensors. So the output needs to have the possibility of switching updates on a raster finer than a $10^{th}$ of the full period time, better finer than a $100^{th}$ of the full period time. For a say 2 kHz sensor, this means updates on a raster finer than 220 kHz, even better 200 kHz. This does not mean that every time at the raster points switching state changes need to be possible. So it is for example possible to have a serial interface for each amplifier that transfers the new switching state to the amplifier and a protocol to execute this change at a certain time over the same serial interface. This is especially useful for the amplifier type that inherently goes silent during the receive phase. For this a 1 bit serial interface can be implemented which only needs a single optocoupler on the amplifier. This makes it easy to reach noise immunity from the digital send side, as the stray capacitance in a single optocoupler can be very low.

In the following the analog to digital interface will be discussed. The analog to digital conversion is fairly standard. As the signal is low bandwidth, at least if only a single sensor is used, it would be possible to mix the signal down to near DC and sample this signal. However, the sensor signal has a rather low frequency, usually below 10 kHz. Today, there are plenty of suitable ADC chips to sample this directly. Especially, as digital signal processing is crap in comparison to analog filters, it is best to use a heavily oversampling in the ADC. At least 10 times the sensor frequency should be used bit 100 or 1000 times are also valid choices. The high oversampling makes the design of the ADC input filter easy and cheap as only the sensor signal frequency needs to come through while above the Nyquist frequency no signal shall come through. However, a filtering below the sensor frequency is also useful to avoid the usual high background signals there. A high background signal may reduce the possible amplification prior to the ADC, increasing ADC noise contribution. The ADC noise (number of effective bits) and samples should match the needed dynamic range and noise expectations. This means, the ADC should not be in saturation while the maximum expected signal and all noise components are present. Simultaneously, the quantization noise of the ADC should be so low, that the overall noise is not increased. Here noise means all the unwanted components in the recorded signal stemming from real noise sources like the coils resistance or the receive amplifier behavior. It also includes the interference components that cannot be eliminated by suitable filtering and background signal subtraction. Usually, with modern ADC chips this requirement can be meat e.g. with 2 MS/s 18 Bit ADCs. For cost savings, it may be useful to employ an ADC with lower specifications but add a gain control to still reach good overall performance.

In the following the data processing will be discussed. Before data evaluation the raw ADC data have to be processed. As heavy oversampling is desired, a first processing step could be a decimation step. This has the main advantage to reduce the data size and therefore the needed computing power for further steps. Optionally the decimation step may include other filters i.e. a band pass around the expected signal frequency. This may simplify further processing steps and reduce the dynamic range of the signal which in turn may save computing power (variables with less bits). A further optional data processing step is to apply an inverse non-linear filter to reduce the non-linearity of the receive system. This means, the non-linearity of the full receive system is measured and a computational filter is constructed to reverse the effect of the non-linearity. This is especially useful if low cost components are used because they tend to have more non-linear behavior. This non-linear filter may alternatively be used as the first processing step. If more than one receive signal is used, there are further signal processing steps. If at least one receive channel is not detecting the sensor signal and thus provides a measure of the background signal, this (and all other such signals) are correlated with the receive signal and the correlating components are subtracted from the signal bearing channels. This subtraction can be done in time or frequency domain or a mixture of both. If there are no channels without sensor signal, a data processing strategy sometimes called "virtual gradiometer" can be used. This decomposes the multitude of channels in virtual channels that are linear combinations of the physical channels to minimize interference of signals not generated by the sensor. The factors for the linear combinations may be found by correlating the signals of the channels excluding the signal band of the sensors.

Moreover, in the following the data evaluation will be explained. As a pressure change on the sensor changes the distance between the magnetic spheres and thus the resonance frequency of the magneto-mechanical oscillator, frequency is the main parameter to be extracted from the acquired sensor signal. Due to the high quality-factor of the resonator (time constant up to seconds), the subsequent excitation pulses are typically played out before the oscillation has fully decayed (cf. FIG. 22) and thus need to have the correct phase and timing to amplify the existing oscillation. This requires real-time extraction of the frequency between subsequent excitations. The frequency can be extracted either using a comparison algorithm that minimizes the phase differences between the measured signal and pre-calculated time-traces spanning a range of frequencies or by Fourier analysis, which is the preferred method. High-resolution frequency information can be obtained by time-domain zero padding or frequency domain interpolation and subsequent localization of the resonance peak in the spectrum, either using a peak-finding or a curve fitting procedure. For further improvement of the frequency determination accuracy and reliability, the higher harmonics of the detected resonance signal can be incorporated into the evaluation (cf. spectrum in upper right of FIG. 25), e.g. using a weighted frequency estimation based on the several harmonics or by checking the consistency of the frequency determination between several harmonics.

Figure 25:
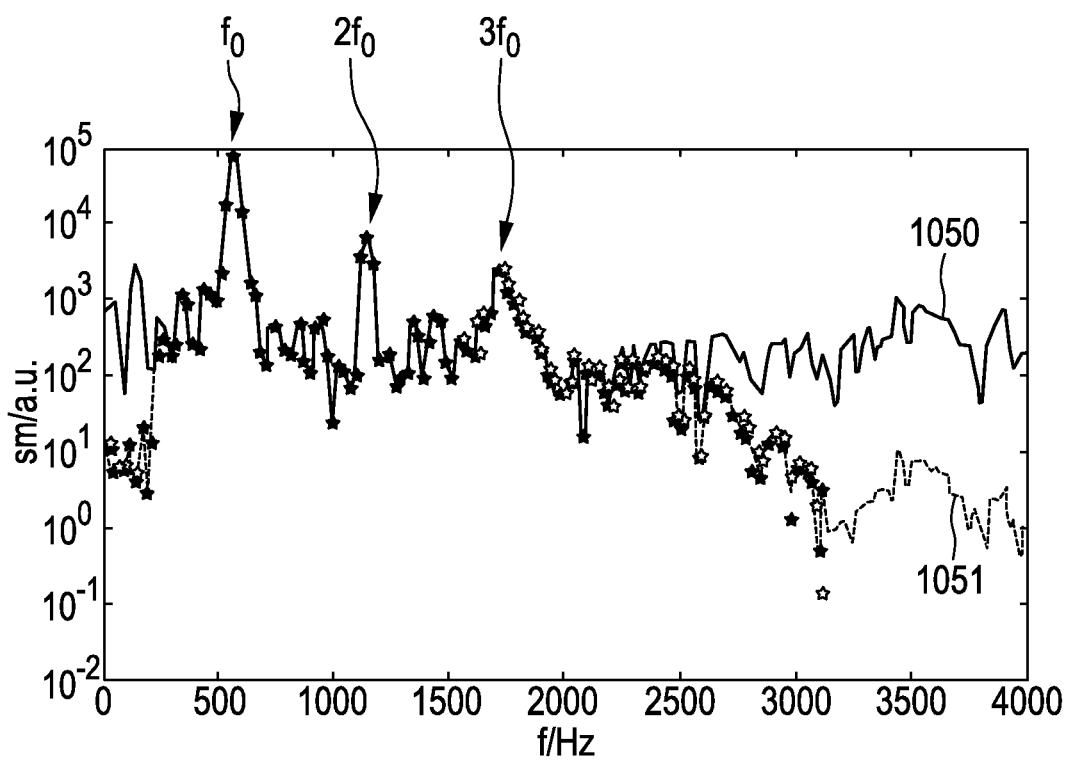
FIG. 25 shows a frequency spectrum used for determining the resonance frequency, FIG. 26 schematically and exemplarily shows an analog receive filter.

In the example, to which FIG. 25 refers, the signal of the second harmonics is an order of magnitude smaller than the base frequency signal. A better filtering is therefore required. Various filter stages can be used to optimize the signal at resonance frequency and higher harmonics thereof like analog excitation filters like DC block and low pass, analog receive filters like a band pass filters, and digital receive filters like IIR response filters for real time processing (sixth order Chebyshev type II). In FIG. 25 the center position of the f0 resonance peak is determined from the largest peak in the filtered spectrum. From f0, the timing of the next in-phase excitation pulses is calculated. The repetition frequency of the system is between 5 and 30 Hz, providing a real-time trace of the frequency response (cf. FIG. 32).

Figure 26:
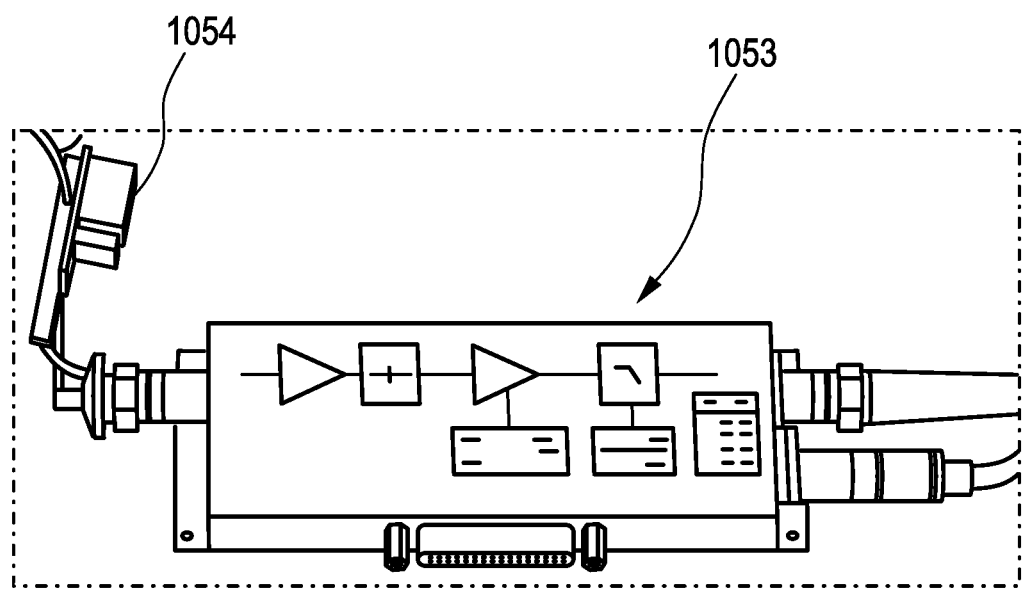
Figure 27:
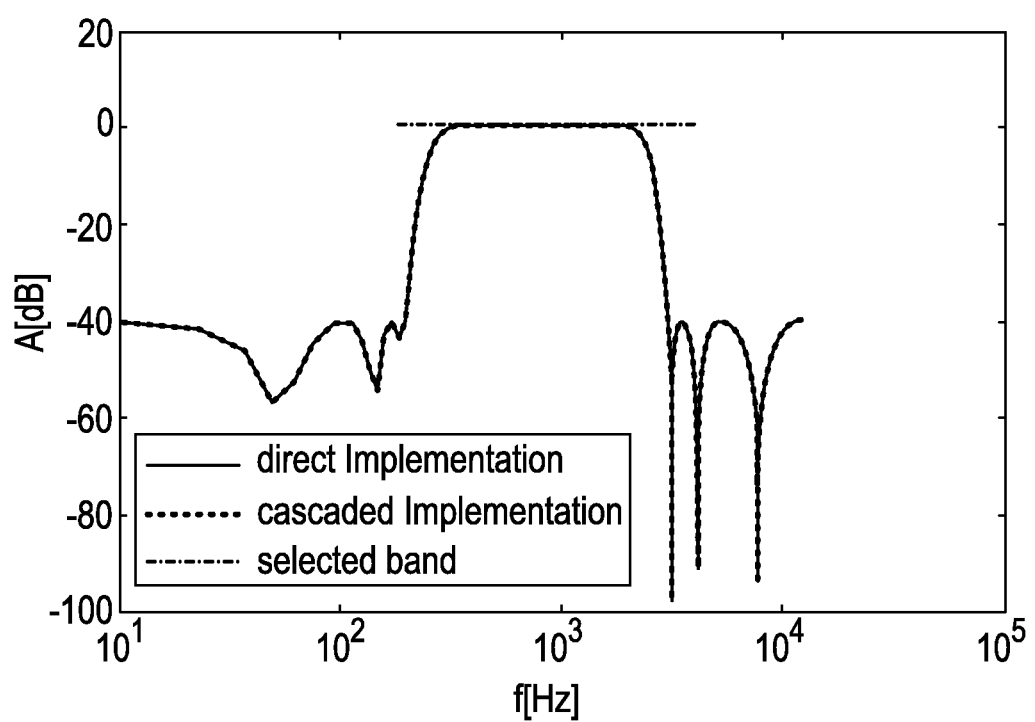
FIG. 27 illustrates exemplarily a Chebyshev type II band pass frequency response.

In FIG. 25 the signal spectrum is displayed with and without digital bandpass filtering (1051 vs 1050). The dotted points are in the range selected for evaluation. Different dot symbols represent different filter types which actually do not show a significant difference and can thus be ignored. In FIG. 26 the band pass 1054 is attached to a commercial low noise audio range amplifier 1053, wherein the type is DLPVA-100-BUN-S of FEMTO Messtechnik GmbH. In FIG. 27 the actual 40 dB suppression spectrum of the digital filter is compared to the range of the selected band. The two implementations do not show a noticeable difference. The displayed filter is applied to the data shown in FIG. 25, leading to the difference between 1050 and 1051.

From the determined frequency and the known time stamp of the receive signals, the correct timing for the next block of excitation pulses can be calculated. The number and width of excitation pulses is adapted to generate an oscillation with sufficiently high amplitude to produce sufficient signal in the receive coils.

Figure 29:
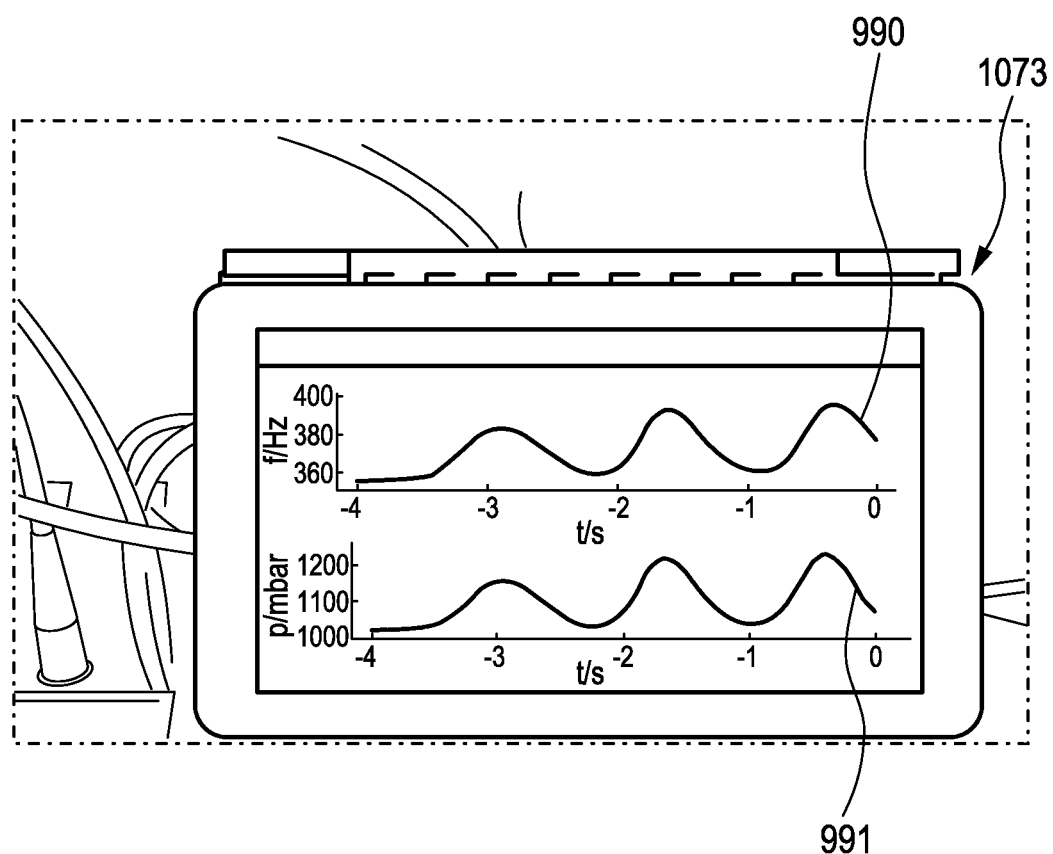
FIG. 29 shows exemplarily a detected sensor response frequency versus measured reference pressure.
Figure 30:
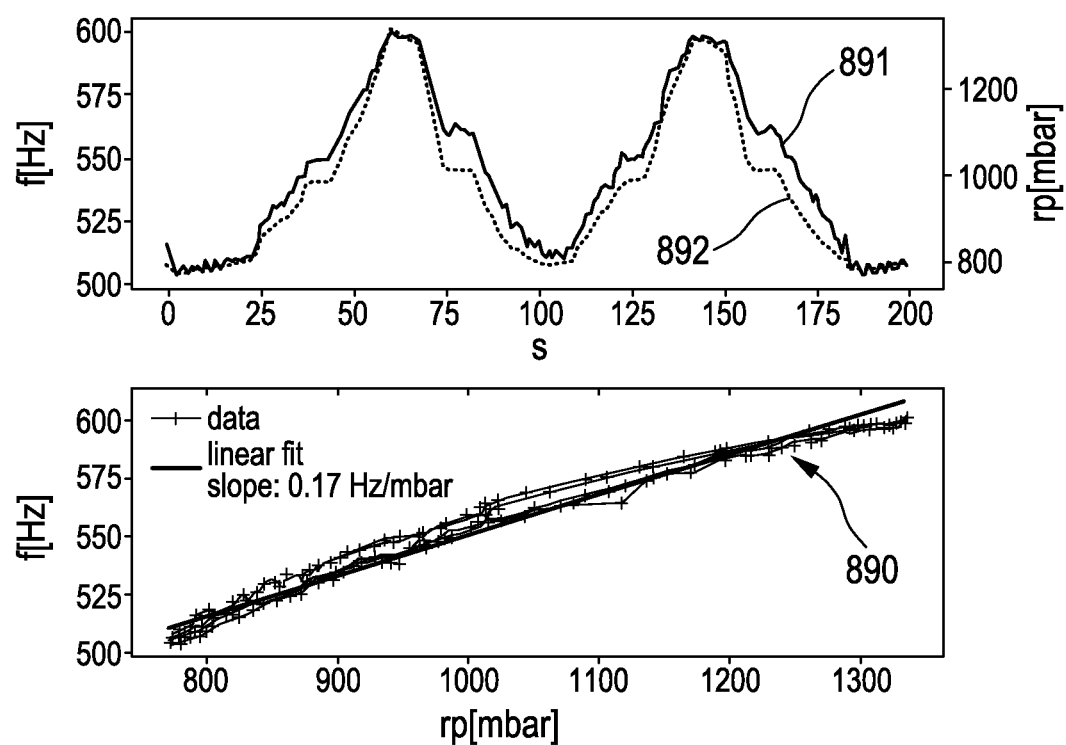
FIG. 30 shows exemplarily i) the alignment of a detected sensor response frequency with a measured reference pressure and ii) a calibration curve.

For calibrating a pressure sensor, the frequency response needs to be acquired for many well-defined pressures acting on the sensor. To this end, a high-quality pressure sensor can be connected to a pressure chamber containing the sensor (cf. FIGS. 28 and 29). From one or more sweeps over the relevant pressure range (up to 400 mbar above ambient pressure to safely cover the blood pressure range), a frequency-versus-pressure calibration curve can be determined as shown in FIG. 30. Depending on the sensor properties, a simple fit to the calibration curve may be good enough. However, a real sensor may exhibit hysteresis behavior, a dynamic response behavior of the membrane or other mechanical sensor elements, or a temperature dependence. Thus, it may be desired to fit a model based on physical sensor parameters to the measured calibration data to arrive at a highly accurate calibration of the sensor.

Figure 28:
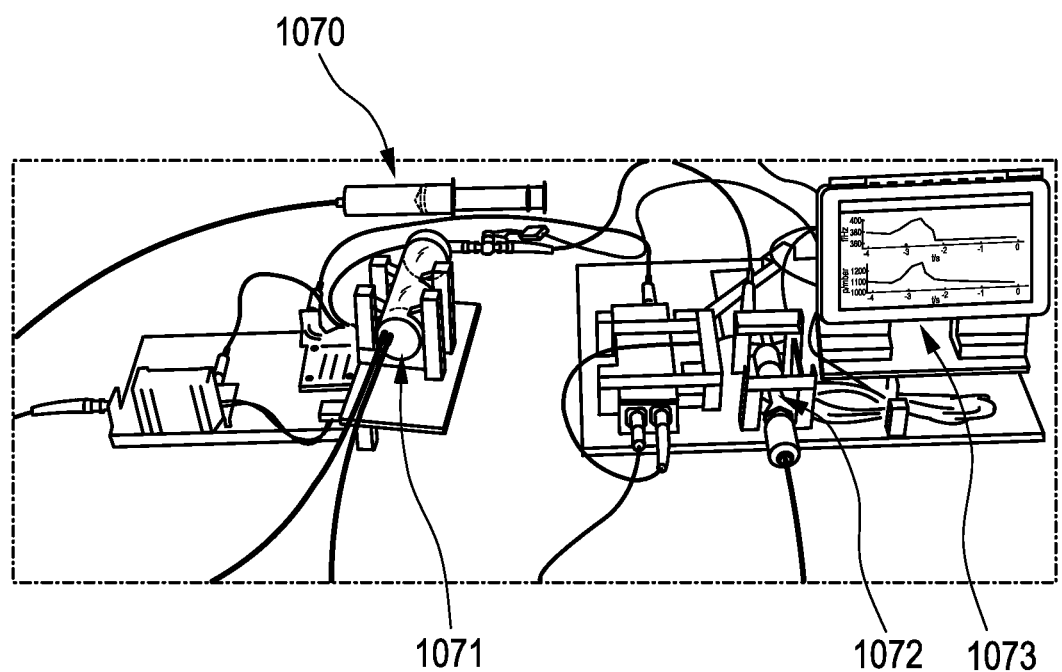
FIG. 28 shows schematically and exemplarily a calibration setup for calibrating a pressure sensor.

FIG. 28 shows schematically and exemplarily a calibration setup for calibrating a pressure sensor, wherein the calibration setup comprises a pressure applicator 1070, a pressure chamber 1071, a reference pressure sensor 1072, which might be a commercial pressure sensor and a data logging and display unit 1073. The pressure applicator 1070 applies a certain pressure as measured by the reference pressure sensor 1072 while the resonance frequency is measured such that, during this calibration procedure, measured resonance frequencies can be assigned to actual pressure values. FIG. 29 shows schematically the data logging and display unit 1073 showing the measured reference pressure 991 and the measured sensor response frequency 990, i.e. FIG. 29 shows a real-time display of detected sensor response frequency versus pressure measure using a commercial reference pressure sensor. FIG. 30 shows in its lower part a corresponding calibration curve 890 and in its upper part a comparison between the reference pressure 892 and the resonance frequency 891 which are in good alignment. The sensitivity of this exemplary calibration curve is 0.17 Hz/mbar which corresponds, if a frequency solution of about 20 mHz is assumed, to a pressure resolution of about 0.1 mmHg.

Figure 31:
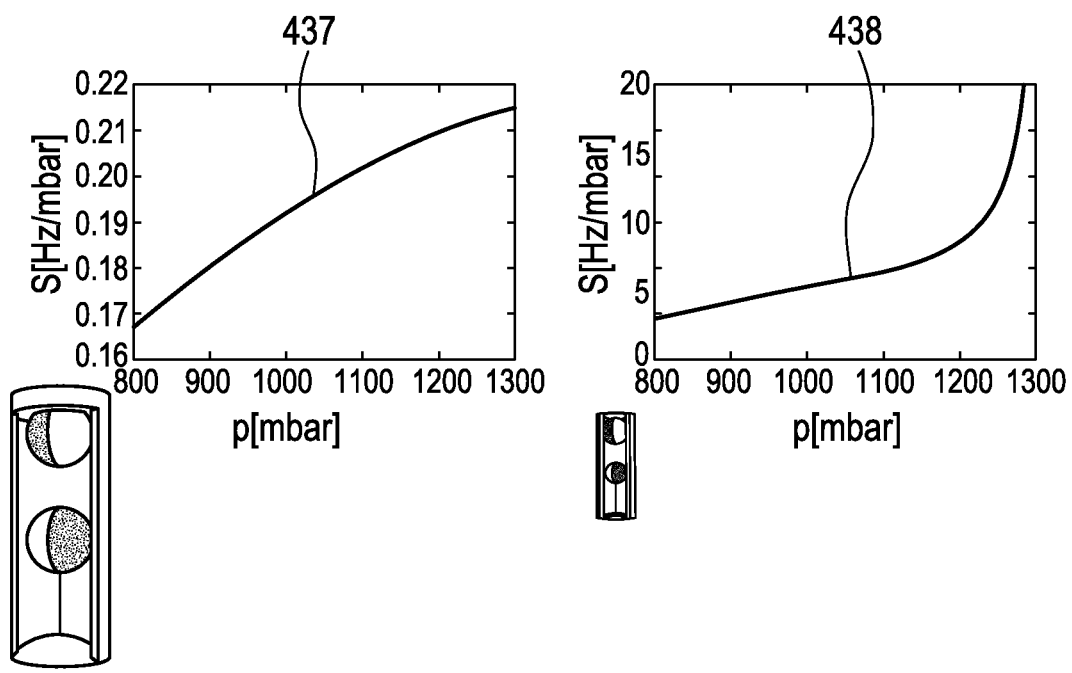
FIG. 31 shows exemplarily simulation results for a sensor sensitivity.

The sensitivity of the sensor is determined by the magnitude of frequency variation per pressure variation. This depends on several parameters, such as sensor design, membrane stiffness, size of magnetic elements, and distance of magnetic elements. For a given design and sensor size, simulations enable finding the optimal distance between the magnetic elements as well as the required membrane properties for optimal deflection versus applied pressure. FIG. 31 shows a simulation example predicting sensor sensitivity of the frequency range of interest for two sensor sizes. In this figure the curve 437 corresponds to a demonstrator and the curve 438 corresponds to the above described target size for a fractional flow reserve (FFR) application.

Figure 32:
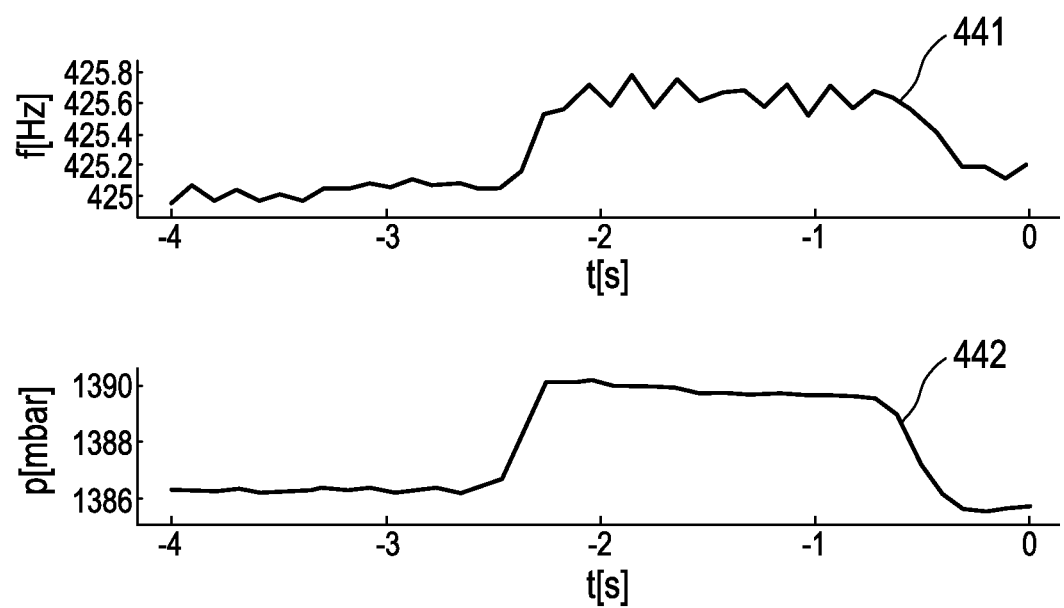
FIG. 32 illustrates exemplarily a noise level of the pressure measurement.

Beside the relative sensor sensitivity determined above, the absolute sensitivity or pressure resolution depends on the noise level on the frequency determination. In the example shown in FIG. 32, the noise level is about 0.2 Hz and limits the sensor resolution to about 1 mbar, wherein the curve 441 shows the sensor frequency response and the curve 442 shows the measured reference pressure. FIG. 32 refers to the noise level at an initial demonstrator which limits the pressure resolution to about 1 mbar. Already this is sufficient for most medical applications. Improved strategies of background noise removal can further increase resolution.

The processor of the reading system for wirelessly reading out the respective pressure sensor can be configured to apply a compensation algorithm, in order to correct the pressure value determination for a dependence of the resonance frequency on at least one of a) a distance between the pressure sensor and the field generator and b) an in-phase coil excitation. This compensation will be explained in more detail in the following.

Here, methods for compensating the distance and also orientation influence on frequency in a magneto-mechanical resonator for position and parameter, i.e. pressure, measurement are introduced. This compensation is only required when a physical parameter like pressure is sensed and the information is encoded in the oscillator frequency. For localization of the oscillator, which will be explained further below, frequency effects are either irrelevant (sensitivity encoding discussed further below) or negligible (gradient field encoding also discussed further below). For localization using the gradient field method which also acts on the sensor frequency, these compensations are not necessary, as there only the frequency change over a sub-second period of time needs to be evaluated. This change is not much dependent on the oscillation amplitude.

The signal of the magneto-mechanical oscillators is detected by the voltage $u_i(t)$ induced in a coil i as a result of the field variation due to the oscillatory motion of the magnetic moment $m(t)$ of the suspended magnetic sphere at position $r_0$:

$$u_i(t) = -\frac{d}{dt}(B_{S,i}(r_0) \cdot m(t)) = \qquad (4)$$

$$-B_{S,i}(r_0) \cdot \frac{d}{dt}m(t) = -M_{sat}V_{sphere}B_{S,i}(r_0) \cdot \frac{d}{dt}\hat{m}(t),$$

wherein $B_{S,i}(r)$ is the coil sensitivity of detection coil i at position r, which is mostly constant over time. In the last step, the magnetic moment has been replaced using $$m(t) = M_{sat}V_{sphere}\hat{m}(t), \qquad (5)$$

where $\hat{m}(t)$ is a unit vector describing the spatial orientation of the magnetization, $M_{sat}$ is the saturation magnetization of the material used (typically between 1.30 and 1.45 T/$\mu_0$ for NdFeB), and $V_{sphere}$ is the volume of the magnetic object.

From (4) it follows that a large dynamic magnetic moment is desirable to induce a high voltage in the receive coils. Since the volume of the spheres has to be small in most applications, signal can be increased by using a large oscillation amplitude leading to a large $d/dt\hat{m}(t)$. However, the restoring torque does not increase linearly with angle $\varphi$ (i.e. the amplitude of the oscillation) between restoring field $B_{rest}$ provided by the fixed sphere and magnetization m of the oscillating sphere:

$$|T(\varphi)| = |m \times B_{rest}| = mB_{rest}\sin\varphi \qquad (6)$$

Considering the torque due to friction $T = C\dot{\varphi}$ with damping coefficient C and the torque required for angular acceleration of a sphere with mass $m_s$ and radius $r_s$, $T = \frac{2}{5}m_s r_s^2 \ddot{\varphi}$, one can set up the equation of motion:

$$mB_{rest}\sin\varphi + C\dot{\varphi} + \frac{2}{5}m_s r_s^2 \ddot{\varphi} = 0. \qquad (7)$$

The small angle approximation $\sin\varphi \approx \varphi$ and the replacement $m = M_{sat}V_{sphere}$ leads to $$M_{sat}V_{sphere}B_{rest}\varphi + C\dot{\varphi} + \frac{2}{5}m_s r_s^2 \ddot{\varphi} = 0. \qquad (8)$$

The high quality factor of the system allows the further approximation $C \approx 0$ and enables calculation of the angular resonance frequency as $$\omega_0 = \sqrt{\frac{5M_{sat}V_{sphere}B_{rest}}{2m_s r_s^2}}. \qquad (9)$$

Since the micro-oscillators are typically driven to amplitudes much larger than 10°, this approximation is not valid in the general case. For large angles, the restoring torque is smaller and thus a reduction in frequency occurs, leading to an amplitude dependent frequency $\omega(\varphi_{max}) = \omega_0 k(\varphi_{max})$, with $k(\varphi_{max}) < 1$. The variation in restoring torque during the oscillation furthermore introduces a non-linearity in the sensor response, that is manifested by the existence of higher harmonics of the base frequency in the spectrum.

In addition to the non-linear restoring torque, the force between the two magnetic spheres depends on the mutual orientation of their magnetizations:

$$F(r, m_1, m_2) = \frac{3\mu_0}{4\pi r^4} m_1 \, m_2 \, \cos \varphi \qquad (10)$$

For the given sensor design, the force always points along the connecting vector of the two magnetic spheres, however, its magnitude goes to zero at an oscillation amplitude of 90° and even goes from attractive to repulsive at higher angles. If the filament from which the sphere is suspended elongates due to the applied force, then the average force reduction at high oscillation amplitudes increases the distance between the spheres, reducing $B_{rest}$ and thus the oscillation frequency. Not only the filament can change its length, but also potentially other structures in the sensor.

If the excitation fields generated by the transmit coils had a constant amplitude, the oscillation amplitude $\varphi_{max}$ would decrease with increasing distance between coil and sensor (decreasing excitation field) and thus the frequency would decrease. The amplitude also depends on the relative orientation between coils and the sensor as show in FIG. 33.

Figure 33:
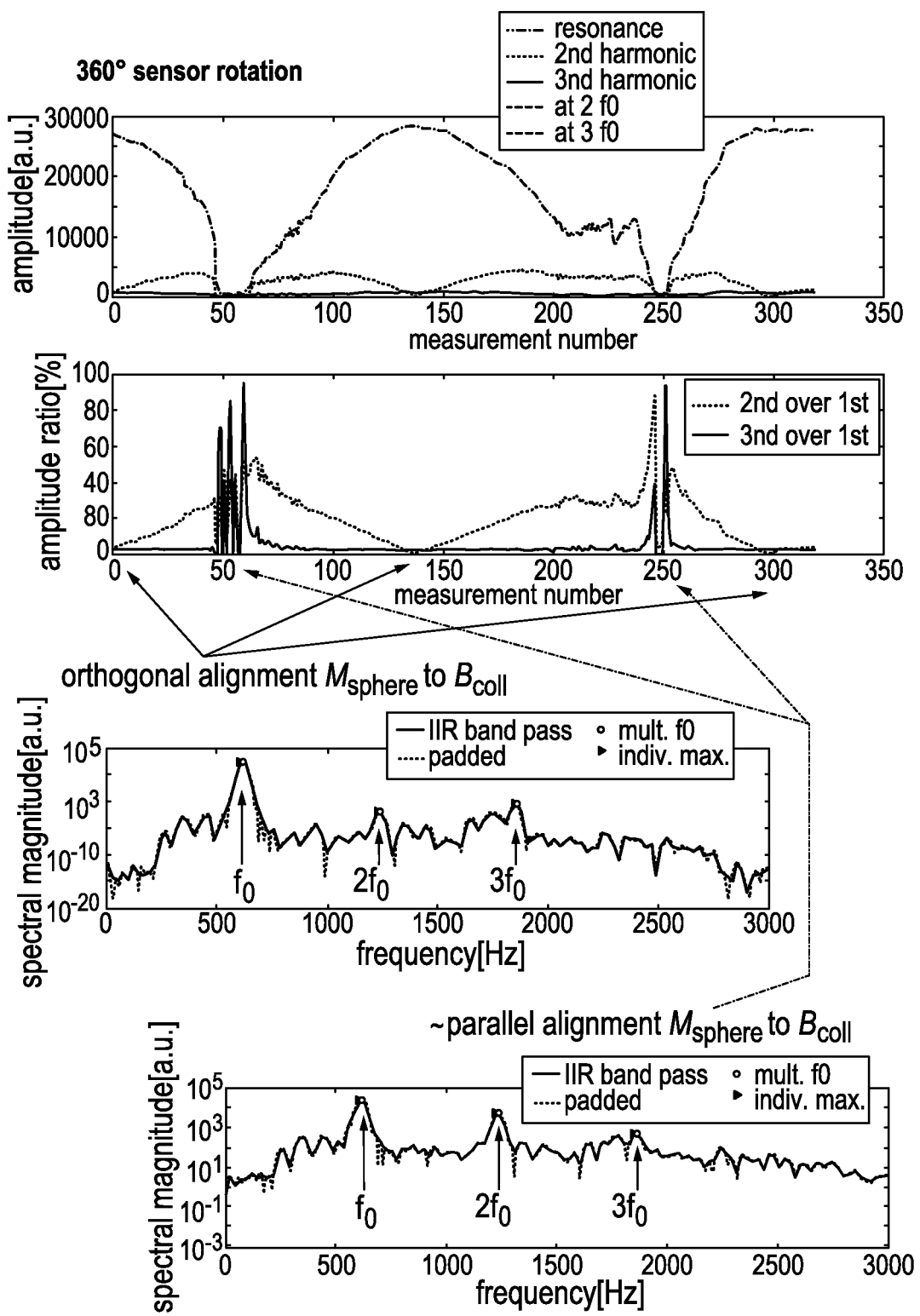
FIG. 33 shows a measured dependence of signal amplitude in different harmonics on sensor orientation with respect to a single transmit-receive coil.

FIG. 33 illustrates a measured dependence of signal amplitude in different harmonics on sensor orientation with respect to a single transmit-receive coil. If the excitation field is aligned parallel to the magnetic dipole orientation, no excitation occurs, and the signal is zero. For orthogonal alignment of field and dipole, the highest oscillation amplitude is achieved. Note that the spatial pattern of the even harmonics is aligned orthogonally to the odd harmonics. This can be seen by the zero of the $2^{nd}$ harmonic amplitude at the orientation corresponding to the maximum in the base signal ($1^{st}$ harmonic) and $3^{rd}$ harmonic. The amplitude ratio plot (center graph) highlights this difference in orientation dependences: the $2^{nd}$ over $1^{st}$ harmonic ratio goes from zero to a maximum value (or singularity) while the $3^{rd}$ over $1^{st}$ harmonic ratio is flat. The knowledge that the dynamic response at even harmonics is oriented orthogonally to that of odd harmonics can be used to determine the $3^{rd}$ orientation angle of the sensor.

A naïve frequency determination would therefore result in readings that are not only dependent on the physical quantity, but also on the position and orientation of the sensor. This is generally not desirable and hence mechanisms to reduce this effect are preferentially employed.

There are two strategies to mitigate the effect. One is to ensure that the oscillation amplitude remains constant for all valid positions and orientations (i.e. in the field of view). The other is to calculate a virtual frequency from one or many frequency readings, where the virtual reading is independent of oscillation amplitude. The chosen virtual frequency may be the resonant frequency at very low amplitude, i.e. a zero amplitude frequency as given by equation (8). Naturally a combination of the two strategies can be used.

In the following a control of the oscillation amplitude will be described, wherein the position and orientation of the pressure sensor as known from localization is used.

The conceptually simplest way to correct for the frequency shift is to use the known position and orientation relative to the send/receive coil array. This position can be obtained by sensitivity encoding or gradient encoding or a combination, all described further below. When the position and orientation is known, it is possible to deduce the absolute dynamic dipole moment. Usually the dynamic dipole moment is already a fitting parameter during the position determination. Otherwise it is deduced from the known sensitivity of the coils at the relative sensor position and orientation and the recorded signal strength as given by equation (3). From the dynamic dipole moment and the known static dipole moment of the sensor, the oscillation amplitude can be deduced. (If the sensor static dipole moment is not previously known, it can be deduced from multiple dynamic dipole moments measured at different excitation amplitudes as the reached or extrapolated maximum possible dynamic dipole moment.) Now, the transmit field amplitude can be adjusted to reach a pre-determined maximum oscillation angle $\varphi_{max}$. A slightly simpler, but also slightly less reliable method is to simply adjust the send amplitude to a value so that the driving field component at the sensor is always constant. Usually one directional field component (amplitude in one direction relative to the sensor) dominates the excitation process. The amplitude depends on the various simultaneous excitation currents in the several excitation coils. The amplitude and phase of the current in the coils is adjusted in a way to give the desired amplitude at the desired position and the desired orientation. How that is done is well known in the field of electromagnetism. As the solution to this problem and the previous method of adjusting the send amplitudes is not unambiguous, at least one second criterion for the current optimization is used. "Not unambiguous" in this context means that a multitude of amplitude phase combinations in the send coil currents have the same desired outcome. The second criterion is usually the minimization of an undesired side effect of the excitation. Examples for the undesired side effect are total power dissipation, maximum power dissipation in one coil, maximum temperature in one coil (which also dependents on excitation history), heating or forces in surrounding objects. Naturally any other related criterion or combinations can be used for this optimization. It is also valid not to use the optimum, but simply to use the first valid solution a specific optimization algorithm (as gradient descent or simulated annealing etc.) has found.

In the following the determination of the zero-amplitude frequency will be described, wherein a position and orientation of the pressure sensor known from a localization procedure is used.

The second approach, where the amplitude is not controlled, but the frequency is converted to e.g. the zero amplitude frequency may be described as well for the case of known position relative to a coil array. For this approach, a model of the sensor is needed. This model describes the relation of frequency and oscillation angle directly or in some equivalent form, like frequency and dynamic dipole moment strength. This model may be in the form that the frequency is expressed as the zero amplitude frequency minus a function depending on the oscillation amplitude. More complex descriptions can work as well, e.g. multiplication by a correction term like $k(\varphi_{max})$ introduced after equation (6) above. Both, the frequency and the amplitude may be interpreted as the average or a curve fit over a predetermined integration period or sequence length. As the position and coil sensitivities are known, the oscillation amplitude can be determined from the recorded signals as described above. So, as the actual frequency and the amplitude are known, the zero amplitude frequency can be deduced by inverting the model function. The inversion may be performed in an analytical way or by well-known numerical methods.

Mathematically, instead of the zero amplitude frequency any other related quantity can be used as well e.g. the frequency at 10° amplitude and also quantities that do not reflect frequency at all, e.g. the absolute inter-sphere distance. However, such a transformation does not change the fundamental nature of this evaluation process.

Usually even when using the zero amplitude extrapolation method, some sort of amplitude control is preferentially introduced for most applications. If the sensor is near the coil array, a lower current through the coils can be used than when the sensor is further away. The zero amplitude extrapolation method has the benefit that it can work even if the sensor is so far away that a pre-determined oscillation amplitude for the constant amplitude method cannot be maintained any more due to limitations on the coil current.

The descriptions above assumed that the oscillation amplitude can be derived from the known position and orientation of the sensor and the induced voltage in the receive coils. However, any other method that can provide the amplitude information can be used to compensate for the amplitude dependent frequency, using both the constant excitation and the extrapolation method. Below, some alternative methods for this amplitude determination will be provided. These methods may be useful when only a low number of coils are available, and the exact relative position cannot be determined. The compensation methods themselves will not be repeated in the text below.

In the following it will be described how the oscillation amplitude can be determined by using amplitudes of harmonics of the base frequency.

One method to determine the oscillation amplitude is to evaluate the harmonics of the induced signal in the coils. Being non-linear oscillators, the magneto-mechanical sensors generate harmonics of the resonance frequency in the dynamic dipole moment. These harmonics are picked up in the receive coil(s). Preferentially, care is taken to not suppress these multiples of the base frequency in the sampling and filtering step. The spectrum of the harmonics depends on the details of the sensors. There can be sensors that predominantly generate odd harmonics (at $3\omega_0$, $5\omega_0$, ... ) and ones that generate even and odd harmonics (at $2\omega_0$, $3\omega_0$, $4\varphi_0$, ... ). However, mixed types can be constructed. The dynamic dipole moment of the odd harmonics tends to align with the dynamic dipole moment of the fundamental frequency, while the even harmonics tend to be aligned perpendicular to the base frequency dynamic dipole moment and perpendicular to the rotation axis. Therefore, the odd harmonics are conceptually the easiest to be used, because the ratio of say the third harmonic's dynamic dipole moment to base frequency's dipole moment is reflected as the corresponding ratio in the recorded voltages in a single coil, e.g. evaluated as spectral peak amplitudes. However, as the amplification in the receive system may be frequency dependent, preferentially a correction is applied to get hold of the true ratio of the 3rd harmonics dynamic dipole moment and the base frequency dynamic dipole moment. This ratio may be measured over a predetermined integration period. For each sensor, a calibration of this ratio to oscillation amplitude or directly frequency shift can be provided and therefore the corrections applied. In the case of the even harmonics, the situation is somewhat more complicated, as the direction of the dynamic dipole moments do not align with the base frequency dynamic dipole moments. So here usually more than one coil needs to be employed or the orientation of the coil relative to the sensor needs to be determined by other means. While with a large set of coils (e.g. >=6), both sensor position and orientation can be reconstructed, few coils (e.g. 3-5) should at least allow reconstruction of the orientation of the sensor relative to the coils using similar methods to the positioning determination methods described in this document. Then the true ratio of the dynamic dipole moments for even harmonics can be determined using coil sensitivities. The intermediate step of orientation determination can be omitted and a direct map of the ratios of base frequency amplitudes and harmonics amplitudes in the coils can be established using linear algebra methods. It shall be understood that the methods described here in frequency domain can be mapped to methods in other bases like the time domain. In time domain, the frequency analysis is mapped to an oscillation shape analysis. These mapping methods are well known in the mathematical literature.

In the following a determination of the oscillation amplitude based on a time-domain envelope function will be described.

Another way to determine the oscillation amplitude is to utilize the non-linear decay behavior of the signal. The damping of the sensor is usually non-linear. Non-linear decay means that at double stored energy, the average dissipation power of the sensor is not doubled but increased by a factor somewhat higher than two. The reason for this can be the stretching of the filament due to the force modulation described above. Equation (9) shows that at low oscillation amplitudes the attractive force between the magnetic objects are largely constant, but at higher amplitudes they are no more. This force variation depends in first approximation on the square of the oscillation amplitude, corresponding to the approximation of the cosine function by a parabola. This square dependency is the reason for the non-linearity in dissipation. The changing force between the magnetic object periodically stretches the filament(s) which leads to a dissipation contribution. Other effects may as well lead to non-linear behavior. In total these effects lead to the situation that the envelope shape of the decay curve over a given time depends on the initial amplitude. So, if the sensor has constant initial oscillation amplitude and the distance and/or orientation of the sensor is changed relative to the receive coil(s), a scaled version of the initial decay envelope is found. However, if the excitation amplitude of the sensor is changed, not only the overall amplitude of the decay curve varies, but also its shape. This means that amplitude effects and distance/orientation effects can be disentangled and hence the initial oscillation amplitude can be reconstructed using e.g. a lookup-table of pre-recorded decay curves. This again leads to the possibility of determining the zero-amplitude frequency or to a controlled constant amplitude excitation as described above. This method only needs a single coil to work. However, it is somewhat sensitive to a movement of the sensor during the recording as this also changes the shape of the envelope. Therefore, it is beneficial to incorporate a model of likely sensor movements into the evaluation. For example, if it is known that the sensor will not perform fast accelerations, correcting the decay curve envelope with the assumption of persistent motion is useful.

A determination of the oscillation amplitude based on signal amplitude response to variations in excitation fields will be explained in the following.

Yet another method to determine the oscillation amplitude is to analyze the reaction of the sensor signal to different strength of the excitation. In this case, the current pulses are systematically varied and the response of the sensor(s) to the different excitation pulses is evaluated. The send pulse current, duration and phase may be varied or a combination thereof. For example, assume that there are two excitation pulses. If the distance is high and the local field amplitude is low, the two pulses are designed to generate twice the amplitude a single pulse would produce. However, if the distance is low and the local field at the sensor is high, the amplitude will be less than twice the amplitude. This results in a characteristic decrease of the receive voltage relative to the expected factor of two. So, the ratio(s) of the receive signal (Fourier) amplitudes of the sensors for a given excitation pattern is a measure of the excitation amplitude and can again be used for extrapolation to the zero amplitude frequency and/or for having a constant excitation amplitude. On top of that, other quantities like the frequency and decay time may be evaluated as well. The ratios of these quantities are also characteristic for the oscillation amplitude and can be used for extrapolation to the zero amplitude frequency.

In the following a determination of a correct parameter based on a full model of all contributing factors will be described.

All the methods described above are just evaluation methods with some methods requiring changes in the transmitted field pulses. No hardware change to the system is needed to do these evaluations. Therefore, it is logical to implement all of them. This may be done my simply running the evaluations in parallel and combining the results in a way to minimize noise, i.e. do a weighted average according to relative noise. While this is relative straight forward and easy to implement, better results can be expected by using a truly integrated mathematical approach that will be outlined below. On the flip side, the mathematically sophisticated approach is considerably more difficult to implement and may need too many computational resources to run on cost-efficient computer hardware. The basis for the correct mathematical approach is a mathematical model for the sensor. This model predicts the sensor response to the excitation fields, current sensor state, and measured parameter, i.e. sensor environment. The sensor state may be the only the current deflection angle and rotation speed of the suspended sphere. However, especially but not exclusively for pressure sensors, this may also incorporate the elastic state of the structures that can deform under external or internal varying forces. So, models for the hysteresis of membranes and filaments need to be incorporated. This model can have different mathematical forms, but the most common way is to formulate this model in a set of differential equations. Then also a model of the transmit and receive coils including filter and amplifier characteristics has to be generated. This can be formulated in differential equations, although here a Fourier parameter representation is also not uncommon as long as the transmit and receive systems are sufficiently linear in nature. Lastly, a model for coil transmit and receive sensitivity needs to be provided. This may be simply a set of spatial points with attached sensitivities and an interpolation algorithm between the points. It could also be based on a simulation of the coils based on the Biot-Savart law. This model can now predict the voltage response of the sensor at any given location and orientation with the given history of excitation pulses and external parameters. So, the procedure is to vary sensor position and orientation and the sensor influencing physical parameters in the simulation in a way that the recorded signal and the simulation match in the best possible way. Many well-known optimization methods may be used, such as gradient descent or random walks. The match may be defined as the root mean square of the sum of the difference of the measured sample points and the simulated sample points. The match is best if this quantity is lowest. The best fit may be altered introducing additional constraints, e.g. by a model of the expected relative positions and orientations or by a constraint on the maximal expected sensor accelerations and/or a model of the measured quantities, which for instance give a constraint on the maximal rate of change in these quantities. Additional sensor input may be used as well, like accelerometers on a hand-held coils system for at least one independent input of distance and orientation changes. As the full model-based evaluation processes are computationally intensive, they can be combined with one or several of the previous methods to give a good starting point for further optimization.

The processor can also be configured to compensate for gravitational effects as it will be explained in the following.

In a pressure sensor, the weight of the movable sensor segment can have an influence on the pressure reading: if it is on top of the fixed sensor part, it compresses the sensor and thus leads to an apparent increase in pressure, if it is at the bottom, it leads to an apparent decrease. The gravitational force (weight) on a NdFeB sphere of diameter 0.5 mm is about 5 μN. For comparison, the change in force on the cylindrical backside of the sensor (conservatively assuming that the diameter is the same as for the sphere) created by a pressure change of 1 mbar is about 20 μN. The force difference between up and down orientation of the sensor in air would thus limit accuracy to 0.5 mbar. To mitigate this problem, a correction can be applied based on the spatial orientation of the sensor obtained from one of the methods described for recovery of (position and) orientation in this document. In a liquid environment, such as blood, the weight effect can be minimized by matching the density of the sensor segments to the density of the liquid, buoyancy then compensates the gravitational force.

The processor can also be configured to compensate for earth magnetic field and other static field effects.

Static background fields add to the field of the fixed magnetic object and thus modulate the restoring field $B_{rest}$ seen by the oscillating magnet. This changes resonance frequency according to equation (8) and is therefore a source of error for sensing via the oscillator's frequency changes. It is not relevant for oscillator localization. For magnetic spheres of diameter 0.5 mm made from NdFeB with a saturation magnetization of 1.3 T/$\mu_0$, the fields created by the fixed sphere at the center of the oscillating sphere are 16.1 mT and 6.8 mT for center-to-center distances of 0.75 mm and 1.0 mm, respectively. Earth magnetic field is between 25 and 65 μT. The frequency difference between parallel and antiparallel alignment of the static field component with the maximum earth magnetic field of 65 μT would create a frequency difference of about 5 Hz and 9 Hz for the above distances of 0.75 mm and 1.0 mm, respectively. Regarding the typical frequency resolution of between 10 and 100 mHz and prototype sensitivities of −0.3 K/Hz for the temperature sensor and 20 mbar/Hz for the pressure sensor, this worst-case calculation leads to substantial errors in the sensed values. Different mitigation strategies to this are introduced in the following.

A mitigation on the sensor side is the use of the design employing two suspended spheres with identical magnetic dipole moment and moment of inertia (or a suitable ratio of the two quantities) instead of a single sphere. Since the counter-oscillation occurs at a single frequency, the first order effect of a static bias field like the earth magnetic field is cancelled.

Another mitigation strategy is to use absolute field sensors in the detector system to measure magnitude and orientation of static background fields. Based on the sensor orientation determined using the methods discussed in this document, a frequency or field correction can be calculated to arrive at the correct sensor value for pressure, temperature, or other parameters. For sensing static background fields, any magnetic field sensor with sufficient sensitivity and a footprint that can be integrated in the detector system can be used. One cost-efficient choice could be 3-axis Hall sensors. An alternative would be a 3-axis array of temperature-compensated micro-bots with a well-defined zero-field frequency. From the change to their respective frequencies, the magnitude and orientation of the background fields can be determined. Ideally, their resonance frequencies are chosen such that they do not interfere with the frequency of the sensor of interest. Instead of correcting for the frequency offset in the evaluation, one can also use the coils of a multi-coil detection systems to generate small offset fields to counter-balance the earth-magnetic and other background fields. If inhomogeneous fields exist in the field of view due to the presence of ferromagnetic material, several sets of 3-axis magnetic field sensors can be employed to characterize the spatial field variations. Based on an interpolated background field map derived from these measurements, a correction for a sensor at known position and orientation can be calculated or the respective correcting offset fields can be applied or a mixture of the two correction methods is used.

The pressure sensors, and also markers, should have a high quality factor and need to have a large frequency sweep to be sensitive to the measured quantity over the range required for a specific application. The high quality factor is especially important at high oscillation amplitudes where the highest signal is generated. As the two magnetic objects have strong attractive forces, and the forces strongly increase with shrinking distance (to the $4^{th}$ power of the distance, cf. equation (9)), both properties may be worsened. The strong forces lead to a relatively strong tension in at least one filament holding at least one magnetic object. This tension itself does not lead to a dissipation path. However, especially at large oscillation amplitudes, the forces between the magnetic objects are reduced and thus the tension on the filament is periodically reduced. This results in a periodic lengthening and shortening of the filament which usually results in heat generation. Hence, power is extracted from the oscillator. The forces also depend strongly on the distance of the magnetic objects and become very large if the objects get close to each other. This behavior is especially problematic for pressure sensors. The force between the magnetic objects is functionally equivalent to an external pressure. So, if the external pressure is increased, the magnetic objects get closer, which in turn increases the apparent pressure. This effect is compensated when using a measured calibration curve for pressure determination, but it can lead to the situation when the sensor reaches a tipping point where the magnetic objects are rapidly pulled to each other and finally get in touch. This leads to a state, where the sensor does not work anymore. This can be avoided by simply making the pressure sensor's membrane or bellow structure stiffer. However, this reduces the sensitivity of the sensor, i.e. the frequency shift per applied pressure. To solve this problem, a method to reduce the force and the change of the force is described. It consists just of a portion of magnetic material that is magnetized in the opposite direction next to the other magnetic object, as shown in FIG. 34.

Figure 34:
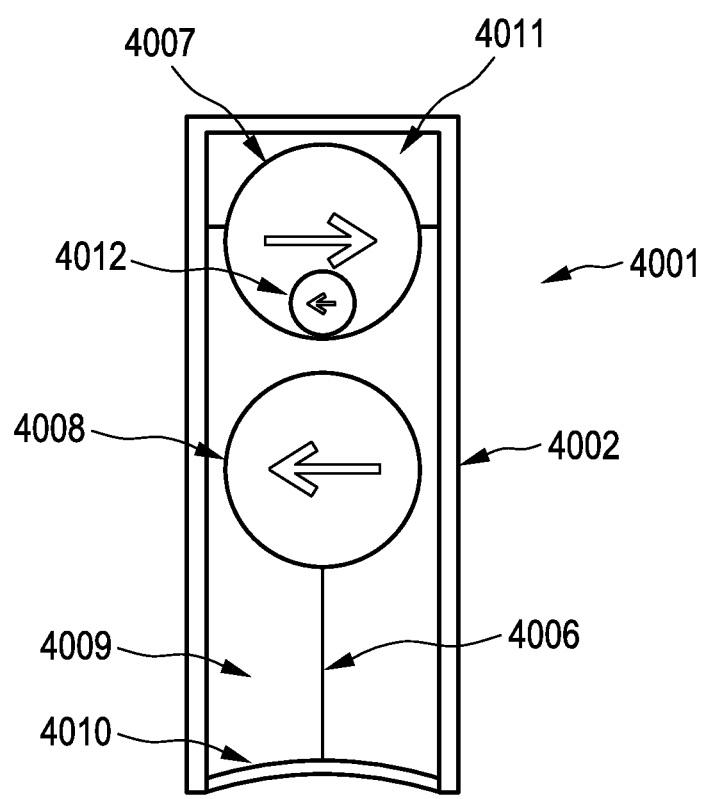
FIG. 34 shows schematically and exemplarily a further embodiment of a pressure sensor.

In FIG. 34 the pressure sensor 4001 comprises a magnetic object 4008 being a permanent magnet suspended via a filament 4006, which is preferentially a high strength wire, from a flexible part 4010 of a casing 4002. The flexible part 4010 is preferentially a membrane, which might be a latex membrane. The remaining part of the casing 4002 might be made of metal or of a polymer. The casing 4002 might be filled with gas or it might provide a vacuum space, wherein the inner space has the reference sign 4009 in FIG. 34. A further magnetic object 4007 is fixed via glue 4011 to an inner end surface of the casing 4002. The two magnetic objects 4007, 4008 are generally magnetized in opposite directions. However, the fixed magnetic object 4007 also comprises a part with a reverse magnetization orientation 4012.

So, if two magnetic spheres are involved, in this example at least one sphere obtains a cap magnetized in opposite direction. The cap is located next to the other magnetic sphere. If one sphere is fixed and the other one is oscillating, it is best to have the cap on the fixed sphere. In this way, the dynamic dipole moment of the sensor is not reduced. Only the oscillation frequency is slightly lower. However, it is also possible to reverse the roles of the spheres. The oppositely magnetized portion is so small that at all operational distances, the net force between the magnetic objects is still attractive. If the reversely magnetized portion is small enough, the attraction condition can be meet right until touching of the magnetic objects. There are several ways to make the reversely magnetized caps. One is to just add some magnetic material on top of at least one magnetic object. The magnetic material can be magnetically soft or magnetically hard. It can be a solid continuous magnetic object or a magnetic paint or something in between. The magnetic material tends to align in a way to form the opposite magnetization by itself. In addition, it also tends to stick to the magnetic object. Nevertheless, this additional material should be glued to the magnetic object especially if the two main magnetic objects can touch each other occasionally. To keep the originally desired shape, some material may be removed from the magnetic object to be altered, e.g. by grinding. There is an alternative way to form the reversely magnetized zone. It can be created just by reversely magnetizing the desired zone of the magnetic object. This could be achieved by strong pulses of current through a conductor near the magnetic object. However, this is not very practical due to excessive heating. It can be achieved easier by just heating the affected portion of the magnetic object to near or above the Curie temperature. This will result in the reversal of the magnetization. The effect can be augmented by applying a pulsed or constant magnetic field in the reverse direction. The fields can also incorporate strong gradients by using some hard or soft magnetic material near the zone to be affected. As the heating has to be fairly localized, the temperature increase needs to be very rapid, so that the total energy deposited into the magnetic object is low and does not bring it near Curie temperature as a whole. A suitable heating source could be a laser. Resistive or inductive heating methods may work as well.

In the following it will be explained how a pressure sensor might be localized.

For a tracking system, orientation and 3D position of a marker, which might also comprise the magneto-mechanical oscillator, needs to be determined, but also for a pure sensing system, orientation and position of the oscillator may need to be determined to enable improvement of the accuracy of the sensor reading as discussed above. Two independent localization strategies can be used for localization. In some situations, one strategy may be sufficient, in other situations, a combination of both methods can be useful to increase accuracy or to identify systematic errors (e.g. a strong ferromagnet in the workspace) that lead to contradicting results between the two methods.

On strategy would by localization based on coil sensitivity. This approach makes use of the fact that each coil i in a coil array has a different spatial sensitivity profile $B_{S,i}(r)$ based on its position and orientation. According to equation (3), a single oscillator then creates a response with a characteristic amplitude for each coil that is determined by the respective orientation of the dynamic dipole moment $$\frac{d}{dt}m(t)$$

of the oscillator with respect to $B_{S,i}(r)$. For reconstruction of sensor position and orientation, a set of forward functions as given by equation (4) needs to be determined. In the end, a mapping between the 6 marker position and orientation coordinates and the voltage amplitudes at base frequency or higher harmonics for all receive channels is desired. The following equations describe how to get rid of the time dependence in equation (4), so that only amplitudes need to be considered. We start by including all arguments, i.e. position vector $r=(x,y,z)^T$ and orientation vector $\varphi=(\varphi,\theta,\psi)^T$:

$$u_i(r, \varphi, t) = -B_{S,i}(r) \cdot \frac{d}{dt}m(\varphi, t) = -M_{sat}V_{sphere}B_{S,i}(r) \cdot \frac{d}{dt}\hat{m}(\varphi, t) \quad (11)$$

The required coil sensitivity profiles can either be calculated from the know coil geometries, measured at defined positions and then interpolated, or be determined in a mixture of both, i.e. a model that can be fitted to the experimental results with adequate fit parameters. For the oscillation of the magnetization, an explicit description for oscillation frequency ω and amplitude $\alpha_0$ in the frame of the marker would be $$\hat{m}'(t) = \begin{pmatrix} \cos(\alpha_0 \sin \omega t) \\ \sin(\alpha_0 \sin \omega t) \\ 0 \end{pmatrix} \approx \begin{pmatrix} 1 - \frac{1}{2}(\alpha_0 \sin \omega t)^2 \\ \alpha_0 \sin \omega t \\ 0 \end{pmatrix} = \begin{pmatrix} 1 - \frac{1}{4}\alpha_0^2(1 - \cos 2\omega t) \\ \alpha_0 \sin \omega t \\ 0 \end{pmatrix}, \quad (12)$$

where the prime indicates the local marker frame and the expansions of the trigonometric functions for low oscillation amplitudes $\alpha_0$ have been used. The temporal variation would then be $$\frac{d}{dt}\hat{m}'(t) \approx \begin{pmatrix} -\frac{1}{2}\alpha_0^2 \omega \sin 2\omega t \\ \alpha_0 \omega \cos \omega t \\ 0 \end{pmatrix} = \begin{pmatrix} 0 \\ \alpha_0\omega \\ 0 \end{pmatrix} \cos \omega t - \begin{pmatrix} \frac{1}{2}\alpha_0^2\omega t \\ 0 \\ 0 \end{pmatrix} \sin 2\omega t, \quad (13)$$

where the first term characterizes the base frequency response and the $2^{nd}$ term characterizes the $2^{nd}$ harmonic frequency response. Using rotation matrices $R(\varphi)$, the magnetizations for general orientation in space can be calculated, i.e. $\frac{d}{dt}\hat{m}(\varphi, t) = R(\varphi)\frac{d}{dt}\hat{m}'(t)$.

Thus, starting from (11), the voltage amplitudes for base frequency and $2^{nd}$ harmonic frequency can be determined as $$u_{1,i}(r, \varphi) = \quad (14)$$
$$-\alpha_0 \omega M_{sat}V_{sphere}B_{S,i}(r) \cdot \begin{pmatrix} \cos \varphi \sin \vartheta \sin \psi - \sin \varphi \cos \psi \\ \sin \varphi \sin \vartheta \sin \psi + \cos \varphi \cos \psi \\ \cos \vartheta \sin \psi \end{pmatrix}$$

and $$u_{2,i}(r, \varphi) = \frac{1}{2}\alpha_0^2\omega M_{sat}V_{sphere}B_{S,i}(r) \cdot \begin{pmatrix} \cos \varphi \cos \vartheta \\ \sin \varphi \cos \vartheta \\ -\sin \vartheta \end{pmatrix}, \quad (15)$$

respectively. Accordingly, total voltage for coil i would be $$u_i(r,\varphi,t) = u_{1,i}(r,\varphi)\cos \omega t + u_{2,i}(r,\varphi)\sin 2\omega t \quad (16)$$

From the set of forward functions (14) and (15) and the measured response amplitudes, the marker position and orientation can be calculated by solving the system of equations using a non-linear solver, which is a standard mathematical method. The accuracy of the solution will improve with the number of receive coils as well as with the orthogonality (i.e. magnitude of differences) between their respective coil sensitivities. The mismatch between 6 unknowns and a higher (or lower) number of receive channels can be taken into account by solving the system of equations in the least-squares sense.

The localization can also be carried out based on gradient field encoding. While the coil-sensitivity localization is based on the amplitude distribution picked up by the coil array, the frequencies of the markers can be manipulated to give an independent position information. To this end, a non-uniform magnetic field, ideally having a constant field gradient over the work space, is generated, e.g. by applying low frequency currents to selected coils of the coil array. This additional field changes the restoring field $B_{rest}$ acting on the oscillating sphere and thus its frequency (equation 9). Due to the non-uniform nature of the field, the frequency change will depend on position and orientation of the marker. By sequential application of several encoding fields (e.g. a field gradient applied in 6 different orientations), all three position and two of three orientation parameters of a marker can be determined. The remaining angle can be deferred from the higher order response of the sensor to external magnetic fields, however, at the cost of higher field strengths needed for generating sufficient higher order contributions. The basic encoding idea is related to gradient encoding in MRI; thus, both frequency encoding and phase encoding can be done.

For frequency encoding, the non-uniform field is applied during signal readout to produce the desired frequency offset. For a desired spatial resolution, the applied encoding field strength must be adapted to the frequency sensitivity of the marker and the frequency resolution the system delivers. Assuming a frequency sensitivity of a NdFeB marker with a sphere diameter of 0.5 mm is $$\frac{df}{dB} \approx -50 \text{ Hz/mT},$$

for a spatial resolution of $\Delta r=1$ mm and an assumed frequency resolution of $\Delta f=10$ mHz, a field gradient of roughly $$G = \frac{\Delta f}{\Delta r}\frac{dB}{df} \approx -0.2\frac{mT}{m} \qquad (17)$$

would be required. This gradient strength is about a factor of 100 below the gradient of typical MRI systems. Thus, no dedicated water-cooled gradient coils are needed, but the coils of the transmit-receive array can be used for field generation.

For phase encoding, the non-uniform encoding field is applied prior to the signal readout, i.e. the position-dependent frequency offset is only applied for a short window during which a position-dependent signal phase offset accrues. In case that the phase resolution is not sufficient for accurate localization, the duration and/or amplitude of the phase encoding pulses can be varied in sequential excitations, so that ambiguities in phase accruals (larger than 2 pi) can be discerned. Thus, full spatial information is obtained over the course of several readouts. Phase encoding with one non-uniform field pattern (e.g. encoding one spatial axis) can be combined with frequency encoding with another non-uniform field pattern (e.g. encoding an orthogonal spatial axis) for efficient localization. If a rough marker position is already known from the sensitivity-encoding approach (which is faster due to its parallel nature), it will suffice to only use few phase-encoding steps that provide the missing high resolution (high spatial frequency) components, but not the complete spatial information.

As described in this description, comparison of localization results obtained with gradient versus sensitivity encoding can be used to identify systematic errors, e.g. resulting from background fields. Furthermore, it should be noted that the linear response to low-frequency external fields of sensors employing two suspended sphere may be suppressed; in that case the higher order response of the frequency can be used for localization or for sanity checks. However, the field sensitivity of these oscillators is much lower so that higher gradient fields will be needed for gradient field encoding.

In the following parameter determination and position determination will be described for closely coupled sensors.

To determine the position (meaning 3 position and 3 orientation parameters) and measure a parameter (like pressure or temperature) is especially difficult if only few coils are used. However, using only a few coils is cost effective and also preferred in some application due to space restrictions. Therefore, it is desirable to modify the detection procedure and hardware in a way to work with only a few coils. One way to do this is to use several markers and/or sensors in a coupled fashion. Coupled means here that several sensors/markers, each operating at a distinct known frequency, are combined with fixed relative orientation in an assembly. Typically, the sensors are attached to a rigid frame, but technically only the relative positions of the sensors/markers need to be known at the evaluation time points. With enough sensors, the position can be determined with only two coils. This can be easiest seen when comparing to traditional electromagnetic navigation systems. These typically consist of several, usually more than 6, transmit coils and one receive coil which is located and whose orientation is evaluated. However, the rotation of the coil around its axis (axis of the dynamic dipole moment) cannot be detected due to the rotational symmetry of the coil. In this comparison, the set of rigidly coupled sensors may be viewed as a send array and the single transmit-receive coil as the marker. Thus, it is possible to locate the sensor/marker array somewhere at a ring around the dynamic dipole axis of the send coil. Note, if the coil is not round the rings are not perfect circles in space but this does not change the argument. So, the position cannot be determined with one coil, but two coils (with non-parallel dynamic dipole moment) the symmetry is broken and the position and orientation of the sensor/marker array can be determined. The evaluation of the different sensor signals is best done with the complete model approach which is described elsewhere in the document. In brief, a model of each sensor/marker in the array is generated i.e. in the form of differential equations. This model predicts the sensor response for a given excitation. Together with a send/receive system model (including amplifiers, filters and coils) the total response of the array can be predicted. Knowing the excitation pulses in the past (usually only the pulses for several decay times need to be known), the expected received signal for a sensor position and parameter value can be computed. Now the position/orientation of the sensor is optimized as well as the physical parameter the sensor measures to minimize the difference between computed and actually received signal. It is also possible to incorporate pre-knowledge into this procedure i.e. to allow only a maximum displacement speed of the sensors relative to the coils. Here the only difference to the previous described method is that this process is not done for one sensor but for a set of coupled sensors in an array or for several arrays simultaneously. With the sensor array there is also a set of pre-knowledge available, namely the relative positions and orientations of the sensors/markers in the array. It is especially useful to employ the full parametric approach or at least zero amplitude frequency extrapolation approaches as it is difficult to have all of the many sensors simultaneously operating at the desired amplitude. However, the full model approach is somewhat computational intense. To reduce the needed computing power, it may be beneficial to use first the already explained single sensor/marker evaluation approaches individually and use the results of them as starting values for a final full model-based position and value reconstruction.

In the following some calibration aspects will be explained, wherein firstly it is referred to calibration in the presence of conductive and soft ferromagnetic material.

The presence of conductive and especially soft ferromagnetic material may interfere with the localization by distorting the fields created by the oscillating magnet of the marker or sensor and/or by distorting the field(s) generated by the send coil(s). To a lesser degree, sensor readings may be altered, too, especially as the compensation for amplitude effects could be decreased in accuracy. Therefore, a calibration procedure for the fields is desirable. In addition, it is preferred to also have a measure to identify that field disturbances may happen at the moment. So, first, methods to detect disturbance problems are discussed. Typically, the localization system uses an array of send/receive coils. The coils can be separate send- and receive-only coils or use the same coil for both functionalities. Anyhow, in this configuration, one coil can send and all other coils directly receive the send signal. The receive signal is compared to stored reference values. If the actual received signal deviates too much from the stored values, some action is triggered, like a warning for inaccuracy, triggering a self-calibration process or a suggestion for a calibration process involving user interaction or a combination of these things. It is also possible to send with several coils simultaneously. The send pulse should contain a plurality of frequencies. This can be achieved by generating pulses or by using a frequency sweep or some intermediate, well known in the literature.

The frequency analysis is important, as eddy currents running on conductive structures are highly dependent on frequency. So, a significant change may be that the ratio of the received signal at two different frequencies is exceeding some limit. It may also be significant, if at least one spectral component changes by a defined value. However, a uniform change in the whole spectrum may be attributed to a gain change e.g. in the receive amplifier. So, if e.g. receive amplifiers are constructed in a way that gain changes are likely, this effect may be used to set a new gain value in the software to compensate for this gain change. The argument holds in a similar way, if a gain change is expected to happen in the send amplifier but not in the receive path. Here, as a correction, the send amplitude is changed in the computational model (leading to a change in oscillation amplitudes of the sensor, etc.). It is also theoretically possible to measure the impedance of a single coil and use the change in this as an indication for changes in the eddy current environment. However, the capability to measure impedance does not come naturally with the electronics and special equipment is needed. Not only the couplings of the coils can be used to detect environmental changes in the eddy currents, but also known properties of sensors/markers in the operation range. Especially, it is possible to incorporate sensors in the send/receive coil array itself. Even a single sensor/marker is useful. For example, if a single marker is incorporated into the system, at a fixed position relative to the coil(s), a change of the response of the marker is an indication of a changed eddy current environment. It is even more favorable to incorporate a sensor/marker that is sensitive to low frequency magnetic fields, but not, or only little to other physical properties that could change rapidly. This marker is not only an indication of a static magnetic field, but of the presence of ferromagnetic material. For detecting ferromagnetic material, the coils will not only be fed with current at frequencies of the sensor/marker oscillation, but also with a current at a much lower frequency. The current feeding can be done coil by coil or using several coils. If the measured sensor response (i.e. frequency change due to applied low-frequency magnetic field) is not the same as a stored expectation, it is likely that ferromagnetic material distorts the field. If enough coils are present in the system, it is even not necessary to have the field dependent sensor/marker at a known position. With enough coils, the marker position can be determined using the sensitivity of the coils at the sensor/marker oscillation frequency and independently by using the sensitivity of the sensor/marker to near DC magnetic fields (gradient field encoding). If the positions obtained by the two methods diverge, the eddy current (or ferromagnetic) environment has changed. However, it is even better if not only one such sensor is incorporated into the system, but many. It is also better to have them at known positions than at unknown positions. But it is also useful to have known only some properties of the positions instead of having no position information. A practical way of a partial knowledge is to have sensors/markers placed on a rigid structure that ensures a known and time-stable position and orientation relative to each other. Such a calibration "frame" with sensors/markers may be placed permanently or from time to time in the operation volume of the localization system. If the localization system finds relative positions and orientations that diverge from the expectations, the system is disturbed by eddy currents or ferromagnetic material. If again, the sensors/markers are also sensitive to near DC magnetic fields and the coil array has enough coils, the relative positions of the sensors/markers can be determined independently at very low frequencies where only ferromagnetic material disturbs the fields and at the sensor/marker resonance frequency, where both ferromagnetism and eddy currents lead to field distortions. Hence information about the nature of the disturbing objects can be generated e.g. if ferromagnetic material contributes to the disturbances. Again, the best approach to detect disturbances is a full mathematical model of the send/receive amplifiers, the coils, and the marker(s)/sensor(s). This model also includes known positions and orientations, both absolute and relative. In a first step, all positions/orientations and physical parameters are optimized in a way that the errors are minimized. This step includes the pre-knowledge e.g. about the fixed position markers attached to the coil array and the relative positions in potential frames. As a side note, the "frame" does not need to be something introduced only for calibration, but a marker consisting of many oscillators can act as a frame by itself. In the second step, a total weighted error between expected signals and delivered signals is computed. If the error is over a certain threshold value, it is concluded that some material disturbs the fields. From the nature of the error (i.e. if it occurs on the AC sensitive components or the DC sensitive components) the nature of the disturbing material can be deduced.

The last method to determine the presence of field disturbances is also a good starting point for methods to compensate for the effects of the field disturbances. The method can be easiest illustrated when assuming that conductive material causing eddy currents is present, but not ferromagnetic material. When applying the model described above, we get the right positions from the evaluation of the near-DC dependent signals (gradient field encoding), but the wrong positions and local field amplitudes at the sensor frequency and its harmonics (coil sensitivity encoding). Therefore, we can distort the higher frequency fields in a way to match the expectations. After the distortion is applied, all positions and sensor readings will be improved. It is beneficial not to solely rely on the position evaluation based on the near DC magnetic fields, because the AC sensitivity encoding is much faster. The most critical part for this compensation method is to determine the right model for the distortion of the AC field. A simple solution is to parameterize a field shift function e.g. using simple 3D polynomials. This means that the field value is not used of the actual position, but of the position transformed by the 3D polynomials. This is computationally efficient but may lack physical insight and it is not apparent, how e.g. the measurements of the coil couplings could be incorporated into this framework. So, it is better to use models that are closer to the physical reality. For example, it is better to use the field model of conductive plates near the coil system to induce the desired field distortions. So basically position, angle thickness, and size of some virtual plates are varied until the model expectations and the measured data match. How to model such conductive plates is well known in the electromagnetic simulation literature. This type of modeling has the additional advantage that it is easy to incorporate the shapes of objects that will likely occur in a specific environment. So, if a special device is brought close to the field of view, e.g. an X-ray C-arm, this device is known and can be modelled before, so that only the exact orientation and position has to be optimized by the system software. A further advantage is that the assumed disturbing object position can be displayed by the system or the data is transmitted to a second system that does the display task. In this way, the user can be specifically pointed to objects that disturb the measurement and the user may want to move or remove them. During this process, the coupling data of the coils act essentially as an array of metal detectors. The incorporation of ferromagnetic material is conceptually the same as with the conductive material that produces eddy currents. However, ferromagnetic material simulation is a computationally a little more intense and as there may be a lack of definite reference positions defined by dedicates markers, it may not result the exact position. But again, it is best to model a set of ferromagnetic material, like sheets and rods and place and deform them in simulation around the coil array. Here it is very beneficial for the model if a database of likely ferromagnetic objects is provided. In addition, the process of mutual coupling measurements could be augmented by the measurement of harmonics generation in the coil environment. The presence of harmonics is a strong indication for soft ferromagnetic material and the measured signals give valuable input for the size and position of the objects.

In the following an excitation pulse generation will be described.

The system preferentially comprises software to generate the timing and shape of the excitation pulses. This excitation pulse generator is preferentially aware of the capability of the hardware. There are different types of amplifiers and filtering possible. One type of amplifier is capable of generating a current waveform that closely follows a rather arbitrary path. These are here called "analog amplifiers". The other is only capable of increasing the current at a predefined rate, decreasing it at a similar rate, and letting it more or less constant. In essence, these amplifiers apply a voltage with positive or negative sign at the coil or act as a short circuit. These are here called "digital amplifiers". The digital amplifiers can have different switching speeds i.e. allowed number of state changes per unit time. If the switching speed is much higher that the oscillation speed, the digital amplifier again acts like an analog amplifier. Hence, this type of amplifier can be conceptually treated as an analog amplifier. If the switching speed is only about the same as the marker/sensor oscillation frequency, the treatment has to be a little different. However, this is the more difficult situation, therefore all the discussion will focus on that. This type of amplifier has some benefit over the analog ones. The main benefit is that the efficiency of this amplifier is usually very high and a 98% efficiency is readily achieved. A further advantage is that interfacing with the computing system is very easy. Between amplifier and coil, a matching circuit could be present. The simplest matching circuit is just a capacitor in series to the coil. Using the matching circuit, the maximum current through the coil at a given amplifier supply voltage increases. Such a matching circuit however has the drawback of blocking low frequency currents. Some sequences may require low frequency currents. Solutions to this problem can be twofold. First, a matching circuit can be provided that is transparent at high and low frequencies. An example of such a circuit would be a coil or coil capacitor series circuit parallel to the first matching capacitor. The other way is to have a switch that bypasses the matching circuit and when near DC current is needed, the switch is closed. In the bypass path, a capacitor can be integrated, too, if the resonance frequency is low enough. In the same way, a whole series of different matching frequencies can be provided using a multitude of switches and capacitors. Also, note that even if the circuit is tuned to near DC, some current at the marker/sensor resonance frequency is still available. It shall be noted, that it is not necessarily possible to use the DC currents during read-out. There are two main elements to provide this capability. First, the DC currents are not allowed to interfere with the reading. There is manly a problem if the send and receive coils are combined. The DC source can provide a short circuit path to the signal. This has to be avoided and the proper matching circuit avoids it. The matching circuit has to introduce a sufficiently high impedance between the coil and the DC source. This can be achieved by an additional coil in series with an inductivity on the order of the send/receive coil inductivity. The inductivity may have a parallel switch to short it if it is not needed. There are many other solutions available. Second condition is that the DC source does not introduce too much noise i.e. the current source noise does not prohibit the accurate measurement of the markers/sensors. This can be achieved by a suitable analog filter in the DC send case. This filter may be a bypassed during AC send pulses by a suitable switch (MOSFET opto-couplers for example). It may also be feasible to avoid switching action in the DC source during signal receiving altogether and just use the slowly decaying current in the coil. It may be also feasible to do only a few switching actions while receiving and just dismiss the received data when they are corrupted. The DC field sources may be also entirely separate coils or the field generators may be (moving) permanent magnets. This avoids most problems. An additional issue with the presence of DC currents during signal reception is that the coils may provide a different environment for the sensors. This means, that for example some coils can be shortened for AC currents and the AC field do no more penetrate the coils changing field values in nearby coils. This effect has to be taken into account when computing positions and sensor values. Two main field elements interact with the sensor/marker. One is the near DC amplitude of the current i.e. a current value averaged over a time in the order of 0.1 seconds (about 0.01 seconds to about 1 second). The other is the Fourier amplitude (as a complex value, as the phase is important) at the resonance frequency of the sensors/markers. Therefore, the first task is to map the two values to the generation of the sequence.

In the following a mapping if desired Fourier amplitudes and currents to a specific time-domain pulse pattern will be described.

It is also useful to generate a software sub-system that does this exact type of mapping i.e. a piece of software that gets the desired near DC currents and the desired Fourier amplitude (and frequency) as an input and that generates the time-domain pulse sequences. It is also desired that this software returns the information whether the desired values can be reached within the limits imposed by the hardware, like maximum currents or maximum heating of coils or regulatory limitations, e.g. patient heating or peripheral nerve stimulation. Instead of a simple yes/no information, an information about the severity of the undesired side effects may be provided. This information may be provided per individual send cannel (per send coil). A further return value may be the actual best-fit output DC current and Fourier amplitude(s). The input may not only be one frequency and Fourier amplitude combination, but also a variety of Fourier amplitudes at different frequencies. The maximum length of the pulse sequence may also be a parameter that is an input for this function. The inner workings of are as follows: In the case of analog amplifiers, a first result may be generated simply by doing the inverse Fourier transform of the desired Fourier amplitudes (and DC values) for the desired send time. If this process results in a wave form that cannot be realized due to some limitations, this is reported back and maybe a scaled version is scheduled for generation. The possible filter characteristics is accounted for by the appropriate convolution. If there are several switched filter states, all may be tested and the one with the lowest demand on the amplifier may be chosen. Note that there are several heuristics available, so that for most cases not all filter states have to be evaluated. It is for example possible to omit filters with far off resonance frequencies, if better ones are available. For the digital amplifier, the inverse Fourier transform (including filter effects) gives a good starting point for optimization. In this first approximation step, the resulting peaks in the time spectrum are approximated by two (or at best a few) ramps and flat regions in between. So, for example a half period of a sine wave starting with zero and ending with zero is approximated by first a flat (zero) portion, then a ramp up, then a flat portion, then a ramp down, and finally a flat (zero) region. The timing of the different portions is arranged in a way to reach approximately the same area. After this first approximation, a second step, where the positions of the ramp and flat part beginnings are shifted to reach a fest fit with the desired Fourier values. The best fit may be the least sum of squares of difference (complex) values of desired and achieved Fourier components. All the usual optimization algorithms, like gradient descent, can be used.

In the following a mapping of desired Fourier values at sensors/markers to currents in coils will be described.

The next higher abstraction level of the pulse generation program is the software piece that demands specific field Fourier values and directions at a specific position as an input and translates them to the demands for the currents in the coil. The evaluation algorithm usually provides some measure of position and orientation of the sensors/markers. The position is not and does not need to be a position in 3D space. However, a 3D position is the ideal case. For example, if only one coil is present, it may be only possible to determine the field value in sensitive direction at the sensor. Nevertheless, this also translates into some virtual position and orientation in 3D space. Therefore, these situations do not need a special handling in the software. The translation to the demands for coil currents are then the result of an optimization process. There is a model that computes from currents in the coils Fourier field components at specific spatial positions. This is the basis for an optimization, where coil current Fourier components are optimized in a way to generate the desired field components. There is usually not an unambiguous way to form the desired fields out of coil currents. It may also be the case that the desired currents are not compatible with the restrictions in the hardware system. The lower level software returns values describing the negative effects and the software uses this information to optimize the currents. The optimization has the goal to have a good compromise between achieved field Fourier components at the sensors/markers and the negative effects. This means that the deviation from the desired fields and the side effects are combined into one number and for this number a maximum or minimum is found using standard optimization algorithms. The combination of the number may be a weighted sum of squares. Naturally for this entity a huge number of working mathematical combinations can be found. Finally, this part of the program returns the calling program (higher level) the achieved fields at the positions and the quality values for it to do its optimization.

In the following a generation of desired field Fourier values for the markers/sensors will be described.

At this level of abstraction, the software system actually deals with the measurements that need to be done. So, the input for this program is the current demand of what things shall be measured how accurately and how fast. These requirements depend on the actual application the sensors/markers are used and therefore are not part of this document. The requirements could be very different. For example, if only a single sensor is involved, the requirement would be for example measure the single quantity as accurately as possible every say 0.1 seconds. If the application is a tracking solution with multiple coupled markers, the desired outcome may be that say every 0.1 seconds a position update is made for the whole marker assembly regardless of which of the markers/sensors in it contribute to the signal (based on coil sensitivities) and that every 1 second an independent position check with the gradient method is demanded. This program also has access to the current state of the sensors/markers (position/oscillation parameters etc.) and the simulation model described elsewhere in this document. From this, the optimal excitation field Fourier values including direction for each sensor/marker can be computed. These parameters can be passed to the previously described lower software levels (with a wanted execution somewhere in the future) to ultimately generate the currents. In the case of the single sensor, this would work immediately and the plan can be written to the hardware output buffers. However, for the tracking of the marker assembly for example, there exists likely no pulse shape that excites all individual sensors/markers perfectly. Especially the phase would be not suitable for all the individual sensors/markers. Therefore, the software may have to try to concentrate the optimal excitation to just a sub-set of the sensors/markers present and try to find a solution which gives working pulse sequence. This is the general working principle of the optimization of this software. It tries to change the desired excitation of the various sensors and focusing on a few to still get the desired outcome. The conceptually simplest approach is to go through all possible sub-sets of sensors/markers and check which sub-set of excitation gives the best information on the desired parameters. As there are many sub-sets possible, the program needs to add some heuristic methods to reduce the complexity. For example, it can be first observed what other markers/sensors are excited too, if a given one is excited and these can be always grouped together. If a suitable solution is found, it can be written to the output buffer. The inclusion of near DC magnetic fields may need an additional logic depending on the hardware implementation. If the hardware is capable of applying DC magnetic fields, while the signals are recorded, the software does not have to do something very special, except applying one or several gradients during read-out. However, if DC gradients and read-out are incompatible, there is an additional optimization step needed, that produces the right DC field or gradient at some time in between excitation pulses. The logic behind the optimization remains the same. Parameters are varied until the simulation predicts a good enough measured value for the application.

A start-up sequence generation will be described in the following.

The algorithm generally assumes that there is already quite some knowledge about the sensors available to optimize the sequence. Usually, at the start of the sequence, this is not available in full. For example, from the application it could be known how many sensors/markers should be present in the application and in which range the frequencies could be. But the exact frequencies and positions would not be known. Therefore, a special start-up sequence is needed that tries to find all possible sensors at all possible positions. The simplest possible start-up sequence is as follows. The working volume is split into a spatial 3D or abstract grid. The abstract grid is the grid to use if there are not enough coils to do a full 3D encoding. Each spatial point is split into different directions. The program goes through each position and each angle at the position and applies the highest send power for a given frequency and a pre-set send time. Then the system records the potential signals from the sensors/markers. Usually, one send pulse excites not only one marker but also many others simultaneously. However, this procedure ensures that even the sensor/marker with the weakest possible signal will be detected, too. An optional next step is to excite each sensor individually with different amplitudes. From this, the non-linear properties can be extracted. A further optional step is to excite each sensor/marker in the presence of a DC field or a measure the signal phase after a DC field (again in various directions) to determine the sensitivity of the sensors/markers to DC magnetic fields. These basic procedures can be sped up tremendously by using some knowledge about the system. For example, it is likely that, if a faraway volume is already searched for a sensor/marker, many or all nearer volumes received the highest possible amplitude at least for some angles. Therefore, only the few remaining parameters need to be applied for the nearer volumes. The same logic can be used for assessing the non-linear character of the sensors/markers or their response to DC magnetic fields.

In the following strategies for high temporal resolution measurements are explained.

For many applications, it is desirable to have a high temporal resolution. One example is measurement of intra-vascular pressure that is modulated by the cardiac cycle that can reach frequencies up to 200 beats/minute in a human. In order to determine pressure minima and maxima during a cardiac cycle, a minimum measurement frequency around 5 Hz is required, preferably above 10-20 Hz, most preferably above 40 Hz. On the other side, in order to have a good signal to noise a very high Q factor for the oscillator is needed. High Q factor means a slow decay. Consequently, when a next measurement pulse is sent to the sensor, the oscillations from the previous measurement pulse are not fully extinguished and they would affect the measurement.

So, strategies are desired to reach a high temporal resolution with the magneto-mechanical oscillators, both for localization and parameter determination. The simplest approach for a high temporal resolution is to simply decrease the repetition time. Repetition time means the time period between subsequent excitation pulses. After each excitation pulse, the frequency and amplitudes are determined from which the physical values and position can be computed, as described elsewhere. However, the quality factor of the sensors/markers tends to be relatively high and the oscillation amplitude has not declined much at the time of the next excitation pulse. To always get the desired sensor/marker excitation, the phase of the next excitation has to be considered. Usually, we want an "in phase excitation", i.e. an excitation in a way that the sensor/marker gains energy right from the start of the excitation pulse. How the timing is optimized is described elsewhere. The in phase excitation minimizes the send energy and hence the excitation pulse length can be kept to a minimum. This increases overall signal to noise ratio.

The high repetition rate has some drawbacks. First, during and shortly after the excitation pulses, the system usually cannot receive values and hence the signal to noise ratio may not be optimal. Secondly, each send pulse destroys some knowledge about the phase of the sensors' oscillation. Only if the excitation pulse and sensor orientation are kept tightly controlled and are precisely known, the phase information can survive to some degree, however this is technological challenging. The phase information over a longer period may be useful, as in it, information about the average frequency (hence average physical quantity) is encoded. The measurement of an average physical quantity is considerably more accurate when evaluating a double length interval than just doing the evaluation of the first half and the second half independently and averaging the two results. Therefore, it may worthwhile to have not as many excitation pulses as measurements but extract from one signal pulse more than one measured value. This can be done simply by splitting the signal in several sub-sections and evaluating each subsection individually. This simple approach does not take into account that the measurements become better, if a longer data set is used. To incorporate this, the set can be split into a hierarchy of sub sets and every sub-set in every hierarchy is evaluated and the averages are scaled to match the longer data sets. So, for example a data set (one unperturbed decaying signal) is first evaluated as a whole. Then it is split into two, and the two split data sets are separately evaluated. Then to each result the same number is added so that their average matches the average of the full set. This process can be repeated to have 4, 8 and so on sub-sets in the end. This approach may be refined mathematically to a full model-based evaluation. For this, a model of the evolution of the physical parameter is generated (and possibly also including the spatial movement of the sensor). This model may be a polynomial of a certain degree or some other suitable mathematical function. The function should describe the physical nature of the measured quantity in a way so that only a low number of parameters needs to be used. So, for example when the parameter is the blood pressure, the model may be better a Fourier series, because this describes the pressure wave form of heart beats better than polynomials. Then the parameters are varied to match the measured data set as good as possible. If discrete measurement points are needed in the end, they can be simply computed using the output of the model for certain time points.

It should be noted that all described embodiments comprise a diffusion blocking layer which covers at least a part of the casing and which is configured to maintain a predetermined pressure within the casing, even if the diffusion blocking layer is not shown in all figures for clarity reasons. Also the configuration of the pressure sensor such that a temperature compensation of the resonance frequency is provided can be applied to any described embodiment.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the resonance frequency based on the induced signal, the determination of the pressure based on the resonance frequency, the determination of a calibration curve et cetera performed by one or several units or devices can also be performed by any other number of units or devices. The control of the detection system can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a passive pressure sensor for being introduced into the circulatory system of a human being and for being wirelessly read out by an outside reading system. The pressure sensor comprises a casing with a diffusion blocking layer for maintaining a predetermined pressure within the casing and a magneto-mechanical oscillator with a magnetic object providing a permanent magnetic moment. The magneto-mechanical oscillator transduces an external magnetic or electromagnetic excitation field into a mechanical oscillation of the magnetic object, wherein at least a part of the casing is flexible for allowing to transduce external pressure changes into changes of the mechanical oscillation of the magnetic object. The pressure sensor can be very small and nevertheless provide high quality pressure sensing.

The invention claimed is:

1. A pressure sensor for being introduced into the circulatory system of a subject, comprising:
   a casing comprising a diffusion blocking layer covering at least a part of the casing and configured to maintain a predetermined pressure within the casing, and
   a magneto-mechanical oscillator comprising a magnetic object providing a permanent magnetic moment within the casing, wherein the magneto-mechanical oscillator is configured to transduce an external magnetic or electromagnetic excitation field into a mechanical oscillation of the magnetic object,
   wherein at least a part of the casing is flexible for allowing transducing external pressure changes into changes of the mechanical oscillation of the magnetic object,
   wherein the pressure sensor is a passive sensor configured to be wirelessly read out by a reading system placed outside the subject.

2. The pressure sensor as defined by claim 1, wherein the magnetic object is arranged within the casing such that it is rotatable out of an equilibrium orientation if the external magnetic or electromagnetic excitation field is acting on the magnetic object, wherein the pressure sensor further comprises:
   a torque restorer to force the magnetic object back into the equilibrium orientation if the external magnetic or electromagnetic excitation field has rotated the magnetic object out of the equilibrium orientation, in order to allow for the mechanical oscillation of the magnetic object with a resonance frequency,
   wherein the pressure sensor is configured such that the external pressure changes are transduced into changes of the resonance frequency.

3. The pressure sensor as defined by claim 1, wherein pressure sensor has an elongated shape with a maximum dimension being smaller than or equal to 5 mm and a minimum dimension being smaller than or equal to 1 mm.

4. The pressure sensor as defined by claim 1, wherein the pressure sensor comprises an external biocompatible coating.

5. The pressure sensor as defined by claim 1, wherein the flexible part of the casing comprises a bellows for allowing transducing the external pressure changes into changes of at least one of an amplitude or a resonance frequency of the mechanical oscillation of the magnetic object.

6. The pressure sensor as defined by claim 5, wherein the pressure sensor further comprises an outer cover over the bellows.

7. The pressure sensor as defined by claim 1, wherein the diffusion-blocking layer comprises metal.

8. The pressure sensor as defined by claim 1, wherein the pressure sensor comprises an outer wire cage attached to the outer of the casing for allowing the outer of the casing to keep a distance to a vessel wall.

9. The pressure sensor as defined by claim 1, wherein the magnetic object and/or an inner surface of the cavity is coated with a slippery non-sticking material.

10. The pressure sensor as defined by claim 1, wherein the pressure sensor is constructed such that the magnetic object is alignable with an external magnetic field regardless of the position and orientation of the pressure sensor in the external magnetic field.

11. The pressure sensor as defined by claim 10, wherein the pressure sensor comprises an outer housing enclosing the casing, wherein the casing is rotatable within the enclosing housing, wherein the pressure sensor is configured such that external pressure changes outside the enclosing housing are transferred to external pressure changes being externally of the casing and internally of the enclosing housing.

12. The pressure sensor as defined by claim 10, wherein the magnetic object is a magnetic sphere which is attached to one end of a filament, wherein another end of the filament is attached to the inner of the casing, wherein the filament has a length of at least Pi/4 of the diameter of the magnetic sphere.

13. The pressure sensor as defined by claim 10, wherein the magnetic object is a magnetic sphere which is attached to one end of a filament, wherein another end of the filament is attached to a length changing unit configured to allow for a change of the length of the filament and attached to the inner of the casing.

14. The pressure sensor as defined by claim 1, wherein the pressure sensor is configured to compensate a dependence of the resonance frequency on the temperature.

15. The pressure sensor as defined by claim 14, wherein the pressure sensor comprises a compensator, the resonance frequency being modified by the compensator in a first frequency direction depending on a temperature change which is opposite to a second frequency direction in which the resonance frequency of the pressure sensor would be modified, depending on the temperature change, if the compensator were not part of the pressure sensor.

16. A reading system for wirelessly reading out a pressure sensor as defined by claim 1, wherein the reading system comprises:
   a field generator for generating a magnetic or electromagnetic excitation field for inducing mechanical oscillations of the magnetic object of the pressure sensor,
   a transducer for transducing a magnetic or electromagnetic field generated by the induced mechanical oscillations of the magnetic object of the pressure sensor into electrical response signals,
   a processor for determining a pressure value based on the electrical response signals.

17. The reading system as defined by claim 16, wherein the processor is configured to apply a compensation algorithm, in order to correct the determination of the pressure value for a dependence of the electrical response signals on at least one of
   a) a distance between the pressure sensor and the field generator;

b) a phase of a mechanical oscillation of the magnetic object;
c) an orientation of the casing relative to the reading system; and
d) an amplitude of the mechanical oscillation of the magnetic object.

18. The reading system as defined in claim 16, wherein the field generator comprises a coil or a plurality of coils which are controllable by the processor and the transducer is either part of the field generator or a separate pick-up coil.

19. £ (Previously Amended) A pressure measuring method for carrying out a measurement by using a pressure sensor as defined by claim 1,
wherein the pressure measuring method comprises:
generating a magnetic or electromagnetic excitation field for inducing mechanical oscillations of the magnetic object of the pressure sensor;
transducing a magnetic or electromagnetic field generated by the induced mechanical oscillations of the magnetic object of the pressure sensor into electrical response signals; and
determining a pressure value based on the electrical response signals.

20. The pressure measuring method of claim 19, the method further comprising in the determining step correcting a pressure value for a dependence of the electrical response signals on at least one of
a) a distance between the pressure sensor and the field generator;
b) a phase of a mechanical oscillation of the magnetic object;
c) an orientation of the casing relative to the reading system; and
d) an amplitude of the mechanical oscillation of the magnetic object.

21. A non-transitory computer readable medium storing machine executable instructions for causing a reading system as defined by claim 16 to carry out a pressure measuring method when the instructions are executed by a computer controlling the reading system,
wherein the pressure measuring method comprises:
generating a magnetic or electromagnetic excitation field for inducing mechanical oscillations of a magnetic object of a pressure sensor;
transducing a magnetic or electromagnetic field generated by the induced mechanical oscillations of the magnetic object of the pressure sensor into electrical response signals; and
determining a pressure value based on the electrical response signals.

\* \* \* \* \*